United States Patent
Ahuja et al.

(10) Patent No.: US 10,619,210 B2
(45) Date of Patent: Apr. 14, 2020

(54) PREDICTING RESPONSE TO EPIGENETIC DRUG THERAPY

(71) Applicant: THE JOHNS HOPKINS UNIVERSITY, Baltimore, MD (US)

(72) Inventors: Nita Ahuja, Lutherville, MD (US); Stephen B. Baylin, Baltimore, MD (US); Katherine Chiappinelli, Baltimore, MD (US); Angela Anne Guzzetta, Little Falls, NJ (US); Huili Li, Ellicott City, MD (US); Cynthia Zahnow, Bel Air, MD (US)

(73) Assignee: The Johns Hopkins University, Baltimore, MD (US)

( * ) Notice: Subject to any disclaimer, the term of this patent is extended or adjusted under 35 U.S.C. 154(b) by 249 days.

(21) Appl. No.: 15/115,702

(22) PCT Filed: Feb. 9, 2015

(86) PCT No.: PCT/US2015/015017
§ 371 (c)(1),
(2) Date: Aug. 1, 2016

(87) PCT Pub. No.: WO2015/120382
PCT Pub. Date: Aug. 13, 2015

(65) Prior Publication Data
US 2017/0009303 A1    Jan. 12, 2017

Related U.S. Application Data

(60) Provisional application No. 61/937,149, filed on Feb. 7, 2014, provisional application No. 61/940,488, filed on Feb. 16, 2014.

(51) Int. Cl.
*C12Q 1/68*    (2018.01)
*C12Q 1/6886*    (2018.01)

(52) U.S. Cl.
CPC ..... *C12Q 1/6886* (2013.01); *C12Q 2600/106* (2013.01); *C12Q 2600/112* (2013.01); *C12Q 2600/118* (2013.01); *C12Q 2600/154* (2013.01); *C12Q 2600/158* (2013.01)

(58) Field of Classification Search
None
See application file for complete search history.

(56) References Cited

U.S. PATENT DOCUMENTS

| | | |
|---|---|---|
| 4,981,785 A | 1/1991 | Nayak |
| 5,188,934 A | 2/1993 | Menchen et al. |
| 5,270,163 A | 12/1993 | Gold et al. |
| 5,358,691 A | 10/1994 | Clark et al. |
| 5,366,860 A | 11/1994 | Bergot et al. |
| 5,411,876 A | 5/1995 | Bloch et al. |
| 5,413,924 A | 5/1995 | Kosak |
| 5,432,272 A | 7/1995 | Benner |
| 5,475,096 A | 12/1995 | Gold et al. |
| 5,538,848 A | 7/1996 | Livak et al. |
| 5,550,044 A | 8/1996 | Kosak |
| 5,567,588 A | 10/1996 | Gold et al. |
| 5,595,877 A | 1/1997 | Gold et al. |
| 5,637,459 A | 6/1997 | Burke et al. |
| 5,660,985 A | 8/1997 | Pieken et al. |
| 5,670,637 A | 9/1997 | Gold et al. |
| 5,683,867 A | 11/1997 | Biesecker et al. |
| 5,696,249 A | 12/1997 | Gold et al. |
| 5,707,796 A | 1/1998 | Gold et al. |
| 5,800,996 A | 9/1998 | Lee et al. |
| 5,847,162 A | 12/1998 | Lee et al. |
| 5,863,727 A | 1/1999 | Lee et al. |
| 5,885,530 A | 3/1999 | Babson et al. |
| 5,925,517 A | 7/1999 | Tyagi et al. |
| 5,936,087 A | 8/1999 | Benson et al. |
| 5,945,526 A | 8/1999 | Lee et al. |
| 5,965,364 A | 10/1999 | Benner |

(Continued)

FOREIGN PATENT DOCUMENTS

| | | |
|---|---|---|
| WO | 1997045539 A1 | 12/1997 |
| WO | 2001031580 A2 | 5/2001 |

(Continued)

OTHER PUBLICATIONS

Strausberg et al, in Microarrays and Cancer Research, 2002, Warrington et al (eds.), Eaton Publishing, Westborough, MA, pp. xi-xvi.*

Notterman et al, in Microarrays and Cancer Research, 2002, Warrington et al (eds.), Eaton Publishing, Westborough, MA, pp. 81-111.*

Chen, et al., Real-time quantification of microRNAs by stem-loop RT-PCR. Nucleic Acids Res. Nov. 27, 2005;33(20): e179.

Li, et al., Antiprimer quenching-based real-time PCR and its application to the analysis of clinical cancer samples. Clin Chem. Apr. 2006;52(4):624-33.

Schouten, et al., Relative quantification of 40 nucleic acid sequences by multiplex ligation-dependent probe amplification. Nucleic Acids Res. Jun. 15, 2002;30(12):e57.

(Continued)

*Primary Examiner* — James Martinell
(74) *Attorney, Agent, or Firm* — Johns Hopkins Technology Ventures

(57) ABSTRACT

The present invention relates to the field of epigenetics. More specifically, the present invention provides methods and compositions useful for predicting response to epigenetic drug therapy. As described herein, we have identified a unique signature termed AZA Immune gene set or AIM that differentiates patients with a low immune and high immune signature and is regulated by epigenetic drugs such as demethylating drugs, histone deacetylase inhibitors. In certain embodiments, patients with a high immune signature may benefit from immunotherapies such as anti PD1 or anti PDL1 antibodies or vaccines. In other embodiments, patients with a low immune signature or low AIM would be patients who would then benefit from treatment with epigenetic drugs and then subsequent immunotherapy.

11 Claims, 55 Drawing Sheets

(56) References Cited

U.S. PATENT DOCUMENTS

| | | | |
|---|---|---|---|
| 5,985,619 | A | 11/1999 | Sutherland et al. |
| 6,001,983 | A | 12/1999 | Benner |
| 6,008,379 | A | 12/1999 | Benson et al. |
| 6,011,020 | A | 1/2000 | Gold et al. |
| 6,020,481 | A | 2/2000 | Benson et al. |
| 6,051,719 | A | 4/2000 | Benson et al. |
| 6,103,476 | A | 8/2000 | Tyagi et al. |
| 6,140,054 | A | 10/2000 | Wittwer et al. |
| 6,140,500 | A | 10/2000 | Yan et al. |
| 6,150,097 | A | 11/2000 | Tyagi et al. |
| 6,159,750 | A | 12/2000 | Edmonds |
| 6,191,278 | B1 | 2/2001 | Lee et al. |
| 6,329,144 | B1 | 12/2001 | Kubista et al. |
| 6,355,421 | B1 | 3/2002 | Coull et al. |
| 6,383,752 | B1 | 5/2002 | Agrawal et al. |
| 6,403,341 | B1 | 6/2002 | Barnes |
| 6,485,901 | B1 | 11/2002 | Gildea et al. |
| 6,548,250 | B1 | 4/2003 | Sorge |
| 6,590,091 | B2 | 7/2003 | Albagli et al. |
| 6,593,091 | B2 | 7/2003 | Keys et al. |
| 6,596,490 | B2 | 7/2003 | Dattagupta |
| 6,649,349 | B2 | 11/2003 | Gildea et al. |
| 7,060,809 | B2 | 6/2006 | Wengel et al. |
| 2002/0138208 | A1 | 9/2002 | Paulse et al. |
| 2002/0193950 | A1 | 12/2002 | Gavin et al. |
| 2003/0004402 | A1 | 1/2003 | Afeyan et al. |
| 2003/0055615 | A1 | 3/2003 | Zhang et al. |
| 2006/0078894 | A1 | 4/2006 | Winkler |
| 2009/0325176 | A1* | 12/2009 | O'Toole ............... C12Q 1/6883 435/6.16 |
| 2010/0093557 | A1 | 4/2010 | Kumble |
| 2010/0190656 | A1 | 7/2010 | Li et al. |
| 2013/0005837 | A1* | 1/2013 | Moreno ............... C12Q 1/6886 514/789 |

FOREIGN PATENT DOCUMENTS

| | | | |
|---|---|---|---|
| WO | 2008100913 | A2 | 8/2008 |
| WO | 2012122219 | A2 | 9/2012 |
| WO | 2012170711 | A1 | 12/2012 |
| WO | 2013041731 | A1 | 3/2013 |

OTHER PUBLICATIONS

Ruczinski, et al., Logic Regression. J Computational and Graphical Statistics. 2003;12(3):475-511/.

Friedman, Regularized Discriminant Analysis. J AM Statistical Assoc. Mar. 1989;84(405):165-175.

Breiman, Random Forests. Machine Learning. Oct. 2001;45(1):5-32.

Jain, et al., Statistical pattern recognition: a review. IEEE Transactions on Pattern Analysis and Machine Intelligence. Jan. 2000;22(1):4-37.

Baylin, et al., A decade of exploring the cancer epigenome—biological and translational implications. Nat Rev Cancer. Sep. 23, 2011; 11(10): 726-734.

Kaminskas, et al., Approval summary: azacitidine for treatment of myelodysplastic syndrome subtypes. Clin Cancer Res. May 15, 2005;11(10):3604-8.

Juergens, et al., Combination epigenetic therapy has efficacy in patients with refractory advanced non-small cell lung cancer. Cancer Discov. Dec. 2011;1(7):598-607.

Matei, et al., Epigenetic resensitization to platinum in ovarian cancer. Cancer Res. May 1, 2012;72(9):2197-205.

Wrangle, et al., Alterations of immune response of Non-Small Cell Lung Cancer with Azacytidine. Oncotarget. Nov. 2013;4(11):2067-79.

Tsai, et al., Transient low doses of DNA-demethylating agents exert durable antitumor effects on hematological and epithelial tumor cells. Cancer Cell. Mar. 20, 2012;21(3):430-46.

Subramanian, et al., Gene set enrichment analysis: a knowledge-based approach for interpreting genome-wide expression profiles. Proc Natl Acad Sci U S A. Oct. 25, 2005;102(43):15545-50.

Toyota, et al., CpG island methylator phenotype in colorectal cancer. Proc Natl Acad Sci U S A. Jul. 20, 1999;96(15):8681-6.

Schuebel, et al., Comparing the DNA hypermethylome with gene mutations in human colorectal cancer. PLoS Genet. Sep. 2007;3(9):1709-23.

Jeschke, et al., Biomarkers for detection and prognosis of breast cancer identified by a functional hypermethylome screen. Epigenetics. Jun. 2012;7(7):701-709.

Ahuja, et al., Harnessing the potential of epigenetic therapy to target solid tumors. J Clin Invest. Jan. 2014;124(1):56-63.

Platanias, Mechanisms of type-I- and type-II-interferon-mediated signalling. Nat Rev Immunol. May 2005;5(5):375-86.

Greiner, et al., Enhanced expression of surface tumor-associated antigens on human breast and colon tumor cells after recombinant human leukocyte alpha-interferon treatment. Cancer Research. Aug. 1984;44:3208-3214.

Karpf, et al., Limited gene activation in tumor and normal epithelial cells treated with the DNA methyltransferase inhibitor 5-aza-2'-deoxycytidine. Mol Pharmacol. Jan. 2004;65(1):18-27.

James, et al., DNA methylation and nucleosome occupancy regulate the cancer germline antigen gene MAGEA11. Epigenetics. Aug. 1, 2013; 8(8): 849-863.

Karpf, et al., Increased Expression of Androgen Receptor Coregulator MAGE-11 in Prostate Cancer by DNA Hypomethylation and Cyclic AMP. Mol Cancer Res. Apr. 2009;7(4):523-535.

Akers, et al., Regulation of cancer germline antigen gene expression: implications for cancer immunotherapy. Future Oncol. May 2010;6(5):717-32.

Almeida, et al., CTdatabase: a knowledge-base of high-throughput and curated data on cancer-testis antigens. Nucleic Acids Res. Jan. 2009;37(Database issue):D816-9.

Weigman, et al., Basal-like Breast cancer DNA copy number losses identify genes involved in genomic instability, response to therapy, and patient survival. Breast Cancer Res Treat. Jun. 2012;133(3):865-80.

Roepman, et al., Colorectal cancer intrinsic subtypes predict chemotherapy benefit, deficient mismatch repair and epithelial-to-mesenchymal transition. Int J Cancer. Feb. 1, 2014; 134(3): 552-562.

Bonome, et al., A gene signature predicting for survival in suboptimally debulked patients with ovarian cancer. Cancer Res. Jul. 1, 2008;68(13):5478-86.

Easwaran, et al., A DNA hypermethylation module for the stem/progenitor cell signature of cancer. Genome Res. May 2012;22(5):837-49.

Schrieber, et al., Cancer immunoediting: integrating immunity's roles in cancer suppression and promotion. Science. Mar. 25, 2011;331(6024):1565-70.

Topalian, et al., Cancer immunotherapy comes of age. J Clin Oncol. Dec. 20, 2011;29(36):4828-36.

Cihak, Biological effects of 5-azacytidine in eukaryotes. Oncology. 1974;30(5):405-22.

Haaf, The effects of 5-azacytidine and 5-azadeoxycytidine on chromosome structure and function: implications for methylation-associated cellular processes. Pharmacol Ther. Jan. 1995;65(1):19-46.

Chiappinelli, et al., Reduced DICER1 elicits an interferon response in endometrial cancer cells. Mol Cancer Res. Mar. 2012; 10(3): 316-325.

Bidwell, et al., Silencing of Irf7 pathways in breast cancer cells promotes bone metastasis through immune escape. Nat Med. Aug. 2012;18(8):1224-31.

Lehmann, et al., Identification of human triple-negative breast cancer subtypes and preclinical models for selection of targeted therapies. J Clin Invest. Jul. 2011;121(7):2750-67.

Marisa, et al., Gene expression classification of colon cancer into molecular subtypes: characterization, validation, and prognostic value. PLoS Med. 2013;10(5):e1001453.

(56) References Cited

OTHER PUBLICATIONS

Verhaak, et al., Prognostically relevant gene signatures of high-grade serous ovarian carcinoma. J Clin Invest. Jan. 2013;123(1):517-25.

Mohammad, et al., Polycomb CBX7 promotes initiation of heritable repression of genes frequently silenced with cancer-specific DNA hypermethylation. Cancer Res. Aug. 1, 2009;69(15):6322-30.

Kato, et al., Synergistic in vivo antitumor effect of the histone deacetylase inhibitor MS-275 in combination with interleukin 2 in a murine model of renal cell carcinoma. Clin Cancer Res. Aug. 1, 2007;13(15 Pt 1):4538-46.

Gore, et al., Combined DNA methyltransferase and histone deacetylase inhibition in the treatment of myeloid neoplasms. Cancer Res. Jun. 15, 2006;66(12):6361-9.

Warnault, et al., Chromatin remodeling—a novel strategy to control excessive alcohol drinking. Transl Psychiatry. Feb. 19, 2013;3:e231.

Treppendahl, M., et al., "Preducting response to epigenetic therapy", The Journal of Clinical Investigation, vol. 124, No. 1, pp. 47-55, Jan. 2014.

Chihak, et al., Effects of 5-azacytidine on hepatic polyribosomes and maturation of ribosomal RNA. Acta Biol Med Ger. 1974;33(5-6):859-65.

\* cited by examiner

UP-REGULATED GENE SETS

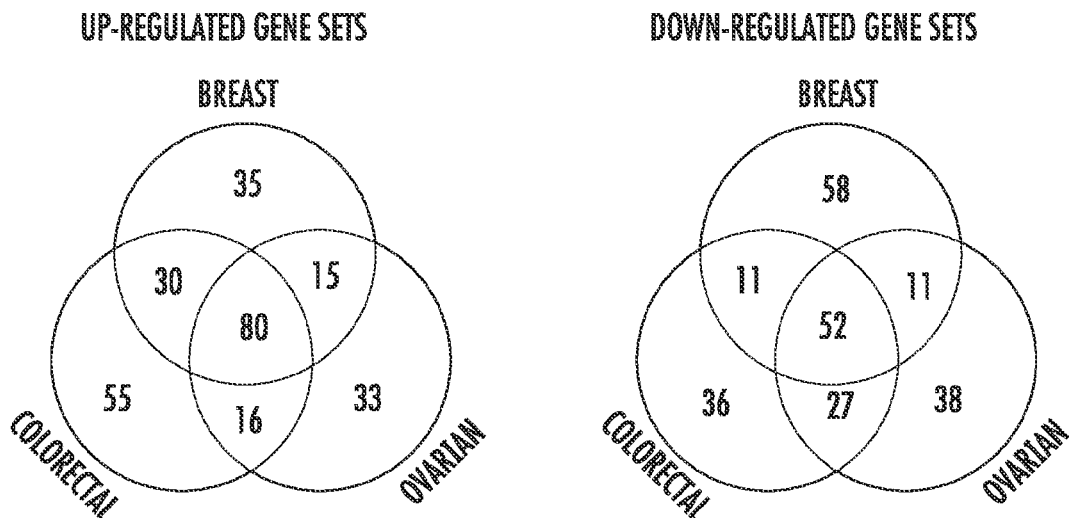

FIG. 1A

DOWN-REGULATED GENE SETS

FIG. 1B

80 COMMON UP-REGULATED GENE SETS TO 3 CANCER TYPES

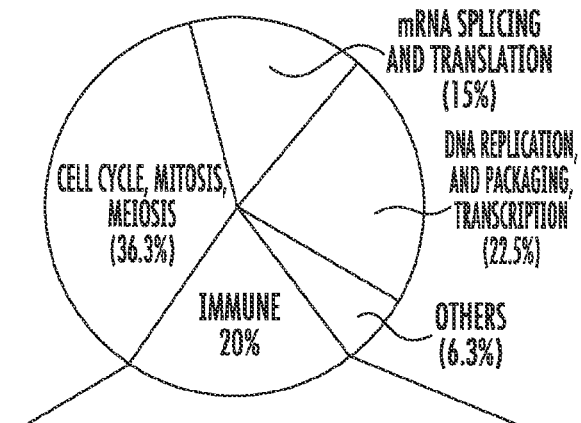

52 COMMON DOWN-REGULATED GENE SETS TO 3 CANCER TYPES

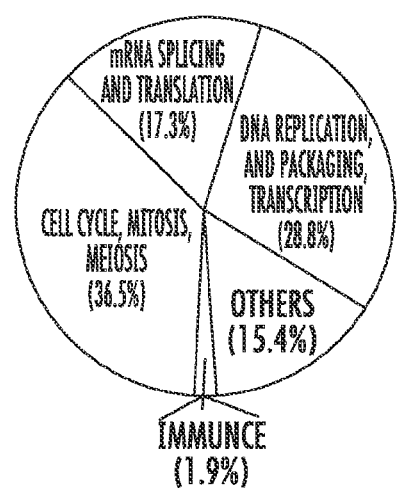

FIG. 1D (1) REACTOME_INTERFERON_GAMMA_SIGNALING
(2) REACTOME_INTERFERON_ALPHA_BETA_SIGNALING
(3) REACTOME_ANTIVIRAL_MECHANISM_BY_IFN_STIMULATED_GENES | INTERFERON
(4) REACTOME_INTERFERON_SIGNALING
(5) REACTOME_NEGATIVE_REGULATORS_OF_RIG_I_MDA5_SIGNALING
(6) KEGG_GRAFT_VERSUS_HOST_DISEASE
(7) REACTOME_ER_PHAGOSOME_PATHWAY | ANTIGEN PRESENTATION
(8) REACTOME_ANTIGEN_PROCESSING_CROSS_PRESENTATION
(9) REACTOME_CHEMOTOME_RECEPTORS_BIND_CHEMOKINES | CHEMOKINE/CYTOKINE
(10) REACTOME_CYTOKINE_SIGNALING_IN_IMMUNE_SYSTEM
(11) DEFENSE_RESPONSE
(12) RESPONSE_TO_WOUNDING | INFLAMMATION
(13) INFLAMMATORY_RESPONSE
(14) REACTOME_INFLUENZA_LIFE_CYCLE | INFLUENZA
(15) REACTOME_INFLUENZA_VIRAL_RNA_TRANSCRIPTION_AND_REPLICATION

FIG. 1C

UP-REGULATED GSEA GENE SET
FOR EACH CANCER TYPE

|  | BREAST | COLORECTAL | OVARIAN |
|---|---|---|---|
| TOTAL GENE SET NUMBER | 160 | 181 | 144 |
| IMMUNE-RELATED GENE SET NUMBER | 27 | 26 | 45 |
| IMMUNE-RELATED GENE SET (% OF TOTAL) | 16.9% | 14.4% | 31.3% |

FIG. 1F

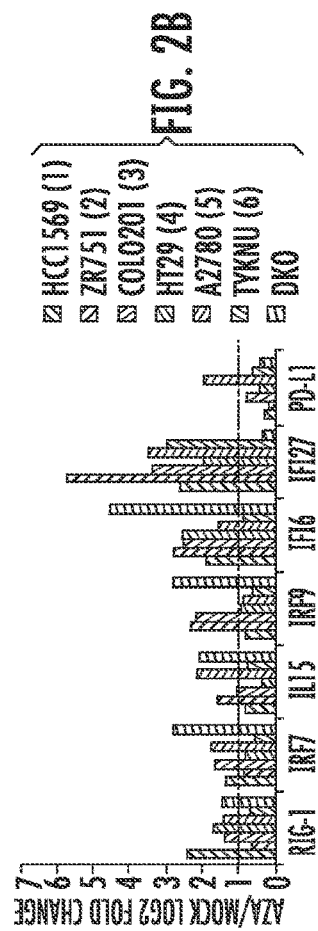
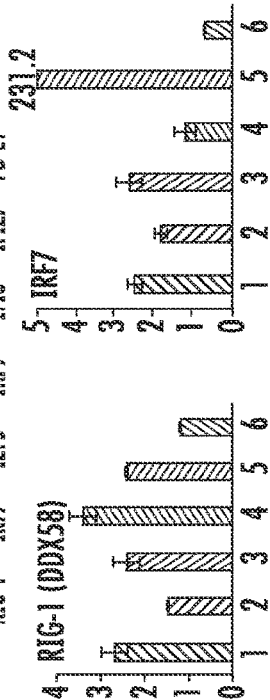
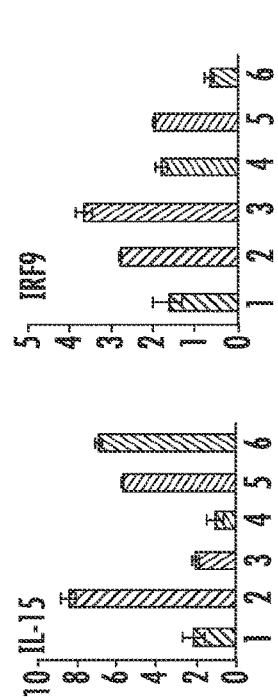
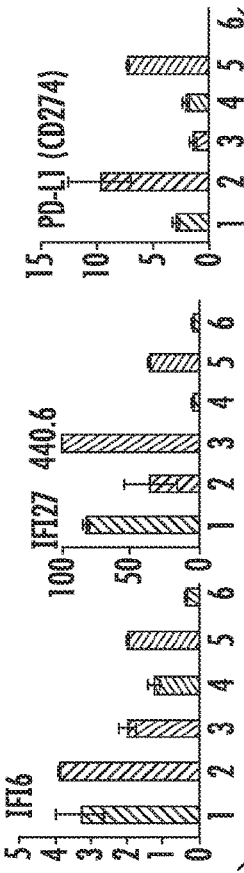
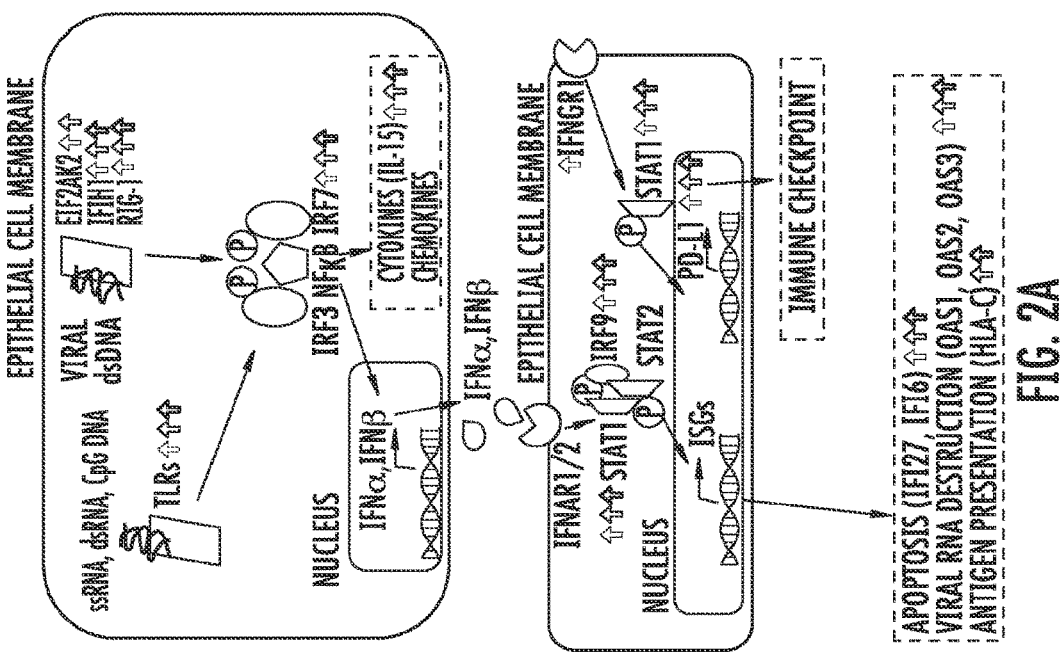

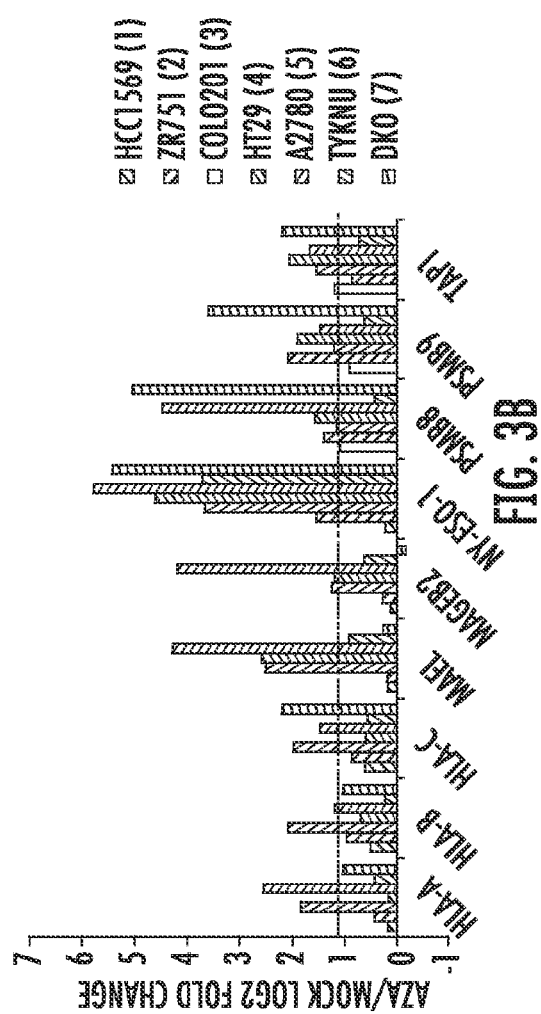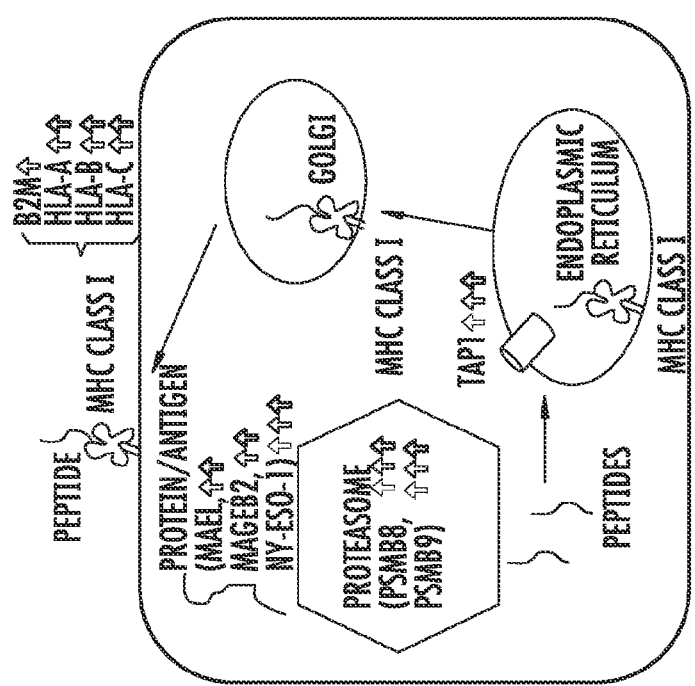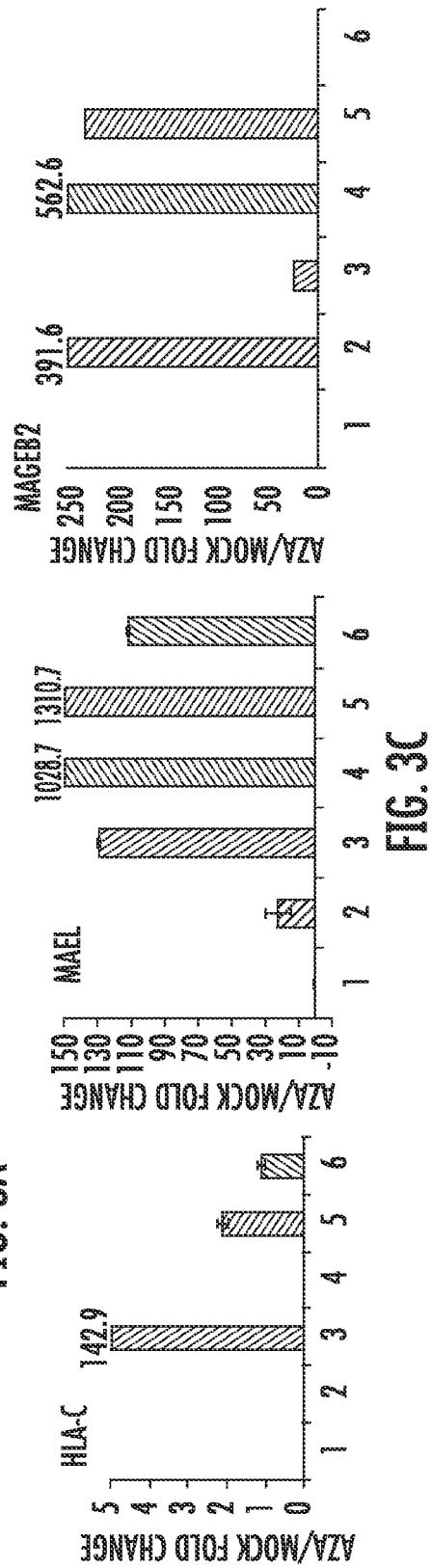
FIG. 3A
FIG. 3B
FIG. 3C

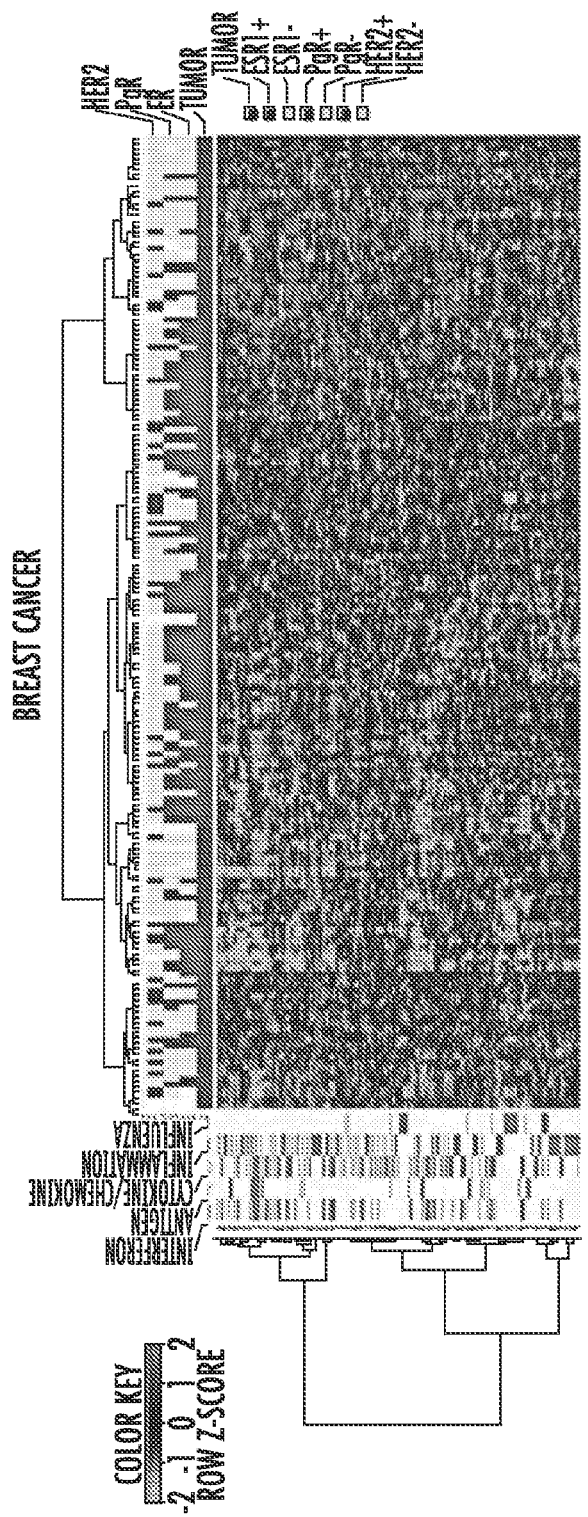

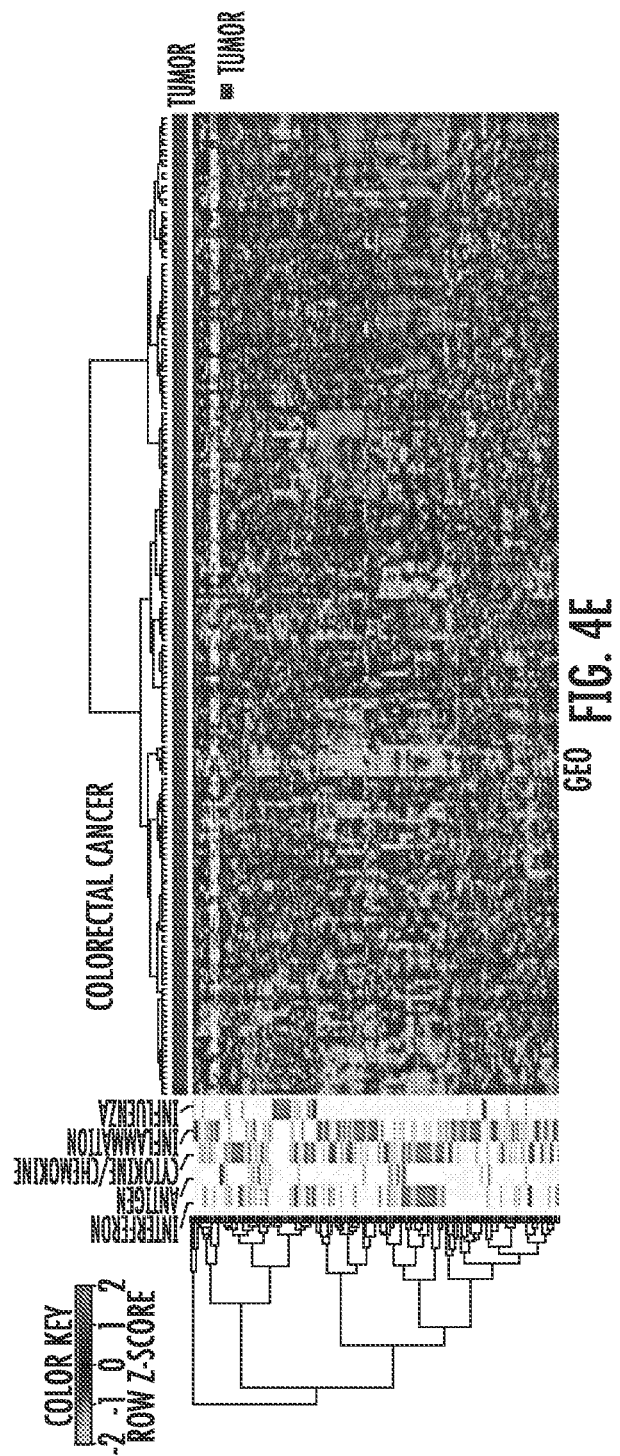

|  | UP-REGULATED | | DOWN-REGULATED | |
|---|---|---|---|---|
|  | BREAST | COLORECTAL | BREAST | COLORECTAL |
| TOTAL ENRICHED GENE SET NUMBER | 101 | 469 | 37 | 202 |
| IMMUNE GENE SET NUMBER | 33 | 56 | 4 | 22 |
| IMMUNE GENE SET (% OF TOTAL) | 32.7 | 11.9 | 10.8 | 10.9 |

FIG. 5A

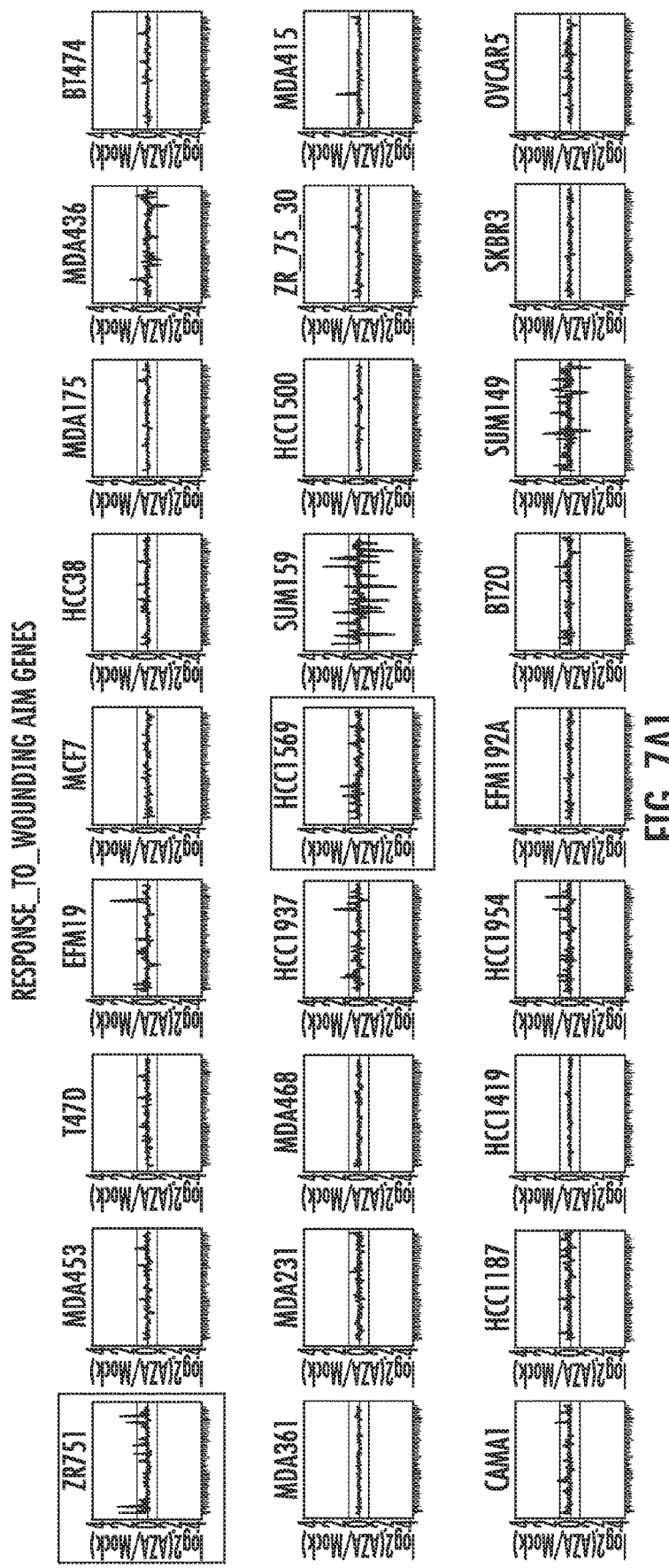
FIG. 7A1
TO FIG. 7A2

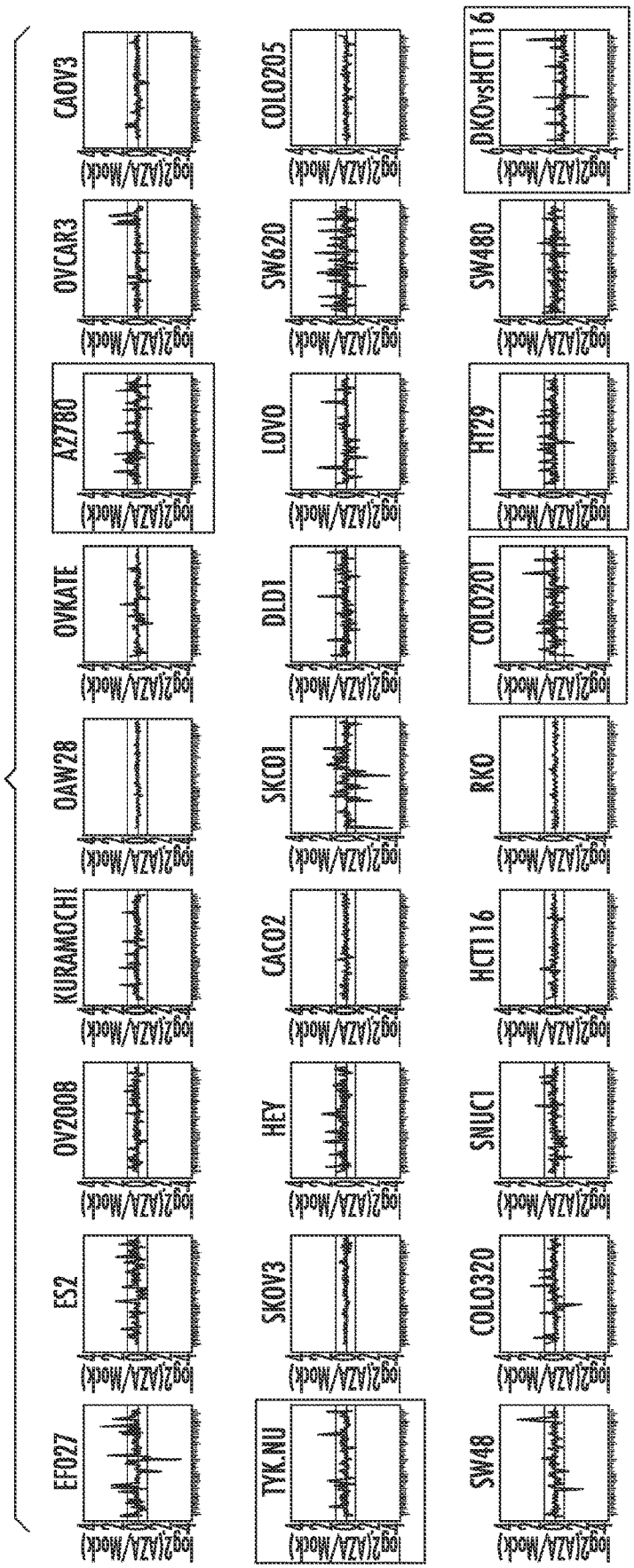
FIG. 7A2

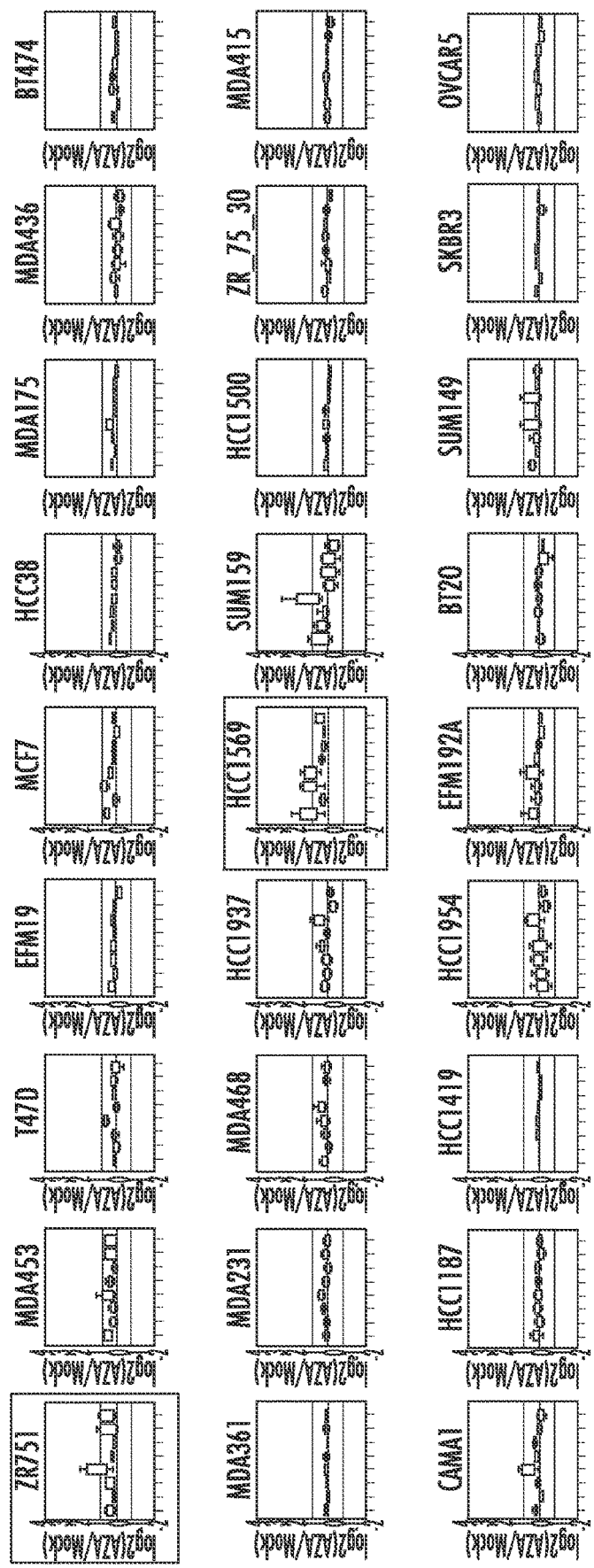

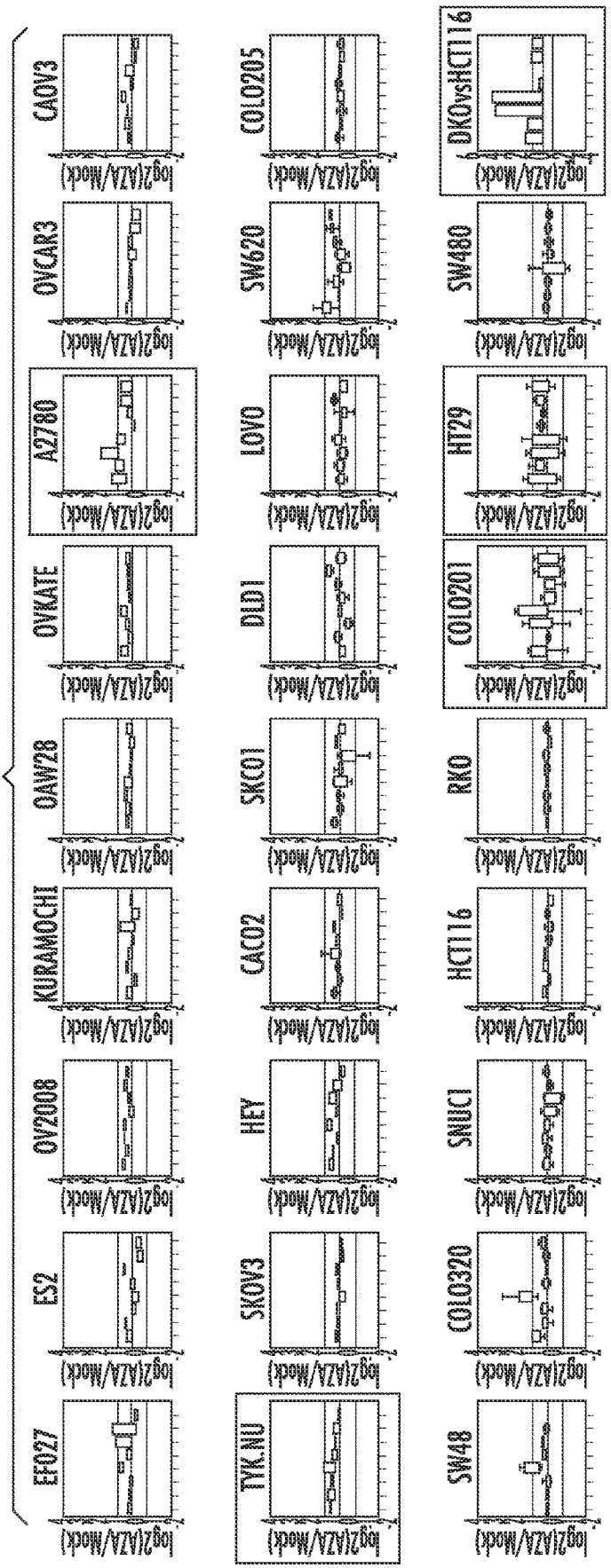
FIG. 7B2

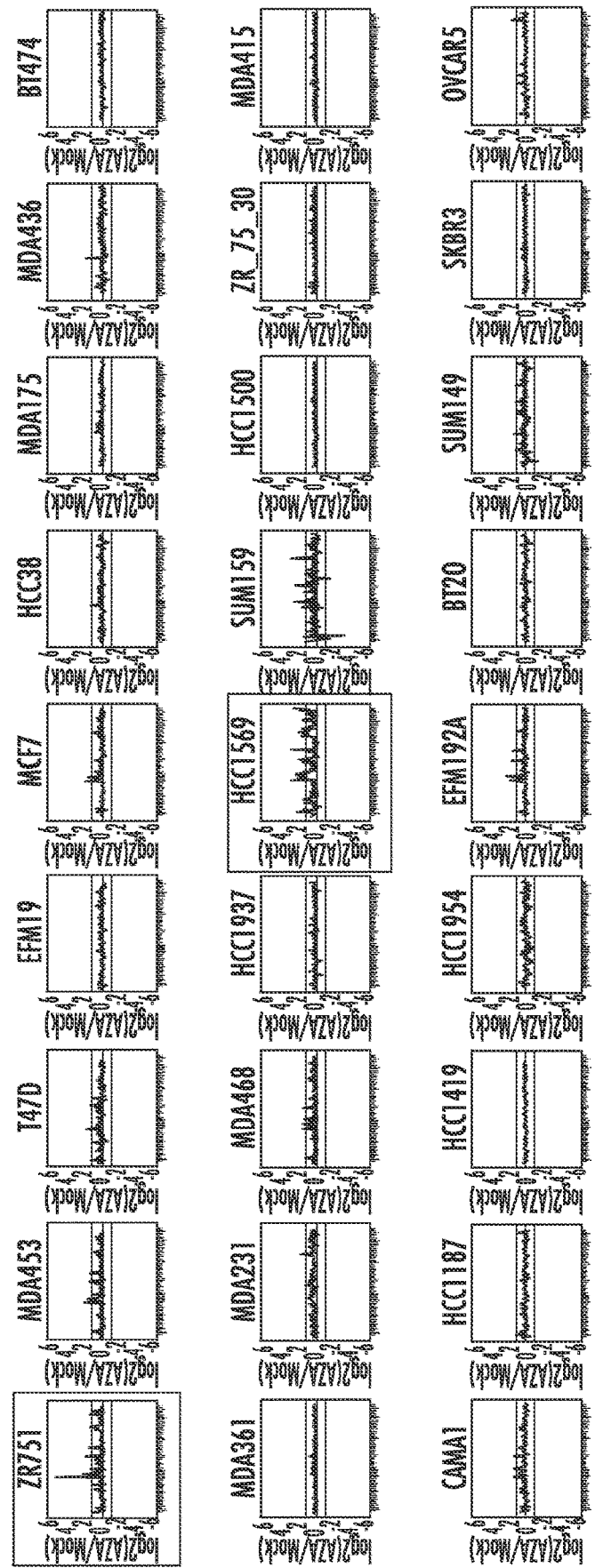

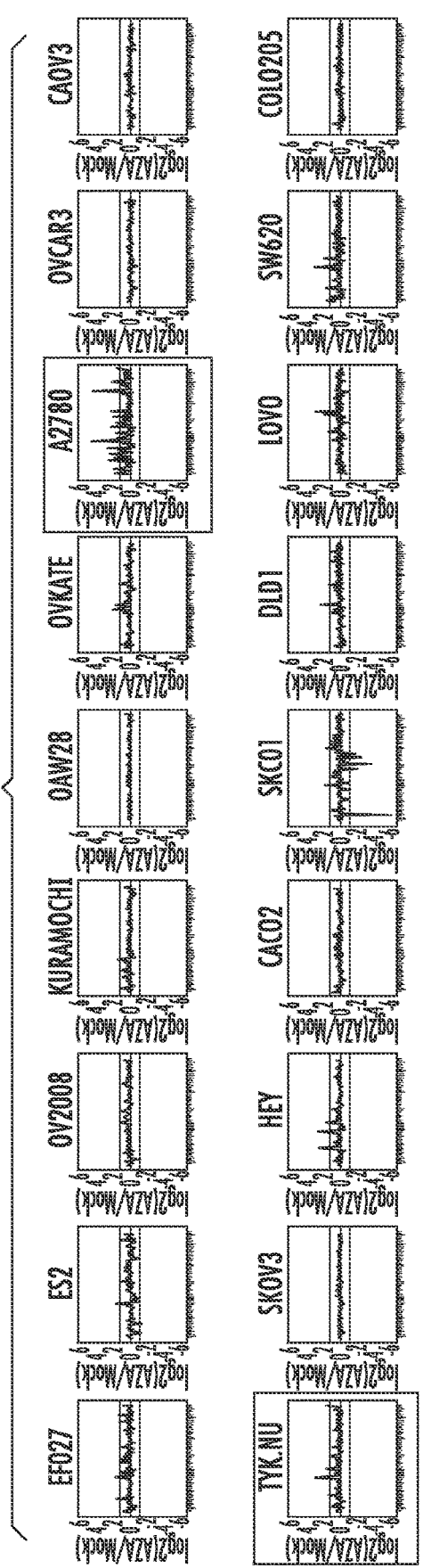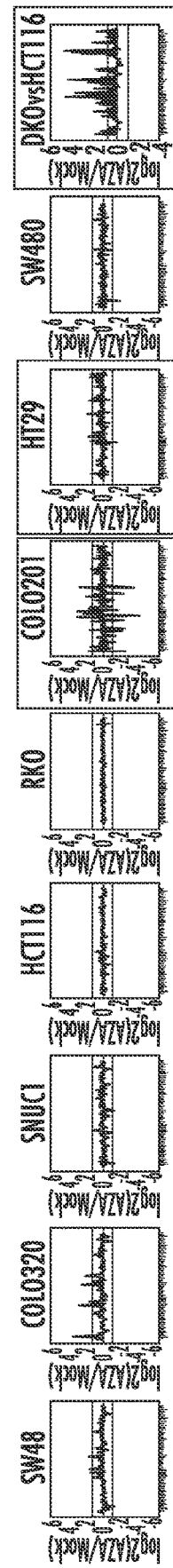
FIG. 7C2

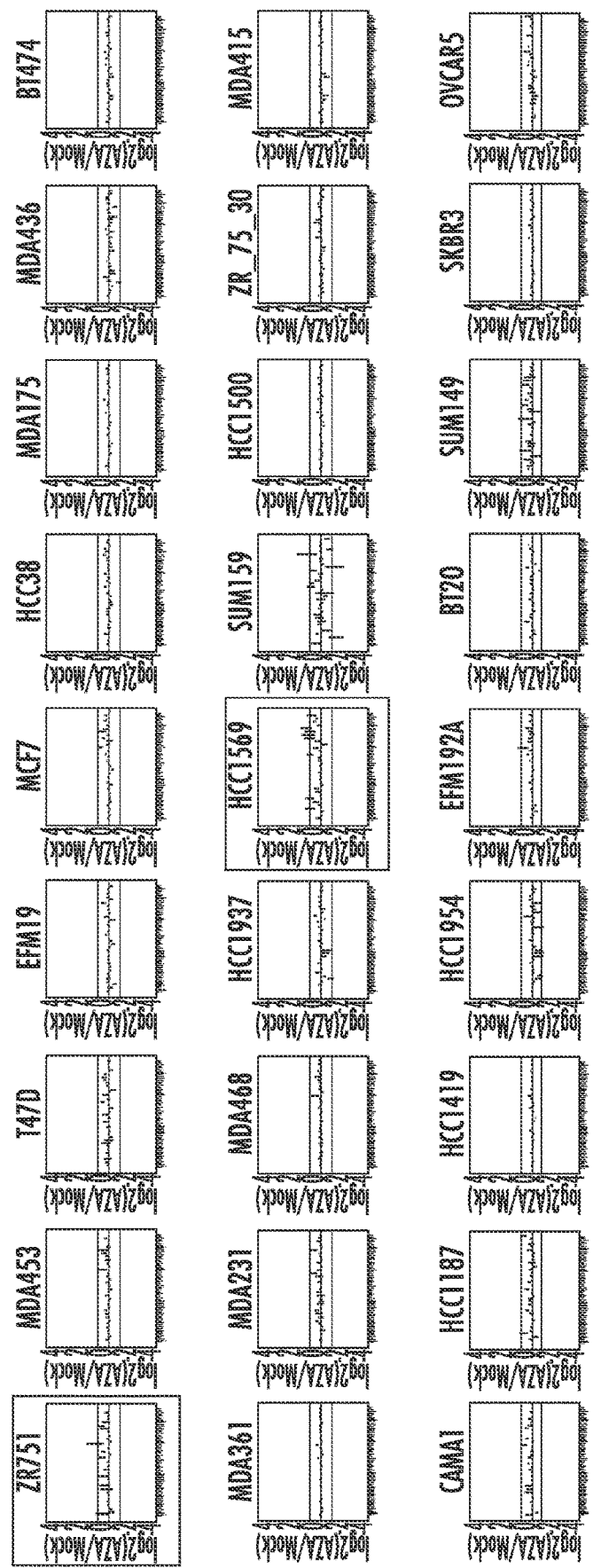

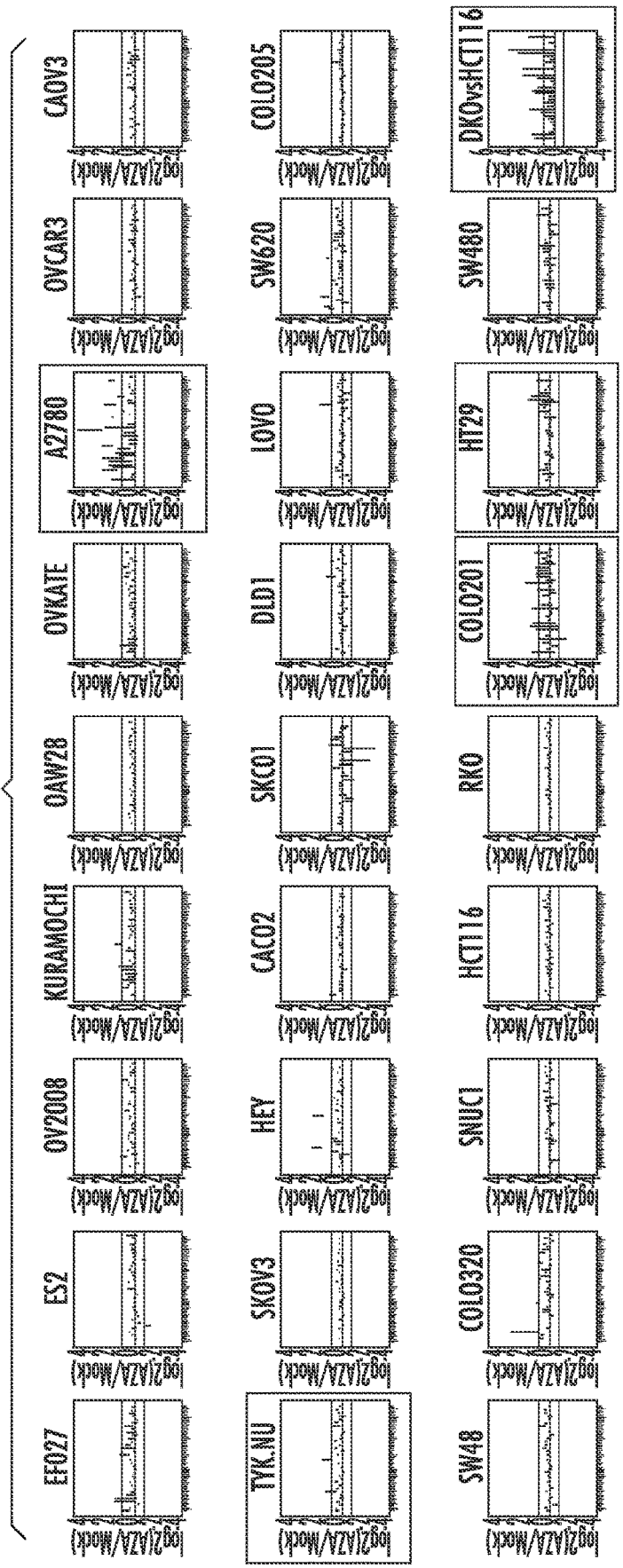
FIG. 7D2

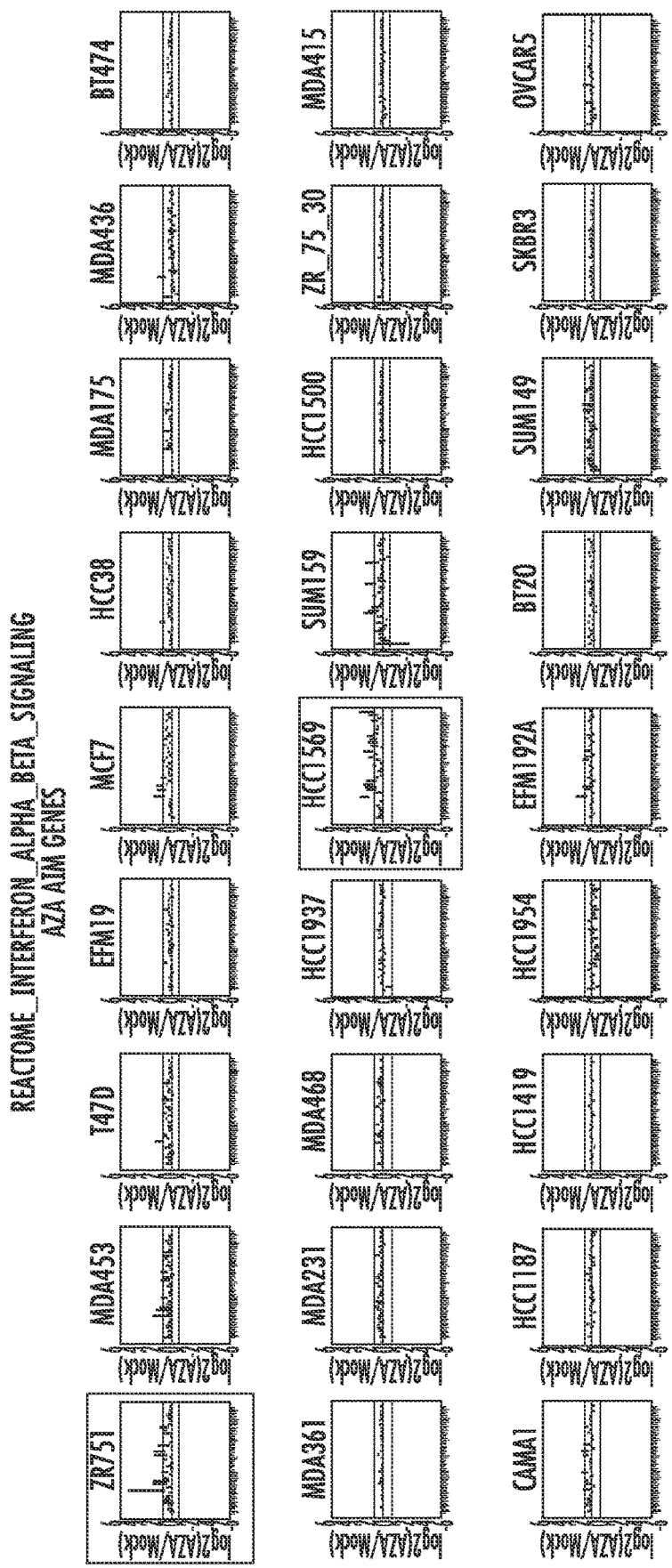
FIG. 7E1
TO FIG. 7E2

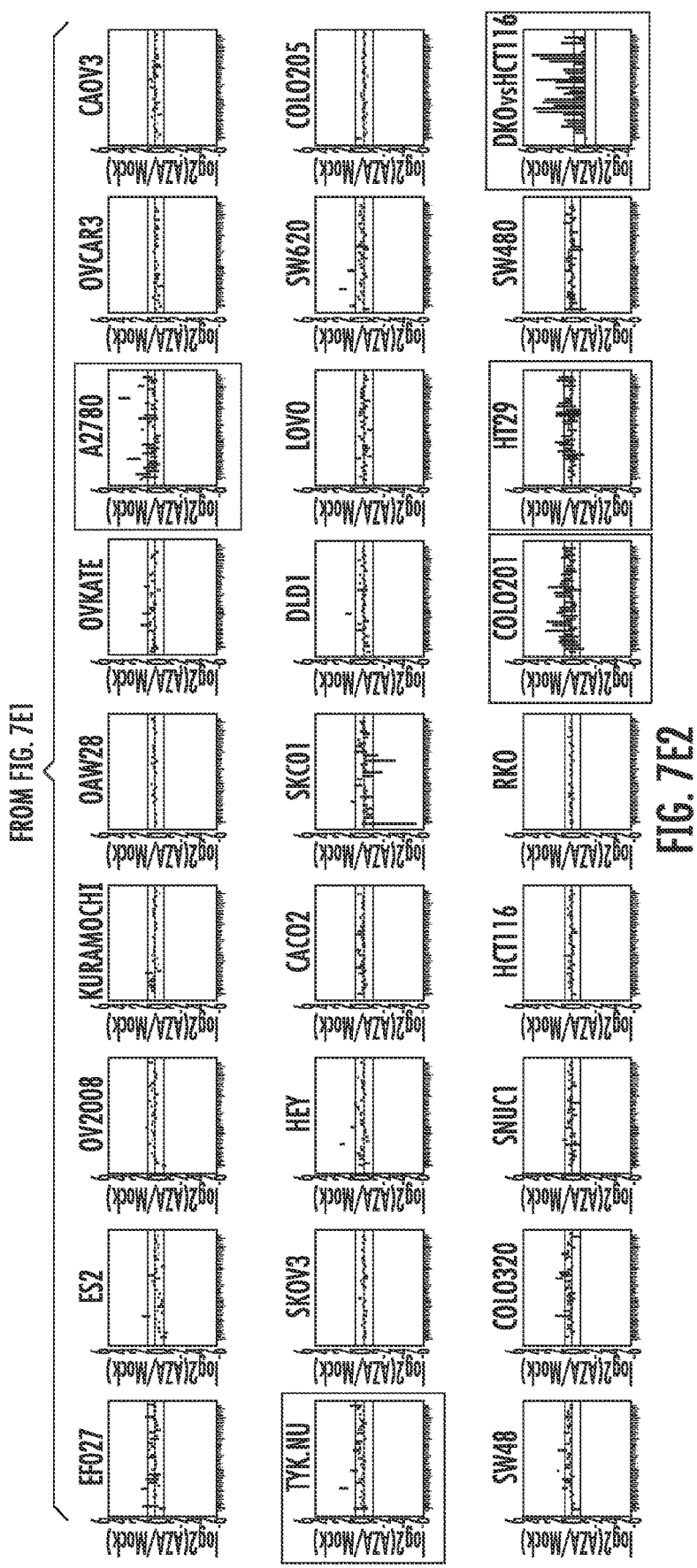
FIG. 7E2

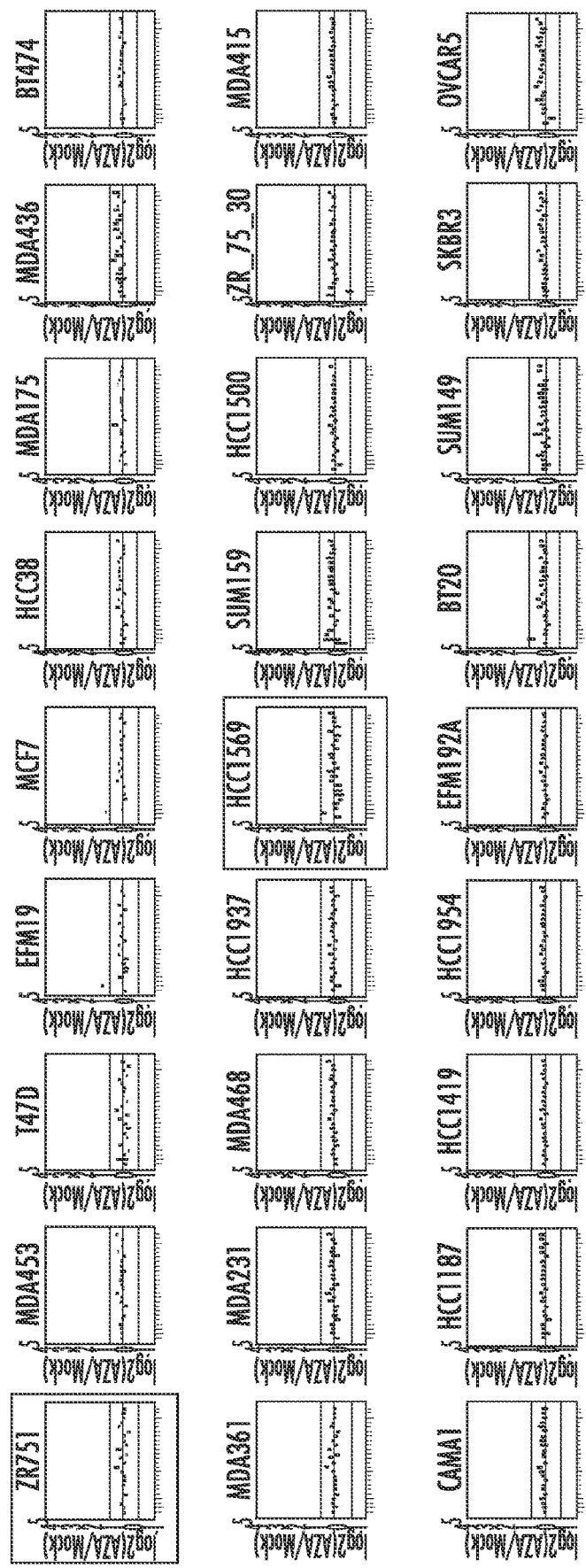

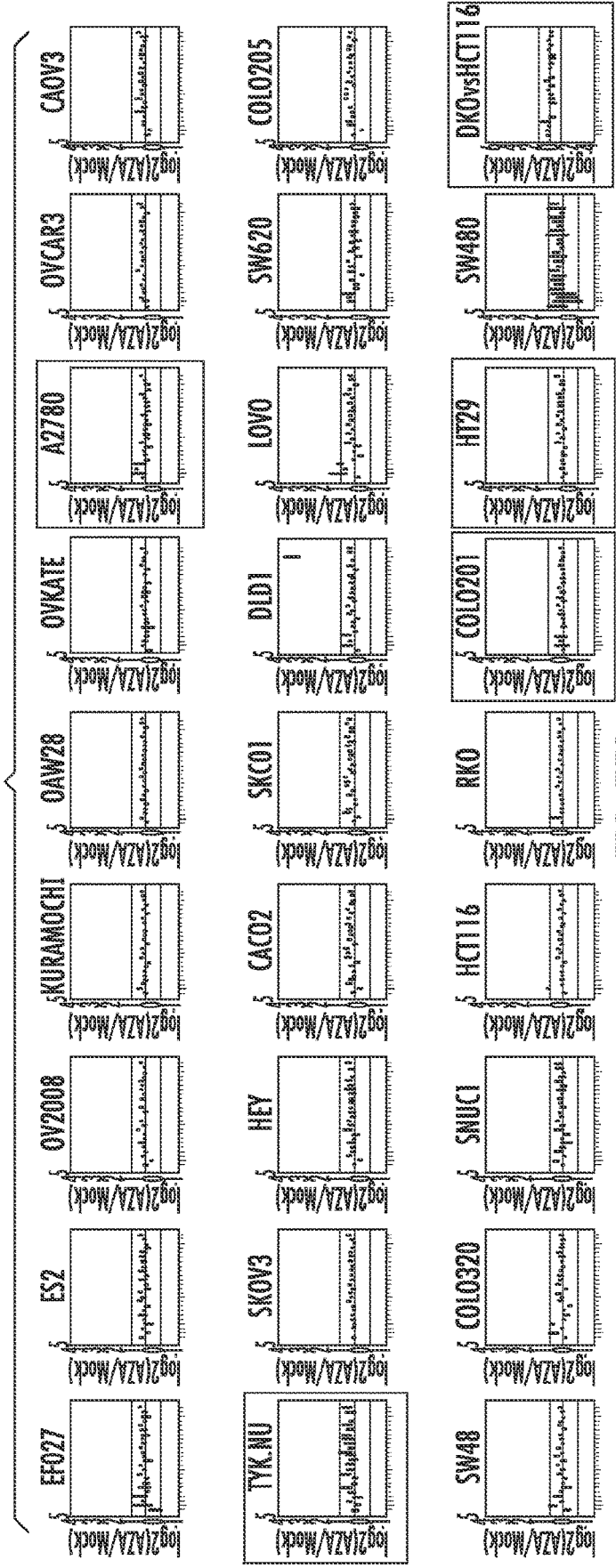
FIG. 7F2

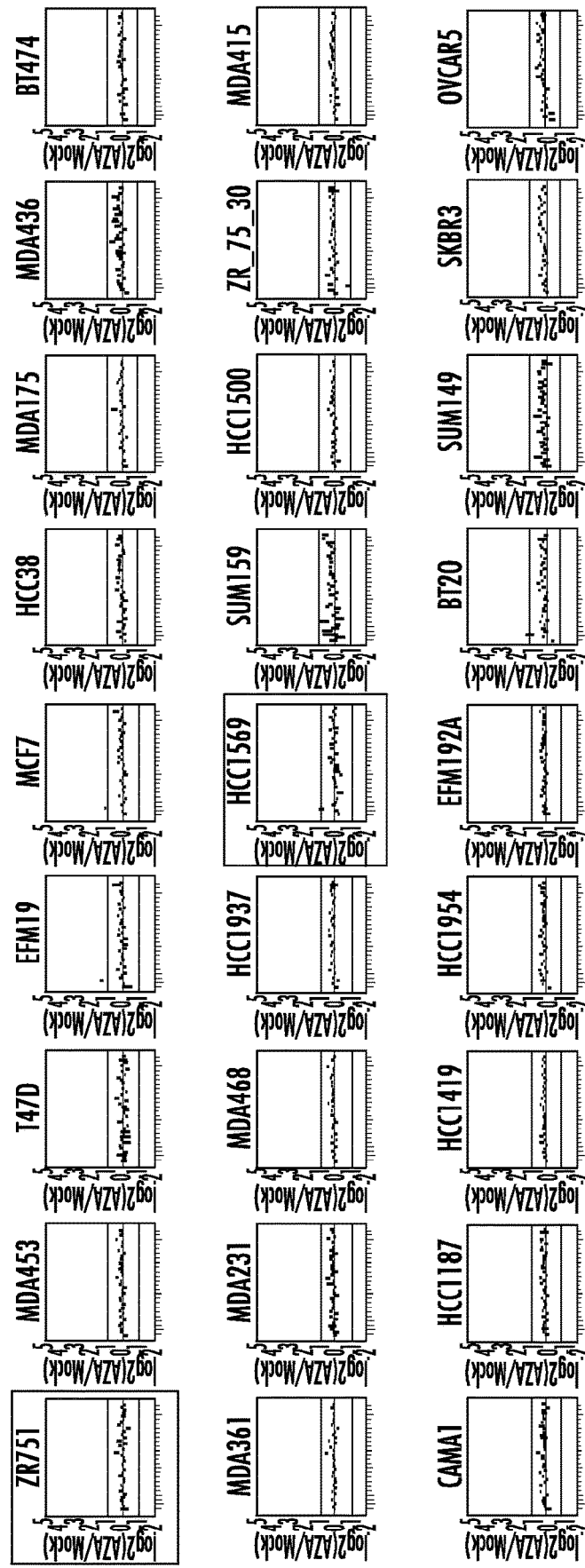
FIG. 7G1
TO FIG. 7G2

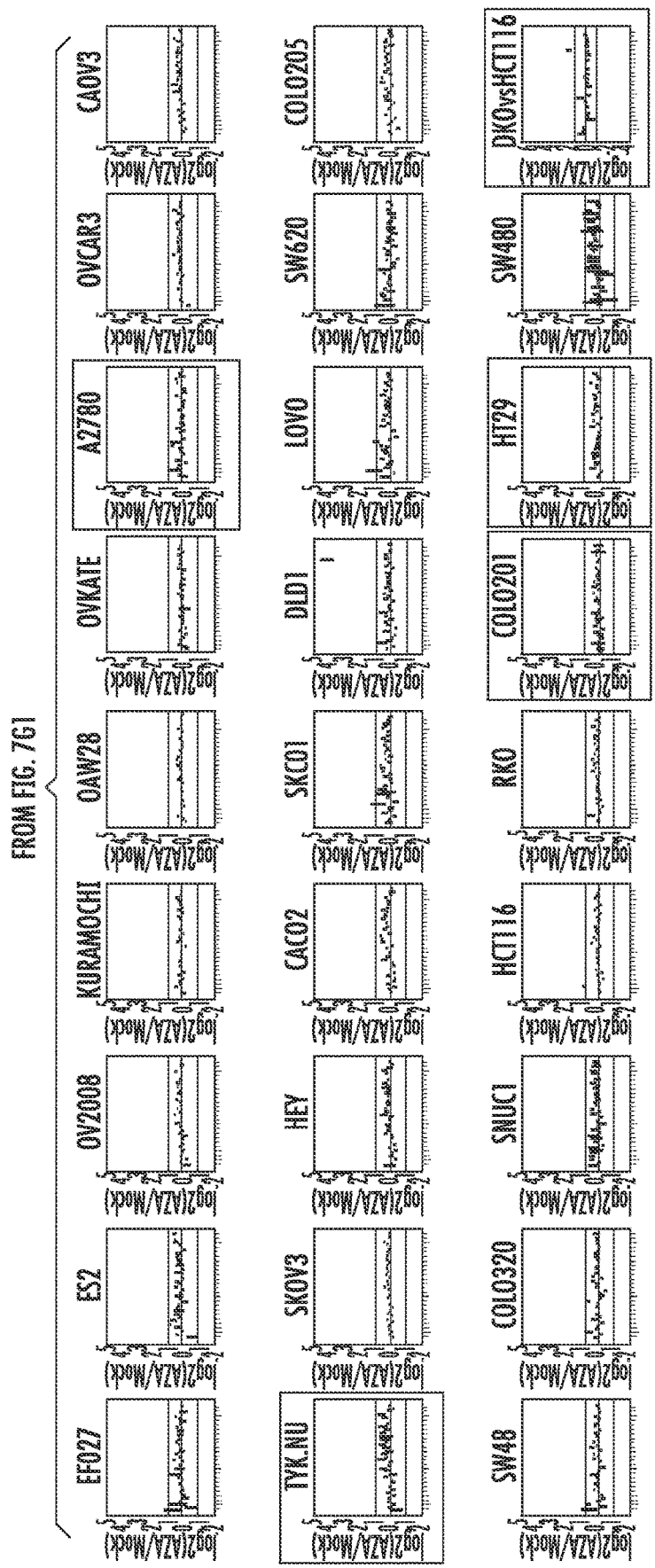
FIG. 7G2

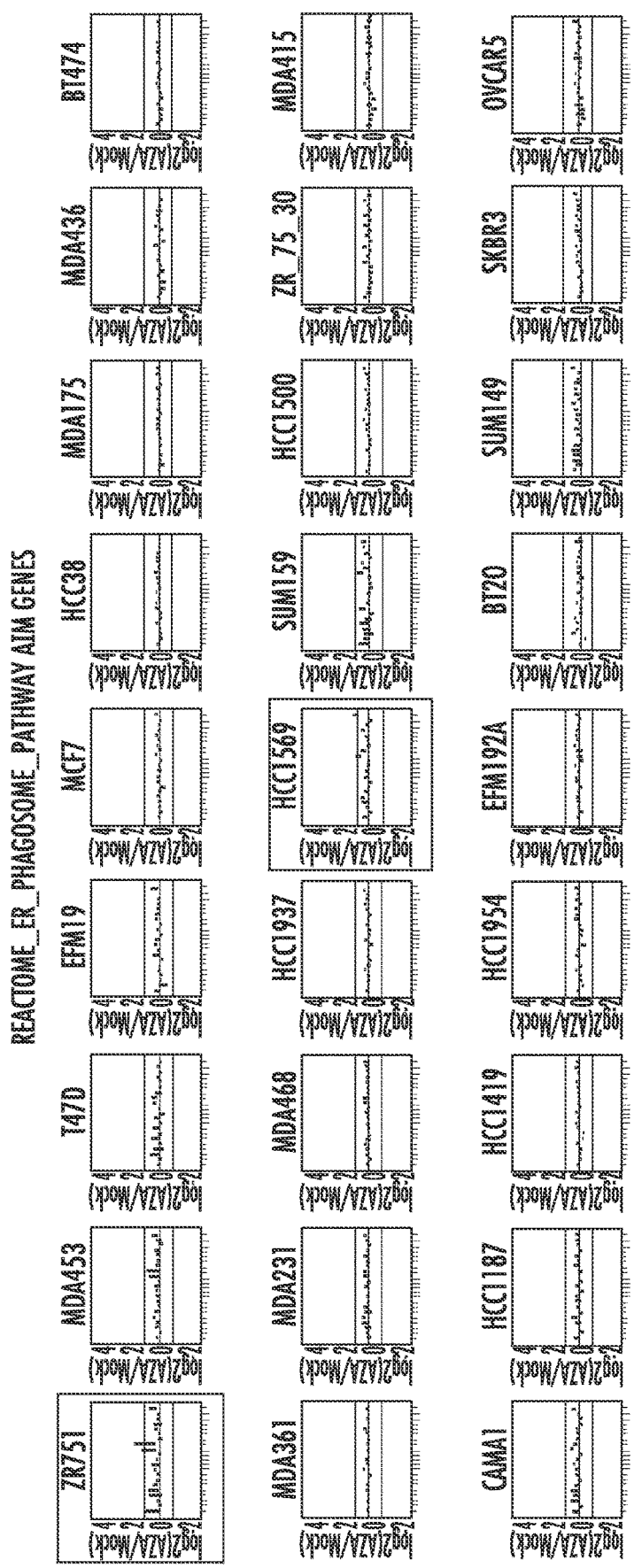
FIG. 7H1
TO FIG. 7H2

FIG. 7H2

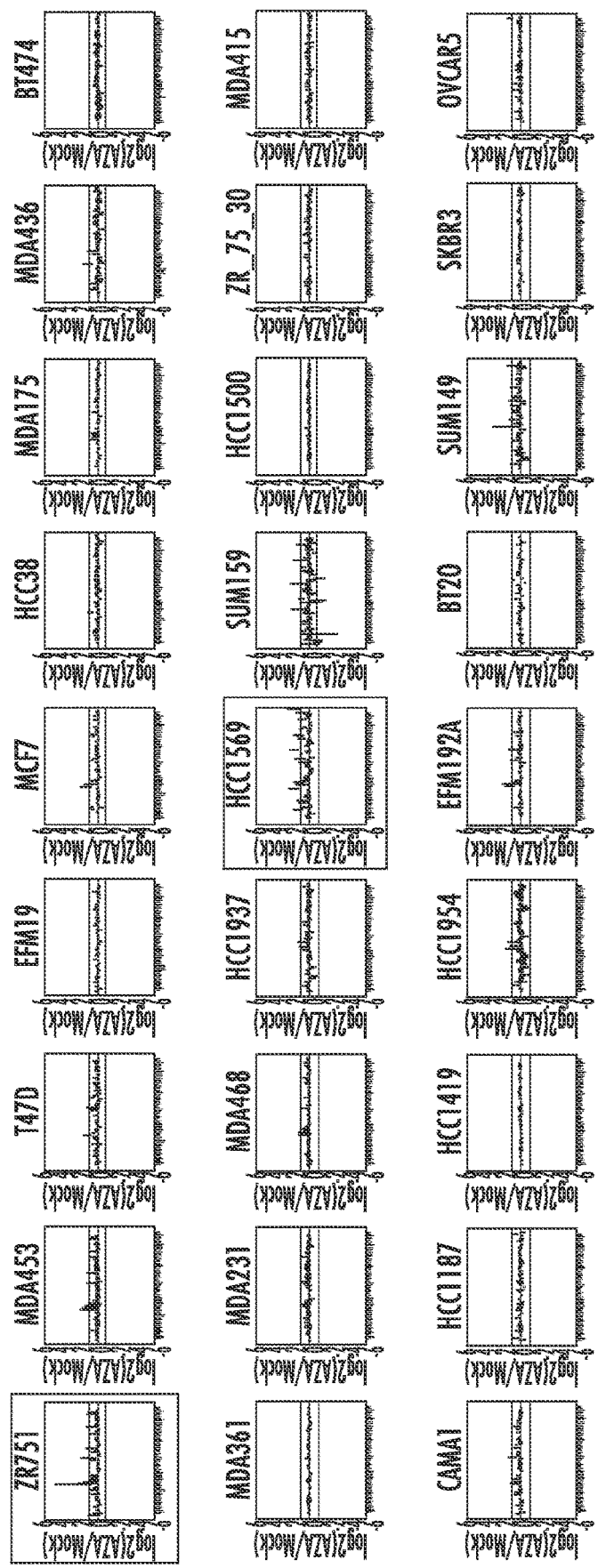
FIG. 7I1

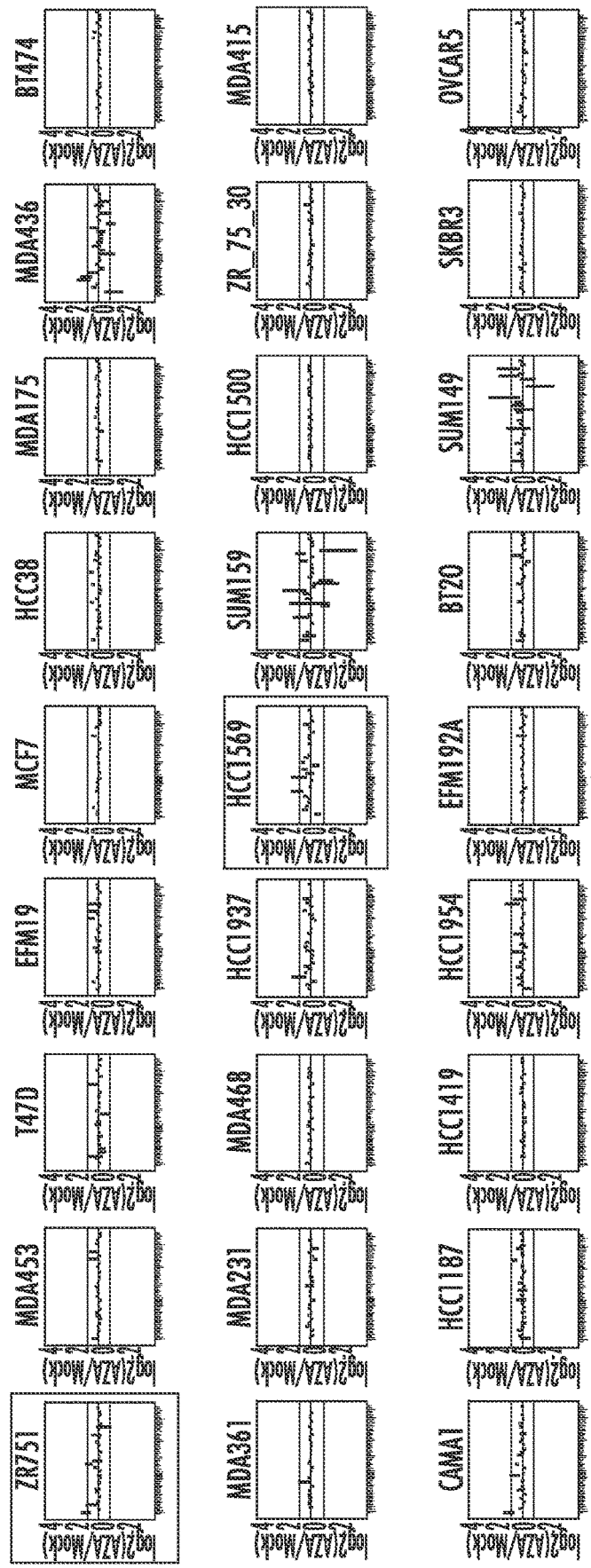

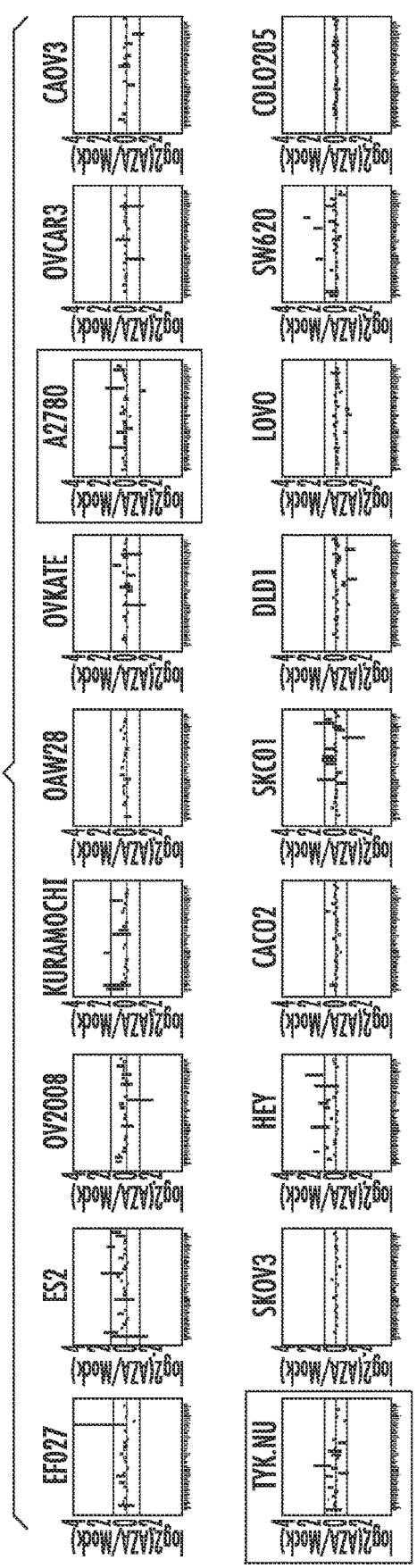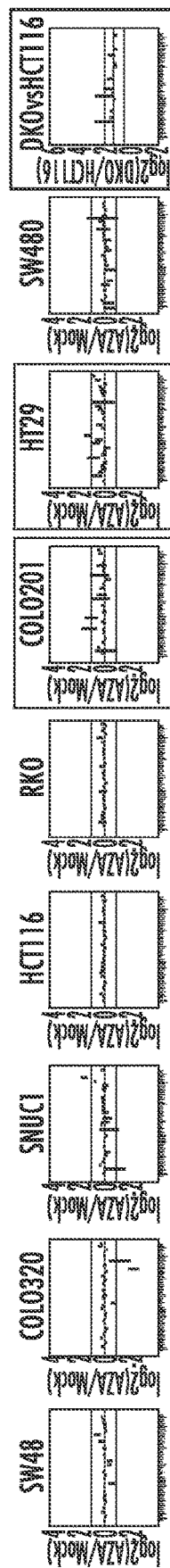
FIG. 7J2

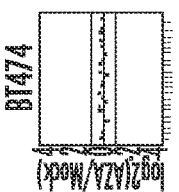
FIG. 7K1

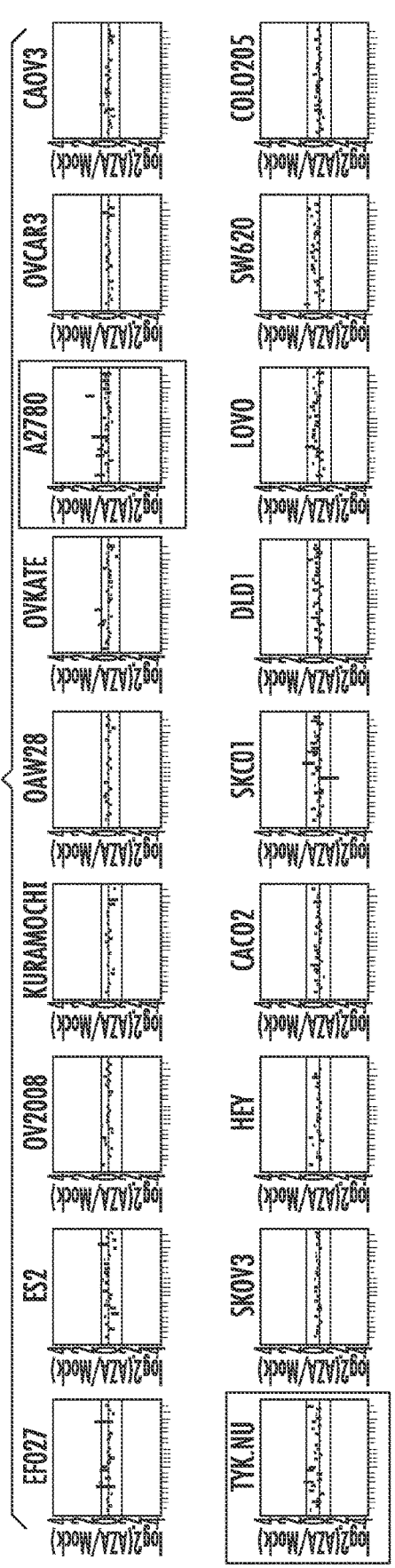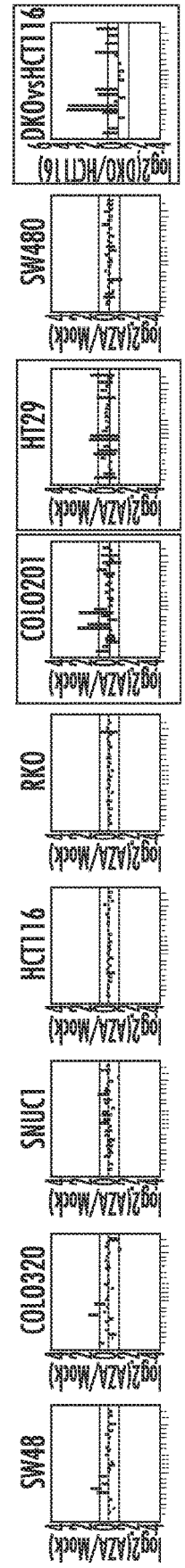
FIG. 7K2

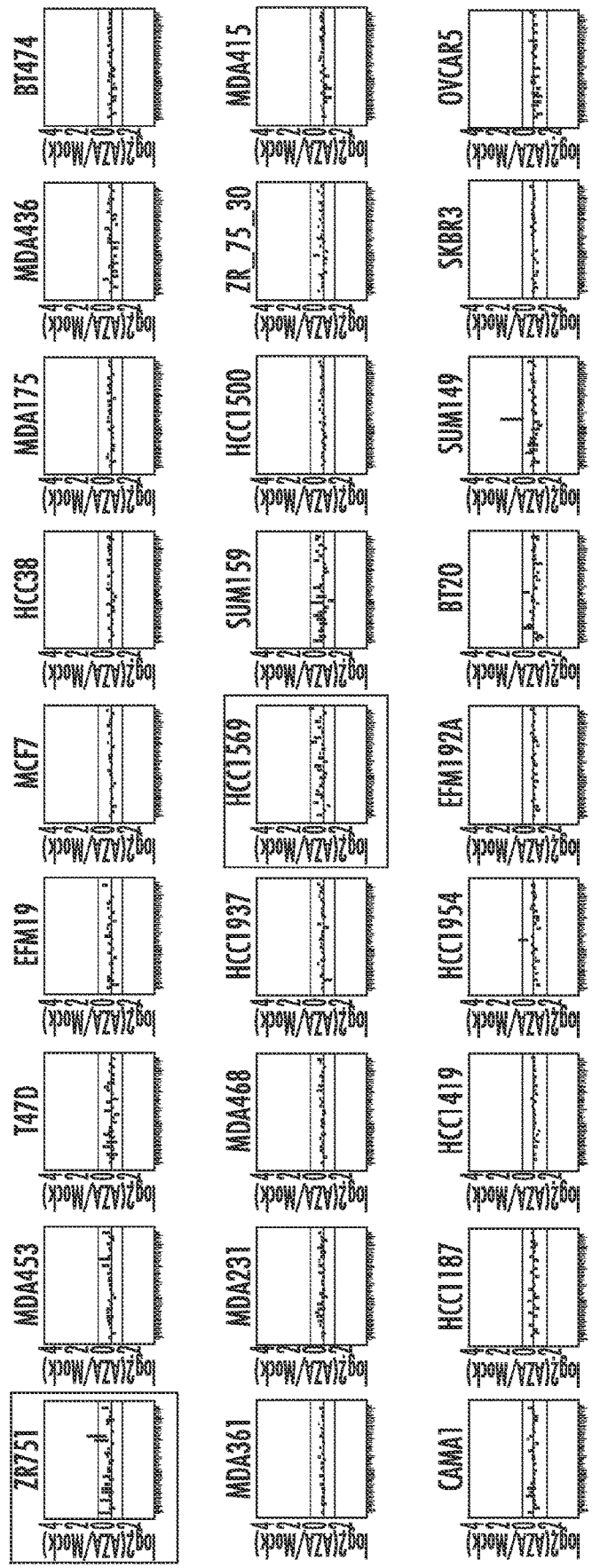
FIG. 7L1

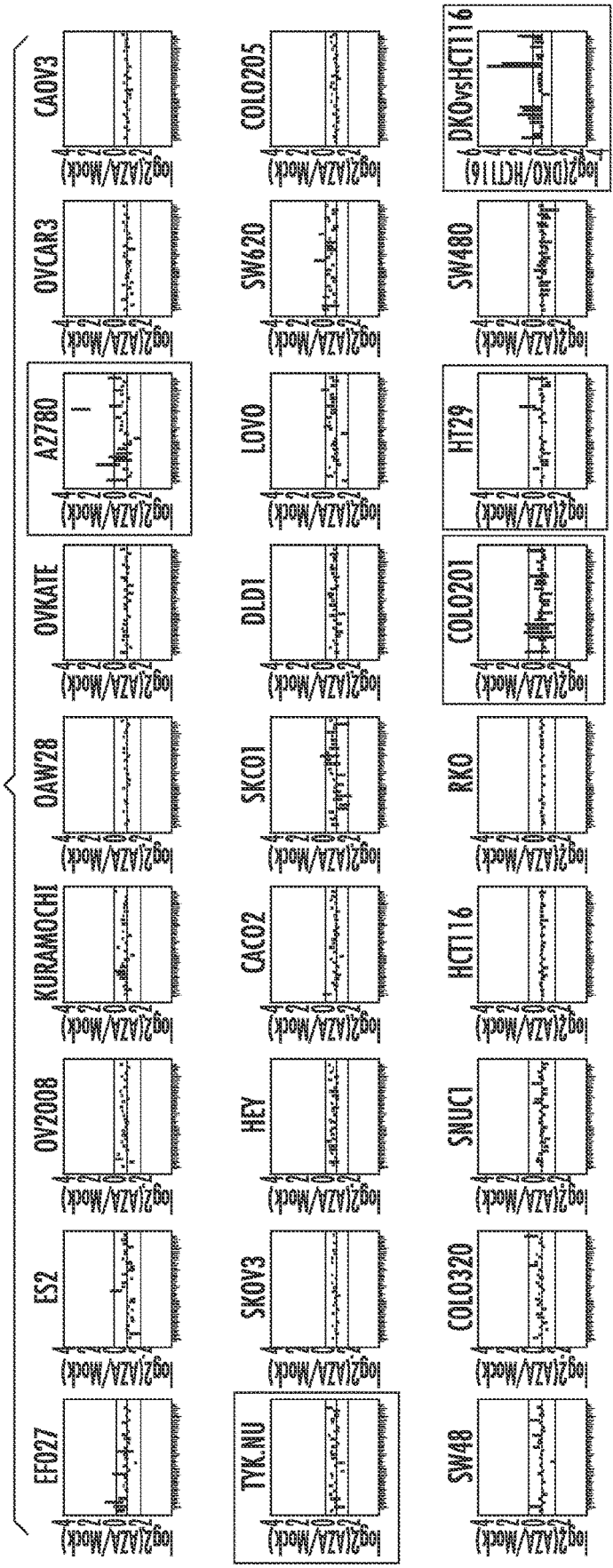
FIG. 7L2

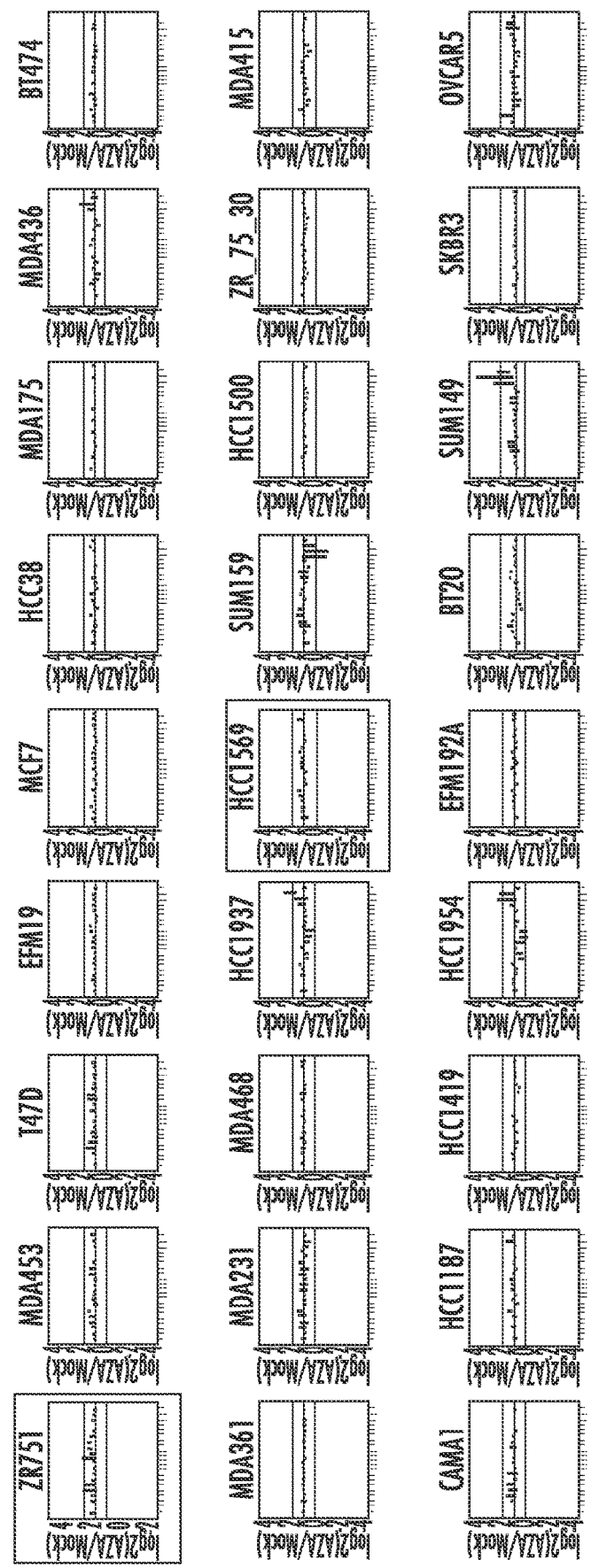

FIG. 7M2

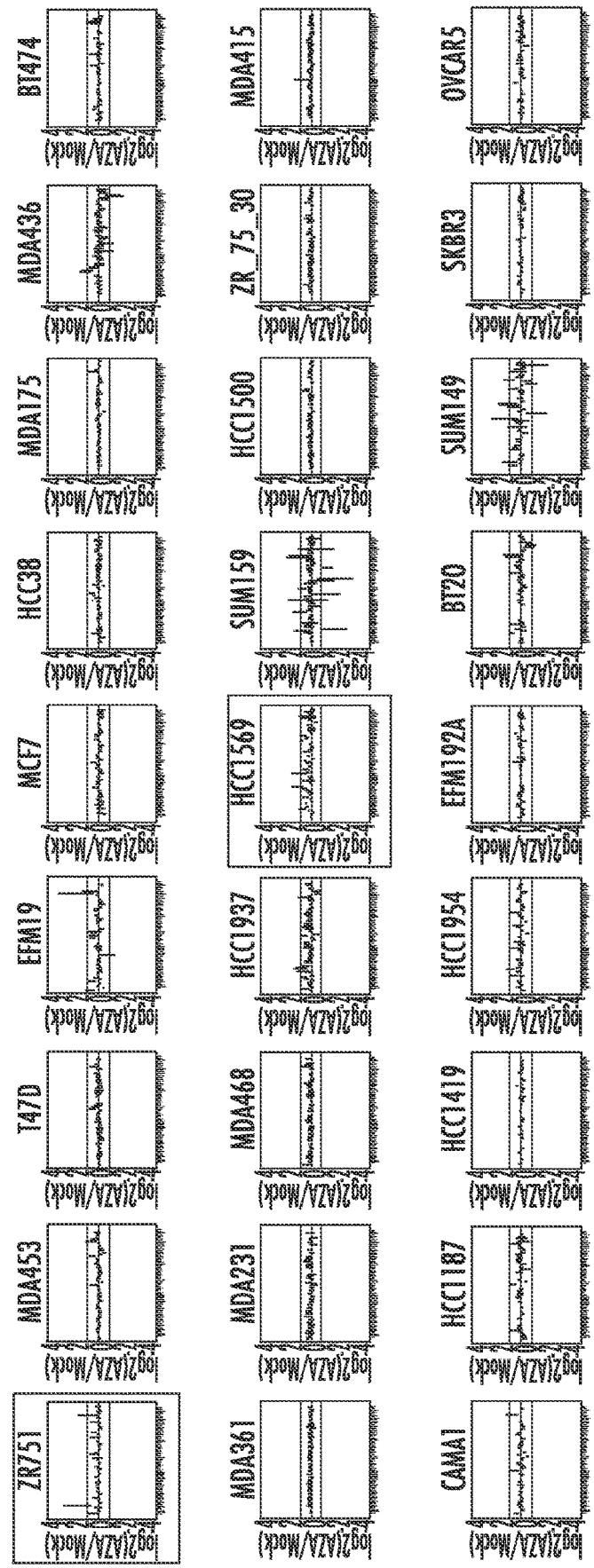

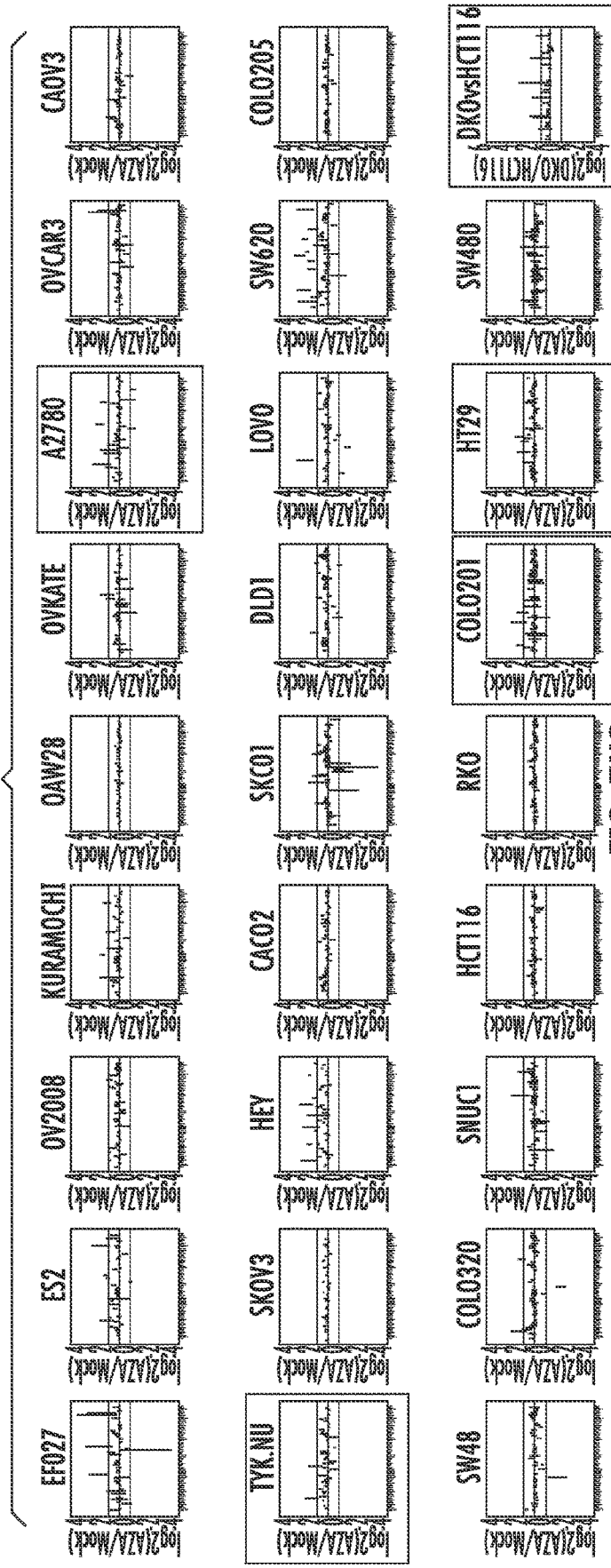
FIG. 7N2

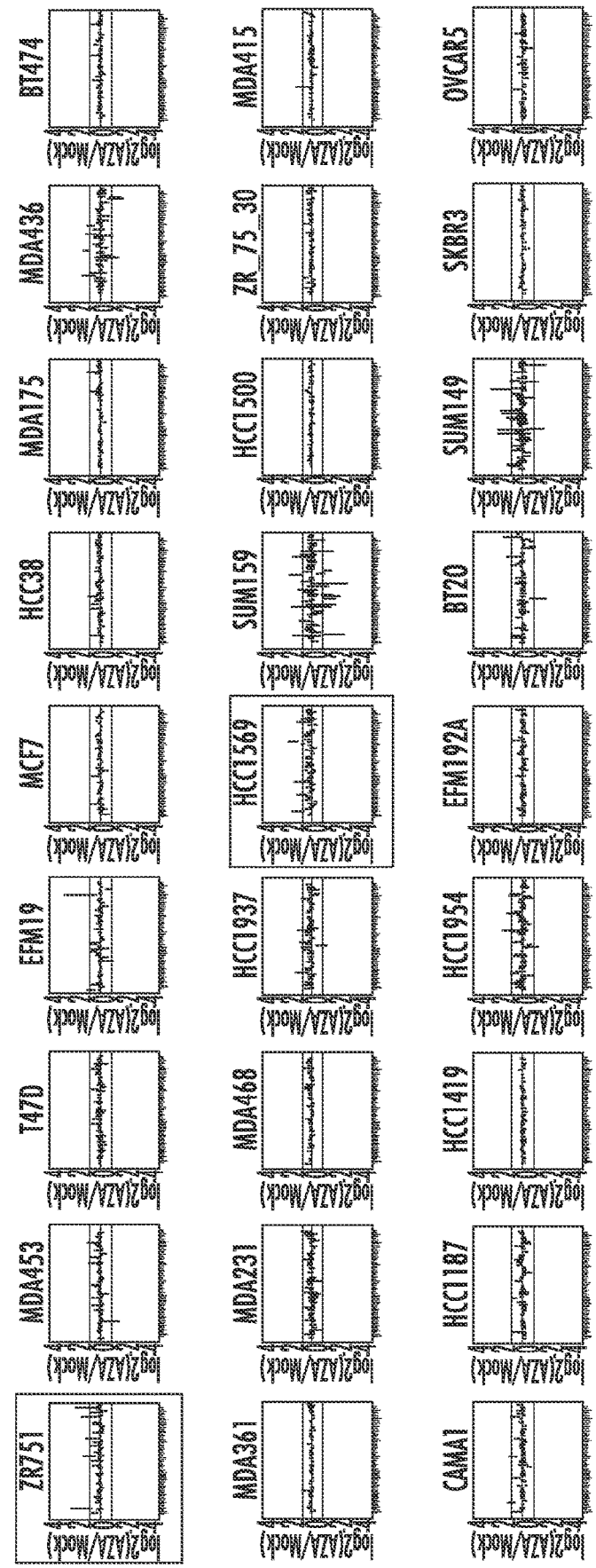

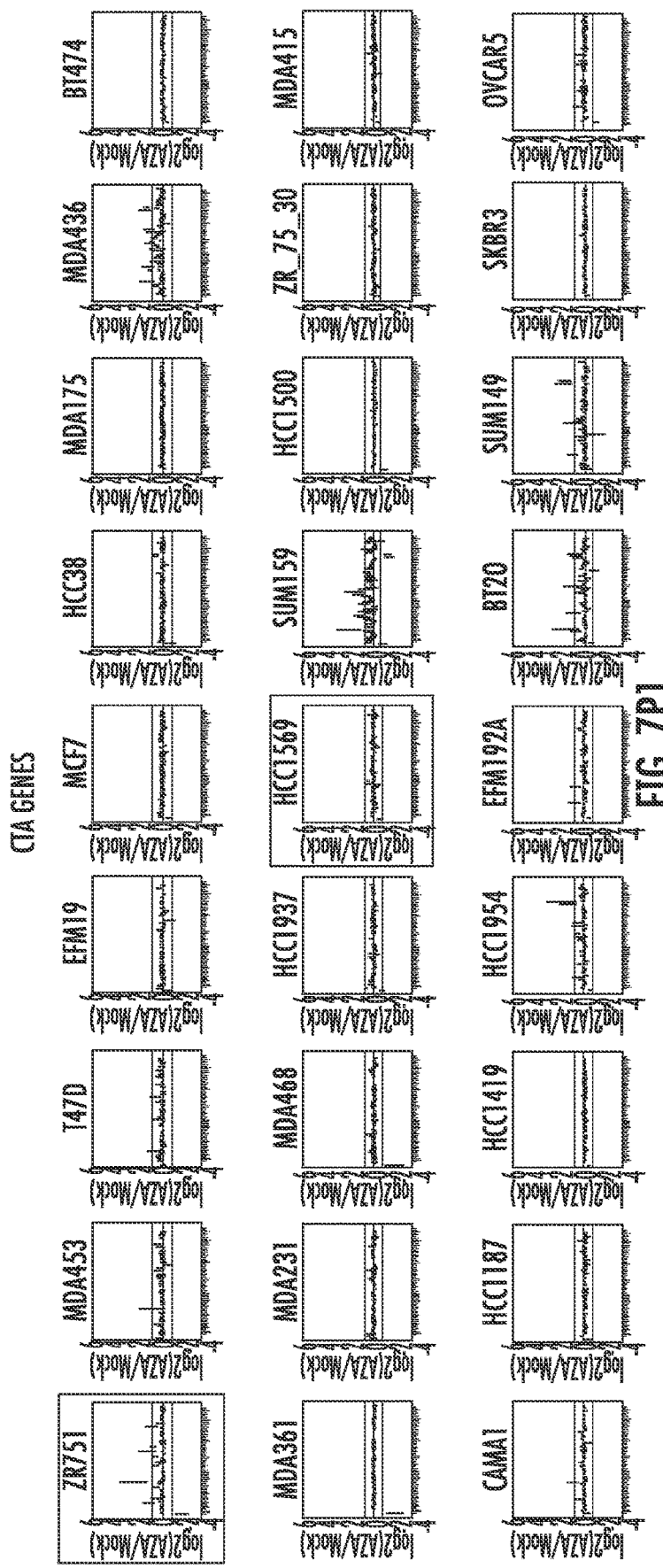
FIG. 7P1
TO FIG. 7P2

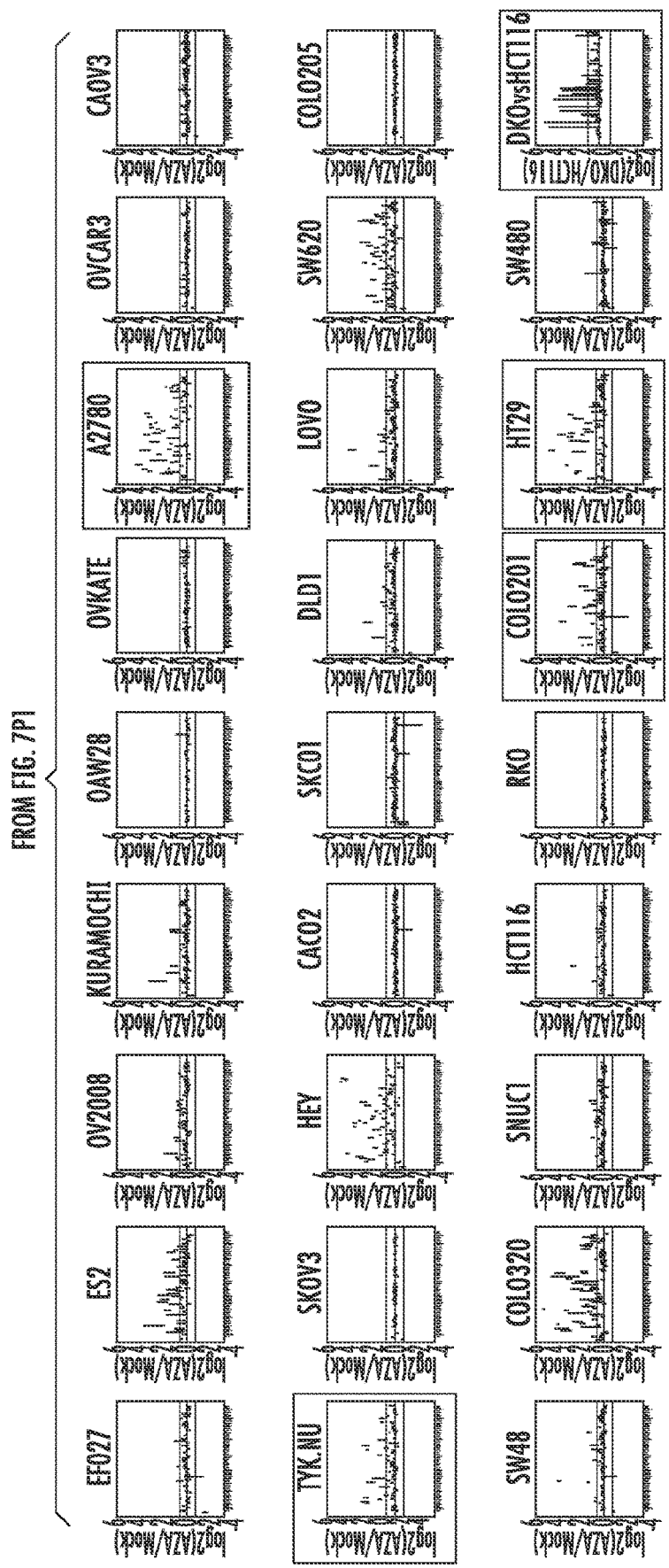

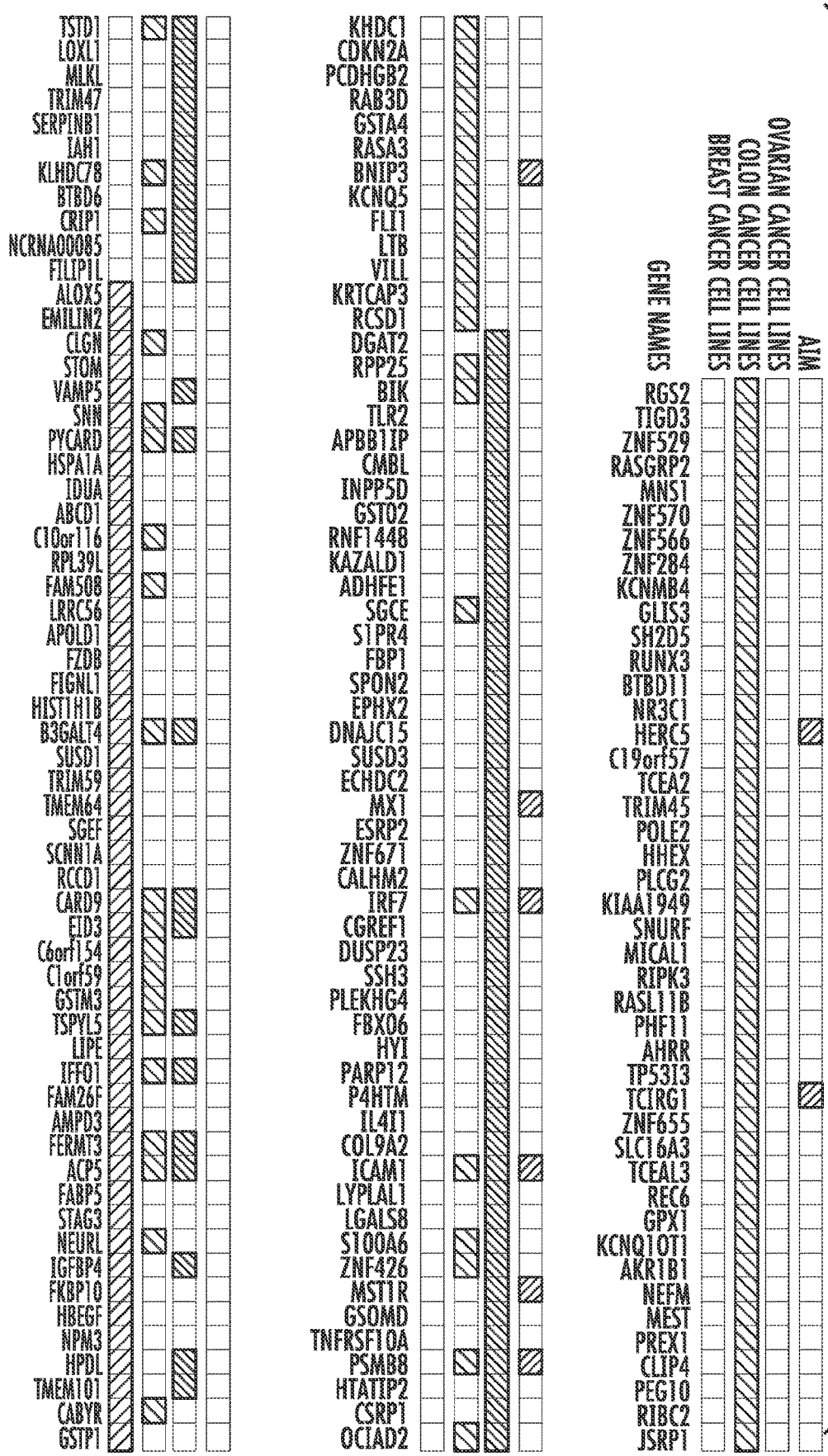

| | DEMETHYLATED & REEXPRESSED AT LEAST 1 OF THE 162 GENE | DEMETHYLATED & REEXPRESSED AT LEAST 1 OF THE 42 IMMUNE GENE | TOTAL NUMBER OF CELL LINE |
|---|---|---|---|
| BREAST | 9 | 8 | 26 |
| COLORECTAL | 7 | 6 | 14 |
| OVARIAN | 10 | 7 | 13 |

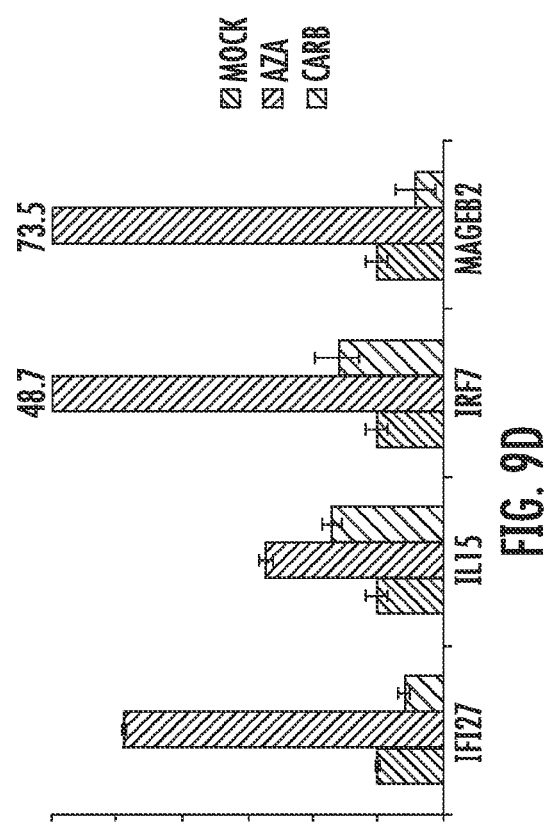
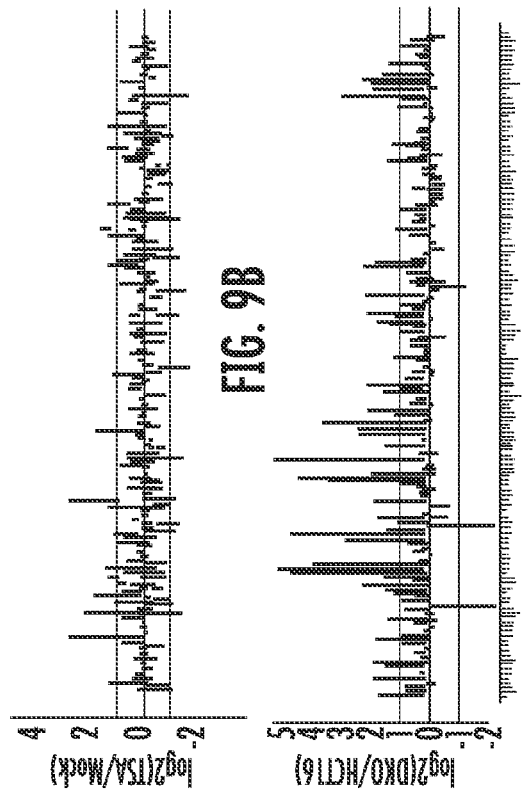
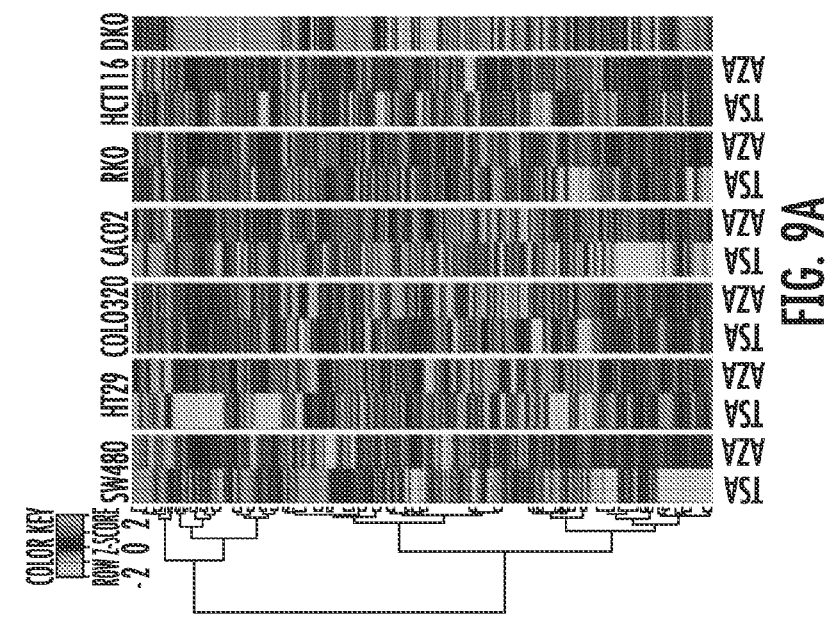

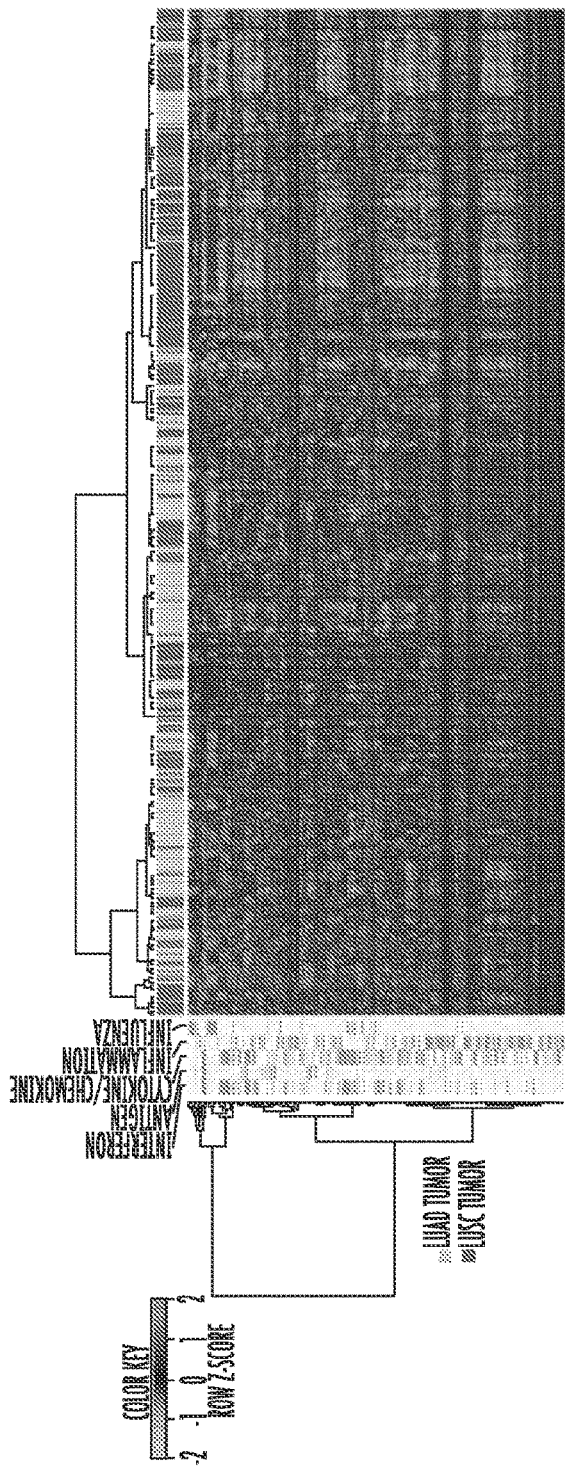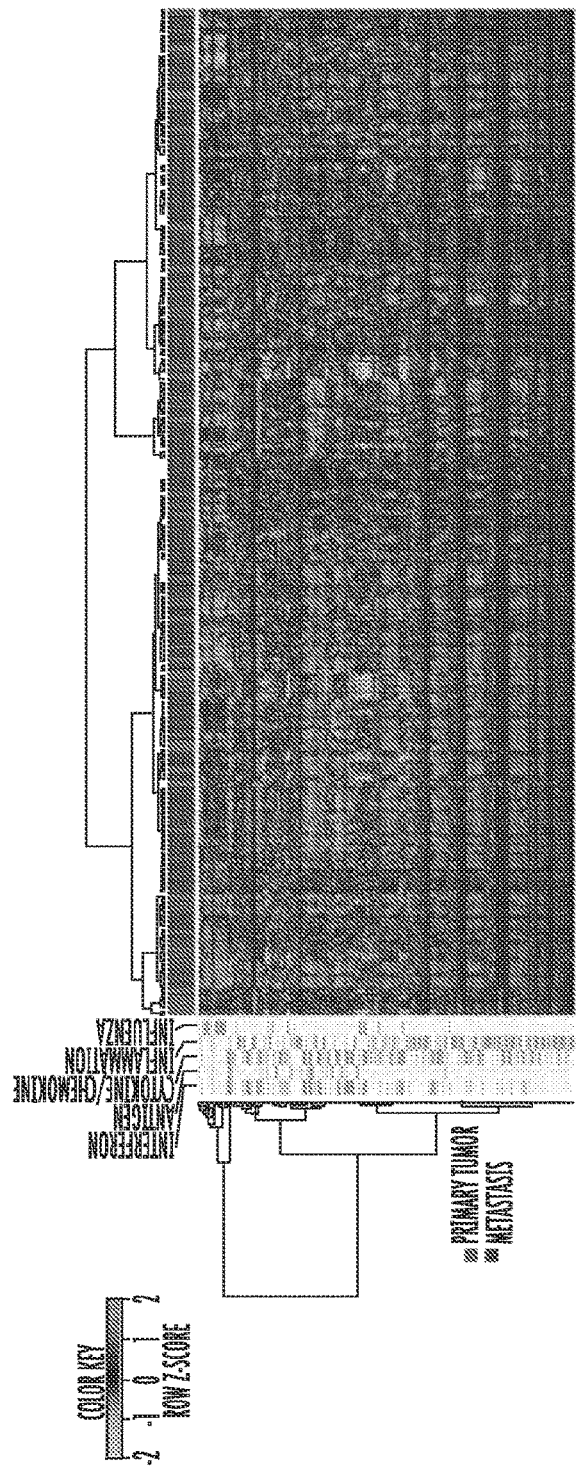

PREDICTING RESPONSE TO EPIGENETIC DRUG THERAPY

CROSS-REFERENCE TO RELATED APPLICATIONS

This application is a 35 U.S.C. § 371 U.S. national entry of International Application PCT/US2015/015017, having an international filing date of Feb. 9, 2015, which claims the benefit of U.S. Provisional Application No. 61/937,149, filed Feb. 7, 2014, and U.S. Provisional Application No. 61/940,488, filed Feb. 16, 2014, the content of each of the aforementioned applications is herein incorporated by reference in their entirety.

STATEMENT OF GOVERNMENTAL INTEREST

This invention was made with government support under grant number CA058184 and CA127141 awarded by the National Institutes of Health. The government has certain rights in this invention.

FIELD OF THE INVENTION

The present invention relates to the field of epigenetics. More specifically, the present invention provides methods and compositions useful for predicting response to epigenetic drug therapy.

BACKGROUND OF THE INVENTION

Cancers are now recognized as being driven by widespread changes in the epigenome including changes in DNA methylation and chromatin packaging. Changes in DNA methylation include global loss of methylation and focal gain of methylation at promoter regions of tumor suppressor genes leading to transcriptional silencing. DNA methylation, the covalent modification of DNA, is mediated by a family of DNA methyltransferases (DNMTs). In recent years, inhibitors of DNMTs (DNMTis) have emerged as therapeutic targets for treatment of myeloid malignancies as well as cutaneous T cell lymphoma. In 2004, the FDA approved the DNMT inhibitor 5-azacitidine (AZA) for treatment of myelodysplastic syndrome. Several groups, including the present inventors, have focused on the therapeutic potential of DNMT inhibitors in the treatment of solid tumors with exciting early possibilities seen in non-small cell lung cancer (NSCLC) and to reverse chemotherapy resistance in ovarian cancers. Recently, in a small number of patients, the present inventors have also seen exciting robust clinical responses in patients with NSCLC who happened to have received therapy to break immune tolerance after having received epigenetic therapy with a DNMTi, 5-azacitidine (AZA), along with an HDAC inhibitor (HDAC), Entinostat.

SUMMARY OF THE INVENTION

Epigenetic therapy is emerging as a potential therapy for solid tumors. To investigate its mechanism of action, we performed integrative expression and methylation analysis of 63 cancer cell lines (breast, colorectal, and ovarian) after treatment with the DNA methyltransferase inhibitor 5-azacitidine (AZA). Gene Set Enrichment Analysis demonstrated significant enrichment for immunomodulatory pathways in all three cancers (14.4-31.3%) including interferon signaling, antigen processing and presentation, and cytokines/chemokines Strong upregulation of cancer testis antigens was also observed. An AZA IMmune gene set (AIMs) derived from the union of these immunomodulatory pathway genes classified primary tumors from all three types, into "high" and "low" AIM gene expression subsets in tumor expression data from both TCGA and GEO. Samples from selected patient biopsies showed upregulation of AIM genes after treatment with epigenetic therapy. These results point to a broad immune stimulatory role for DNA demethylating drugs in multiple cancers.

Much of our above clinical trial work was driven by our pre-clinical studies that showed how low doses of DNMTs may avoid off-target effects, mimic doses seen by patients' tumor cells, and reprogram and inhibit tumor cells, including cancer stem like cells. We have now investigated, first using this pre-clinical paradigm, the global response of 63 cultured cell lines to transient, low-dose AZA in three common human cancers (breast, colorectal and ovarian) by studying the expression and methylation changes at multiple time points. We demonstrate that AZA can upregulate a defined set of immunomodulatory pathways (based on Gene Set Enrichment Analysis (GSEA)) in all three cancer types and we derive a gene panel reflecting this which we term AZA IMmune genes (AIMs). We show how this panel divides primary human cancers in all three cancer types, and other cancer such as NSCLC and melanoma, into a "low" and "high" AIM signature. Importantly, increased expression of AIM genes could also be seen, in subsets of patients treated with AZA in breast and colorectal clinical trials, in a comparison of pre- and post-treatment biopsy samples, suggesting that epigenetic treatment causes enrichment, in vivo, of immunomodulatory genes. Our data shows that the AIM gene panel stratifies patients with common human cancers into an immune low and immune enriched group and suggests that patients with low expression of AIM genes would benefit from epigenetic therapy when combined with immunotherapy.

As described herein, we have identified a unique signature termed AZA Immune gene set or AIM that differentiates patients with a low immune and high immune signature and is regulated by epigenetic drugs such as demethylating drugs, histone deacetylase inhibitors. In certain embodiments, patients with a high immune signature may benefit from immunotherapies such as anti PD1 or anti PDL1 antibodies or vaccines. In other embodiments, patients with a low immune signature or low AIM would be patients who would then benefit from treatment with epigenetic drugs and then subsequent immunotherapy.

Immunotherapy is emerging as one of the most exciting modality in solid tumors with recent identification of use of checkpoint therapy for melanomas, selected lung and renal cancers. However, most solid cancers did not respond to immunotherapy. At present, common solid cancers such as colorectal, breast and ovarian cancers are not thought to be typically as immune driven or immune responsive cancers. We have now shown that these cancers can have an immune rich signature and others that are low in immune signal. Cancers that are high in this immune signature termed "AIM-High" would be candidates for immunotherapy. In addition, we have shown that cancers that are low in this immune signature termed "AIM-Low" or (Aza IMMune-Low) would benefit from epigenetic drugs especially demethylating drugs but also histone deacetylase inhibitors in increasing their immune stimulation and then treating with immunotherapy to treat these cancers.

We have also verified this signature in other cancers such as melanoma and in non-small cell lung cancer. We believe that this biomarker AIM 317 gene panel differentiates solid tumors into high basal and low basal expression in most other solid tumor types and patients with low tumor types would benefit from epigenetic therapy followed by immunotherapy.

Currently there is no knowledge of immune signatures specific to cancers. Our work is novel in that it identifies epithelial cells have an immune function and this immune signature is regulated by epigenetic drugs. Provided herein is a gene panel that identifies patient who have a high immune signature termed "AIM-High" who would benefit from immunotherapy for their cancers. Also provided herein is a gene panel that identifies patients who have a low immune signature termed "AIM-Low" who would benefit from epigenetic therapy followed by immunotherapy for their cancer.

The present invention provides a panel termed "AIM," a panel based on gene expression in three common cancers: colon, breast and ovarian. The AIM panel was then validated in multiple primary human samples in colon, breast and ovarian cancer. Patients are either low or high in this panel. The panel also holds up so far in other cancers including lung and melanoma. Thus, in certain embodiments, the baseline AIM panel can be used as a prognostic panel, for example, patients with high AIM genes may have better survival than patients with low AIM genes. In other embodiments, the baseline AIM panel can also be used to stratify patients who may benefit from epigenetic therapy. For example, patients with low AIM panel baseline may benefit from epigenetic therapy and/or immunotherapy and/or chemotherapy whereas patients with high AIM panel may do well with immunotherapy alone. In further embodiments, patients with a change in AIM panel may be the ones who are responding to therapy.

The present inventors also analyzed common methylation changes in these three cancers associated with loss of gene expression and identified a methylation hub. In particular, a subset of these methylation hubs was also seen in AIM panel, especially IRF7. Cancers tested included colorectal cancer, breast cancers, lung cancers, ovarian cancers, melanomas. Pancreatic, liver and thyroid can also be diagnosed and treating using the methods described herein.

Accordingly, in one embodiment, the present invention provides a method for treating a patient having cancer comprising the steps of (a) obtaining a biological sample from the patient; (b) generating gene expression data from the biological sample; and (c) classifying the gene expression data from the biological sample as high or low AIM based on a comparison to an AIM panel described herein. In another embodiment, the method can further comprise (d) recommending or treating the cancer patient with immunotherapy if the gene expression data from the biological sample is classified as high AIM or treating the cancer patient with epigenetic therapy followed by immunotherapy if the gene expression data from the biological sample is classified as low AIM.

In certain embodiments, the epigenetic therapy comprises treatment with a DNA methyltransferase inhibitor (e.g., 5-azacitidine) and/or a histone deactytelase inhibitor (e.g., entinostat). In other embodiments, the immunotherapy comprises treatment with anti PD1 or anti PDL1 antibodies or vaccines.

In a specific embodiment, a method for treating cancer in a patient comprises the step of administering epigenetic therapy followed by immunotherapy to a patient classified as having a low AIM signature based on a comparison of gene expression data generated from a biological sample obtained from the patient to an AIM panel described herein. In another embodiment, a method for treating cancer in a patient comprises the step of administering immunotherapy to a patient classified as having a high AIM signature based on a comparison of gene expression data generated from a biological sample obtained from the patient to an AIM panel described herein. In a further embodiment, a method for treating cancer in a patient comprises the steps of (a) administering epigenetic therapy followed by immunotherapy to a patient classified as having a low AIM signature based on a comparison of gene expression data generated from a biological sample obtained from the patient to an AIM panel described herein; or (b) administering immunotherapy to a patient classified as having a low AIM signature based on a comparison of gene expression data generated from a biological sample obtained from the patient to an AIM panel described herein.

In one embodiment, a method comprises the step of prescribing epigenetic therapy followed by immunotherapy to a patient classified as having a low AIM signature based on a comparison of gene expression data generated from a biological sample obtained from the patient to an AIM panel described herein. In another embodiment, a method comprises the step of prescribing immunotherapy to a patient classified as having a high AIM signature based on a comparison of gene expression data generated from a biological sample obtained from the patient to an AIM panel described herein. In a further embodiment, a method comprises the steps of (a) prescribing epigenetic therapy followed by immunotherapy to a patient classified as having a low AIM signature based on a comparison of gene expression data generated from a biological sample obtained from the patient to an AIM panel described herein; or (b) prescribing immunotherapy to a patient classified as having a low AIM signature based on a comparison of gene expression data generated from a biological sample obtained from the patient to an AIM panel described herein.

In yet another embodiment, a method comprises the steps of (a) ordering a diagnostic test that assays gene expression from a biological sample obtained from a patient and classifies the gene expression data from the biological sample as high or low AIM based on a comparison to an AIM panel described herein; and (b) administering or prescribing epigenetic therapy followed by immunotherapy to a patient classified as having a low AIM signature based on a comparison of gene expression data generated from a biological sample obtained from the patient to an AIM panel described herein. In an alternative embodiment, a method comprises the steps of (a) ordering a diagnostic test that assays gene expression from a biological sample obtained from a patient and classifies the gene expression data from the biological sample as high or low AIM based on a comparison to an AIM panel described herein; and (b) administering or prescribing immunotherapy to a patient classified as having a high AIM signature based on a comparison of gene expression data generated from a biological sample obtained from the patient to an AIM panel described herein. In a further embodiment, a method comprises the steps of (a) ordering a diagnostic test that assays gene expression from a biological sample obtained from a patient and classifies the gene expression data from the biological sample as high or low AIM based on a comparison to an AIM panel described herein; and (b) administering or prescribing either (i) epigenetic therapy followed by immunotherapy to a patient classified as having a low AIM signature based on a comparison of gene expression data generated from a biological sample obtained from the patient to an AIM panel described herein or (ii) administering or prescribing immunotherapy to a patient classified as having a high AIM signature based on a comparison of gene expression data generated from a biological sample obtained from the patient to an AIM panel described herein.

In a specific embodiment, the biological sample is a solid tumor sample. In another embodiment, the cancer is colorectal, breast or ovarian. In yet another embodiment, the cancer is melanoma or lung cancer. In a more specific embodiment, the lung cancer is non-small cell lung cancer (NSCLC). In certain embodiments, the gene expression data is generated using polymerase chain reaction (PCR). In a specific embodiment, the PCR is qRT-PCR.

Accordingly, in one embodiment, the AIM panel comprises one or more of B2M; CD44; GBP1; HLA-B; HLA-C; ICAM1; IRF7; IRF9; MT2A; OAS1; OAS2; OAS3; OASL; STAT1; EGR1; IFI27; IFI6; IFIT1; IFIT2; IFIT3; IFITM1; ISG15; ISG20; MX1; PSMB8; USP18; XAF1; DDX58; HERC5; UBA7; IFIH1; TNFAIP3; CCL2; CCL20; CCL5; CXCL1; CXCL11; CXCL2; CXCL3; CXCL6; CXCR4; IL8; B2M; CD44; CSF2; DDX58; EGR1; GBP1; HERC5; HLA-B; HLA-C; ICAM1; IFI27; IFI6; IFIT1; IFIT2; IFIT3; IFITM1; IL1R2; IRF7; IRF9; ISG15; ISG20; LCK; MT2A; MX1; OAS1; OAS2; OAS3; OASL; PSMB8; STAT1; UBA7; USP18; XAF1; B2M; HLA-B; HLA-C; PSMB8; PSMB9; TAP1; CTSS; NCF2; ALOX5AP; ANKRD1; AOX1; CCL20; CCL26; CCL5; CXCL1; CXCL11; CXCL2; CXCL6; CXCR4; EREG; FOS; HCP5; HLA-B; IL32; IL8; KCNN4; KLRC2; LSP1; LY96; LYST; MX1; NCF2; PAGE1; RSAD2; S100A8; ADM; C4BPB; CTGF; KLK8; MDK; PLAT; SERPINE1; SPRR3; TFPI; THBD; HSP90AA1; RPL26; ATAD2; CABYR; CSAG1; CT45A1; CT45A5; CT47A11; CTAG1A; CTAG2; CTCFL; DDX43; DSCR8; FAM133A; FMR1NB; GAGE7; HORMAD1; IL13RA2; MAEL; MAGEA10; MAGEA12; MAGEA2B; MAGEA4; MAGEA8; MAGEA9; MAGEB2; MAGEB6; MAGEC1; MAGEC2; PAGE1; PAGE2; PAGE5; PLAC1; PRAME; SPANXA1; SPANXB2; SPANXD; SSX1; SSX3; SSX4B; and SSX7. The foregoing includes, for example, combinations of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, and 161 biomarkers. In particular embodiments, the foregoing combinations are common in any of breast, colorectal and ovarian cancer.

In another embodiment, the AIM panel comprises one or more of HLA-DRB1; EIF4E; EIF4G1; NUP35; UBE2L6; GBP2; HLA-A; HLA-DPB1; HLA-F; IFITM2; IFITM3; MX2; UBE2E1; FAS; FASLG; HLA-DMA; HLA-E; GBP5; IFNGR1; IRF6; VCAM1; IL1A; IL1B; IL6; CCL4; PPBP; EIF4E; EIF4G1; HLA-DRB1; LYN; NUP35; UBE2L6; CASP1; GBP2; HLA-A; HLA-DPB1; HLA-F; IFITM2; IFITM3; IL18; IL6R; IL7R; MX2; NFKB2; UBE2E1; CCL28; CCL3; CCL3L3; CXCR7; GBP5; IFNGR1; IL1A; IL1B; IL6; IRF6; NOD2; STAT5A; VCAM1; PSMA3; CALR; HLA-A; HLA-F; PSME2; ITGAV; ADORA2B; ANXA1; AOC3; CAMP; CCL4; NLRP3; WAS; APOBEC3G; BNIP3; CD19; CEBPB; CEBPG; DEFB1; HP; INHBB; KLRC4; LY75; MX2; NMI; SCG2; TCIRG1; TLR3; TPST1; VWF; CCL3; CCL3L3; FOSL1; IL1A; INHBA; NOD2; PLA2G7; PTX3; S100A7; S100A9; TYROBP; DCBLD2; GP9; PROS1; NUP35; RPL38; XPO1; CALR; RPS27; RPS8; ACTL8; CEP55; OIP5; PASD1; PBK; TMEFF2; TTK; CSAG2; CXorf48; GAGE3; GPAT2; LEMD1; LY6K; MAGEA1; MAGEA11; MAGEA6; MAGEB1; PAGE2B; POTEB; POTEG; SSX2; and ZNF165. The foregoing includes, for example, combinations of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, and 130 biomarkers. In particular embodiments, the foregoing combinations are common any two of breast, colorectal and ovarian cancer.

In a further embodiment, the AIM panel comprises one or more of B2M; CD44; GBP1; HLA-B; HLA-C; ICAM1; IRF7; IRF9; MT2A; OAS1; OAS2; OAS3; OASL; STAT1; EGR1; IFI27; IFI6; IFIT1; IFIT2; IFIT3; IFITM1; ISG15; ISG20; MX1; PSMB8; USP18; XAF1; DDX58; HERC5; UBA7; IFIH1; TNFAIP3; CCL2; CCL20; CCL5; CXCL1; CXCL11; CXCL2; CXCL3; CXCL6; CXCR4; IL8; B2M; CD44; CSF2; DDX58; EGR1; GBP1; HERC5; HLA-B; HLA-C; ICAM1; IFI27; IFI6; IFIT1; IFIT2; IFIT3; IFITM1; IL1R2; IRF7; IRF9; ISG15; ISG20; LCK; MT2A; MX1; OAS1; OAS2; OAS3; OASL; PSMB8; STAT1; UBA7; USP18; XAF1; B2M; HLA-B; HLA-C; PSMB8; PSMB9; TAP1; CTSS; NCF2; ALOX5AP; ANKRD1; AOX1; CCL20; CCL26; CCL5; CXCL1; CXCL11; CXCL2; CXCL6; CXCR4; EREG; FOS; HCP5; HLA-B; IL32; IL8; KCNN4; KLRC2; LSP1; LY96; LYST; MX1; NCF2; PAGE1; RSAD2; S100A8; ADM; C4BPB; CTGF; KLK8; MDK; PLAT; SERPINE1; SPRR3; TFPI; THBD; HSP90AA1; RPL26; ATAD2; CABYR; CSAG1; CT45A1; CT45A5; CT47A11; CTAG1A; CTAG2; CTCFL; DDX43; DSCR8; FAM133A; FMR1NB; GAGE7; HORMAD1; IL13RA2; MAEL; MAGEA10; MAGEA12; MAGEA2B; MAGEA4; MAGEA8; MAGEA9; MAGEB2; MAGEB6; MAGEC1; MAGEC2; PAGE1; PAGE2; PAGE5; PLAC1; PRAME; SPANXA1; SPANXB2; SPANXD; SSX1; SSX3; SSX4B; SSX7; HLA-DRB1; EIF4E; EIF4G1; NUP35; UBE2L6; GBP2; HLA-A; HLA-DPB1; HLA-F; IFITM2; IFITM3; MX2; UBE2E1; FAS; FASLG; HLA-DMA; HLA-E; GBP5; IFNGR1; IRF6; VCAM1; IL1A; IL1B; IL6; CCL4; PPBP; EIF4E; EIF4G1; HLA-DRB1; LYN; NUP35; UBE2L6; CASP1; GBP2; HLA-A; HLA-DPB1; HLA-F; IFITM2; IFITM3; IL18; IL6R; IL7R; MX2; NFKB2; UBE2E1; CCL28; CCL3; CCL3L3; CXCR7; GBP5; IFNGR1; IL1A; IL1B; IL6; IRF6; NOD2; STAT5A; VCAM1; PSMA3; CALR; HLA-A; HLA-F; PSME2; ITGAV; ADORA2B; ANXA1; AOC3; CAMP; CCL4; NLRP3; WAS; APOBEC3G; BNIP3; CD19; CEBPB; CEBPG; DEFB1; HP; INHBB; KLRC4; LY75; MX2; NMI; SCG2; TCIRG1; TLR3; TPST1; VWF; CCL3; CCL3L3; FOSL1; IL1A; INHBA; NOD2; PLA2G7; PTX3; S100A7; S100A9; TYROBP; DCBLD2; GP9; PROS1; NUP35; RPL38; XPO1; CALR; RPS27; RPS8; ACTL8; CEP55; OIP5; PASD1; PBK; TMEFF2; TTK; CSAG2; CXorf48; GAGE3; GPAT2; LEMD1; LY6K; MAGEA1; MAGEA11; MAGEA6; MAGEB1; PAGE2B; POTEB; POTEG; SSX2; ZNF165, IFI44, IFI44L, IRF7, IFI30, IFI16, IFNB1 and IRF3. The foregoing includes, for example, combinations of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, and 291 biomarkers.

In another embodiment, the cancer is breast cancer and the AIM panel comprises one or more of IRF8; JAK2; EIF2AK2; TPR; NLRX1; HLA-DMB; CCR9; CXCL12; CXCL9; EIF2AK2; IL6ST; IRF8; JAK2; PIK3R2; TPR; PSMC6; MRC2; ADORA2A; BCL2; CCR9; CD81; CRP; CXCL9; DEFB103A; LBP; NCF1; ORM1; ORM2; TGFB2; and TPR. The foregoing includes, for example, combinations of 2, 3, 4, 5, 6, 7, 8, 9, 10, 11, 12, 13, 14, 15, 16, 17, 18, 19, 20, 21, 22, 23, 24, 25, 26, 27, 28, 29, and 30 biomarkers. In more specific embodiments, the cancer is a breast cancer and the AIM panel comprises one or more of IFI27, IFI6, IFIT1, IFITM1, IRF9, ISG15, MX1, and OASL. The foregoing includes, for example, combinations of 2, 3, 4, 5, 6, 7, 8 of IFI27, IFI6, IFIT1, IFITM1, IRF9, ISG15, MX1, and OASL.

In a further embodiment, the cancer is colon cancer and the AIM panel comprises one or more of CAMK2B; HLA-DRB3; PTAFR; PTPN1; EIF4A2; KPNA2; KPNA3; NUP107; NUP155; NUP205; NUP37; NUP43; NUP85; NUP93; SEH1L; UBE2N; GZMB; PRF1; CCR7; CXCL10; CXCL16; CXCR3; PF4; CAMK2B; CDK1; CSF2RB; EIF4A2; HLA-DRB3; HRAS; IL1R1; IL1RN; IL2RA; IL2RG; IRAK1; KPNA2; KPNA3; MAP2K4; NRAS; NUP107; NUP155; NUP205; NUP37; NUP43; NUP85; NUP93; PELI3; PRL; PTAFR; PTPN1; RBX1; SEH1L; SH2B1; SHC1; UBE2N; PSMA6; PSMB10; PSMB3; PSMB6; PSMD1; PSMD10; SEC61B; SEC61G; ITGB5; AFAP1L2; AIF1; APOBEC3F; CADM1; CCR7; CD83; CXCL10; CYSLTR1; GAGE1; IL17RB; KLRC3; LGALS3BP; LYZ; MGLL; MICB; NFATC4; NOS2; OR2H2; PRF1; PSG8; PTAFR; PYDC1; S100A12; TFF3; UMOD; F2; F2R; F5; F7; MIA3; PF4; SOD1; GTF2F2; NUP107; NUP155; NUP205; NUP37; NUP43; NUP85; NUP93; POLR2K; POLR2L; RPL11; RPL12; RPL14; RPL15; RPL37A; RPL4; RPL41; RPLP1; RPS11; RPS14; RPS18; RPS23; RPS28; RPS4Y1; RPS6; SEH1L; CASC5; CT47B1; DKKL1; GAGE1; LUZP4; NXF2; PAGE4; POTEC; POTED; POTEE; RGS22; RQCD1; SPA17; XAGE2B; XAGE3; and XAGE5. The foregoing includes, for example, combinations of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, and 137 biomarkers. In more specific embodiments, the cancer is a colon cancer and the AIM panel comprises one or more of CTGF, HSP90AA1, IFI27, IFI6, IFITM1, KLK8, MDK, MT2A, OAS3, PAGE1, PLAT, DEFB1, POLR2L, and TCIRG1. The foregoing includes, for example, combinations of 2, 3, 4, 5, 6, 7, 8, 9, 10, 11, 12, 13, and 14 biomarkers.

In yet another embodiment, the cancer is ovarian cancer and the AIM panel comprises one or more of GBP4; HLA-DPA1; HLA-G; IFNG; PTPN6; IFI35; RNASEL; STAT2; CCRL1; CXCL5; CXCR6; XCL1; XCL2; CSF2RA; CSH1; GBP4; GH1; HLA-DPA1; HLA-G; IFI35; IFNG; IL2RB; MAP3K8; PELI1; PELI2; PTPN6; RNASEL; STAT2; VAV1; HLA-G; CD36; APOL3; BNIP3L; C2; CD1D; CD40; CFP; CHST2; COLEC12; DCDC2; DMBT1; ELF3; GPR68; HLA-G; IL29; KRT1; MST1R; NOX4; SP140; STAB1; TNFAIP6; TNIP1; CD36; F12; HOXB13; LYVE1; PROC; RPS12; ACRBP; DPPA2; HSPB9; PIWIL2; SAGE1; SYCE1; TMEFF1; TSGA10; and XAGE-4. The foregoing includes, for example, combinations of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, and 67 biomarkers. In more specific embodiments, the cancer is a ovarian cancer and the AIM panel comprises one or more of IFI27, IFITM1, IL6, GBP5, IL32, IL8, NCF2, PLAT, CXCL2, GBP1, HLA-C, ICAM1, IFI6, IFIT1, IRF7, and TAP1. The foregoing includes, for example, combinations of 2, 3, 4, 5, 6, 7, 8, 9, 10, 11, 12, 13, 14, 15, and 16 biomarkers.

In another embodiment, an ovarian cancer panel can comprise one or more of IFI27, IFITM1, IL6, GBP5, IL32, IL8, NCF2, PLAT, CXCL2, GBP1, HLA-C, ICAM1, IFI6, IFIT1, IRF7, TAP1, PAGE5, PAGE2, CTAG1A, MAGEA9, MAGEA2B, SPANXA1, SPANXD, MAGEA1, MAGEA8, MAGEB2, FMR1NB, MAEL, SSX4B, GAGE7, IFI6, ISG15, OASL, DDX58, IFIH1, IFIT2, IFIT1, OAS2, STAT1, IFI44, OAS1, IFITM1, IFITM3, IRF9, IFI44L, MX1, IFI27, IRF7, IFI30, IFI16, MX2, IFNB1, IRF3, and ISG20. The foregoing includes, for example, combinations 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, and 53 biomarkers.

In another embodiment, an ovarian cancer panel can comprise one or more of IFI27, IFITM1, IL6, GBP5, IL32, IL8, NCF2, PLAT, CXCL2, GBP1, HLA-C, ICAM1, IFI6, IFIT1, IRF7, and TAP1. The foregoing includes, for example, combinations of 2, 3, 4, 5, 6, 7, 8, 9, 10, 11, 12, 13, 14, and 15 biomarkers. In yet another embodiment, an ovarian cancer panel can comprise one or more of PAGE5, PAGE2, CTAG1A, MAGEA9, MAGEA2B, SPANXA1, SPANXD, MAGEA1, MAGEA8, MAGEB2, FMR1NB, MAEL, SSX4B, and GAGE7. The foregoing includes, for example, combinations of 2, 3, 4, 5, 6, 7, 8, 9, 10, 11, 12, and 13 biomarkers. In a further embodiment, an ovarian cancer panel can comprise one or more of IFI6, ISG15, OASL, DDX58, IFIH1, IFIT2, IFIT1, OAS2, STAT1, IFI44, OAS1, IFITM1, IFITM3, IRF9, IFI44L, MX1, IFI27, IRF7, IFI30, IFI16, MX2, IFNB1, IRF3, and ISG20. The foregoing includes, for example, combinations of 2, 3, 4, 5, 6, 7, 8, 9, 10, 11, 12, 13, 14, 15, 16, 17, 18, 19, 20, 21, 22, and 23 biomarkers.

In a further embodiment, the cancer is lung cancer and the AIM panel comprises one or more of CCL26, CCL5, DDX58, ICAM1, IFI27, IFI6, IFIT1, IFITM1, IL32, IL6, ISG15, MX1, NCF2, OASL, and TAP1. The foregoing includes, for example, combinations of 2, 3, 4, 5, 6, 7, 8, 9, 10, 11, 12, 13, 14, and 15 biomarkers. In further embodiments, the panel comprises at least IFI27, IFITM1 and IFI6 and optionally one or more of a marker described herein. In such embodiments, the cancer comprises ovary, breast, colon and lung.

BRIEF DESCRIPTION OF THE FIGURES

FIG. 1A-1F. GSEA analysis of transcripts regulated by AZA in breast, colon, and ovarian cancer cell lines reveals pathways common to all three cancer types. Venn Diagram showing the number of GSEA gene sets: FIG. 1A: upregulated (NES>2.15, FDR<0.25) and FIG. 1B: downregulated (NES<−2.15, FDR<0.25) by AZA in breast, colon, and ovarian cell lines. Agilent array data were normalized and analyzed by GSEA. Pie charts of gene sets common to all three cancer types that were (FIG. 1C) upregulated and (FIG. 1D) downregulated show the different categories of the common GSEA pathways. The "Immune" sector is broken down further into specific pathways characterized as part of the interferon response, antigen presentation, cytokines/chemokines, inflammation, and influenza virus. FIG. 1E: Heat maps showing the NES value from GSEA for each cell line (x axis) and each of the 15 immune pathways (y-axis) shown in FIG. 1C. The colored rectangle corresponding to NES is graded from gray (low) to orange (high). Subtypes for each cancer type are coded by the black, grey, and white boxes shown below the figure. FIG. 1F: Summary of GSEA gene sets upregulated by AZA in each cancer type and the percent that were immune-related.

FIG. 2A-2C. AZA activates diverse pathways involved in the immune response in breast, colon, and ovarian cancers. FIG. 2A: Schematic of the interferon response to pathogens in an epithelial cell. Arrows next to gene names indicate that they are upregulated twofold by AZA in breast (red), colon (blue), or ovarian (green) cell lines. FIG. 2B: Upregulation of immune genes by AZA treatment in two cell lines from each tumor type (red=breast cancer, green=ovarian cancer, blue=colon cancer). Yellow bars denote the fold change of the DKO cell line (haplo insufficient for DNMT1 and null for DNMT3) compared to the parent HCT116 cell line. Y-axis represents AZA/Mock fold change (log 2). FIG. 2C: qRT-PCR validations of genes from FIG. 2B. Y-axis represents AZA/Mock fold change (linear). Cell lines are the same colors as in FIG. 2B. Each bar represents the average and standard deviation of three biological replicates.

FIG. 3A-3C. AZA activates genes involved in antigen presentation and processing in breast, colon, and ovarian cancers. FIG. 3A: Schematic of antigen processing. Arrows next to gene names indicate that they are upregulated twofold by AZA in breast (red), colon (blue), or ovarian (green) cell lines. FIG. 3B: Upregulation of antigen presentation genes by AZA treatment in two cell lines from each tumor type (red=breast cancer, blue=colon cancer, green=ovarian cancer). Yellow bars denote the fold change of the DKO cell line (haplo insufficient for DNMT1 and null for DNMT3) compared to the parent HCT116 cell line. FIG. 3C: qRT-PCR validations of genes from FIG. 3B. HLA-C was undetectable by qRT-PCR in HCC1569, ZR751, and HT29. Each bar represents the average and standard deviation of three biological replicates.

FIG. 4A-4F. The AIM 317 gene panel clusters TCGA and GEO tumors into high and low immune signatures. Tumors from The Cancer Genome Atlas (TCGA) cluster into "high" and "low" immune groups based on the AIM genes. The bars on the far left show the five sets of AIM genes driving the clustering, interferon, antigen, cytokines/chemokines, inflammation and influenza. The shades of blue bars at the top denote tumor vs. normal, stage, and receptor status for breast cancer, CIMP, stage, and colon vs. rectum for colon/rectum cancer, and stage for ovarian cancer. The heat map shows transcript levels from green (low) to red (high). FIG. 4A: breast cancers; FIG. 4B: colorectal cancers; FIG. 4C: ovarian cancers. Tumors from publicly available (GEO) data sets show similar clustering: FIG. 4D: breast cancers; FIG. 4E: colorectal cancers; FIG. 4F: ovarian cancers.

FIG. 5A-5E. Core biopsies from breast and colorectal cancer patients treated with AZA/Entinostat show upregulation of the AIM genes. FIG. 5A: Summary of GSEA gene sets upregulated and downregulated by AZA/Entinostat in breast and colorectal cancer biopsies. Percentages of gene sets that are immune-related are listed. Heat maps for FIG. 5B: triple negative breast and FIG. 5C: colorectal cancer trial samples. Each pair includes "Pre" (baseline or before AZA/Entinostat treatment) and "Post"=8 weeks after AZA/Entinostat treatment) and depicts levels of AIM genes (listed on the left). FIGS. D-E: Bar plots for each breast cancer (FIG. 5D) or colorectal cancer (FIG. 5E) patient biopsy represent a log 2 (Pre/Post) fold change (y axis) of individual genes in the GSEA interferon signaling and antigen presentation gene sets. Breast cancer patient #5 (6 mo) represents the 6 month post biopsy specimen.

FIG. 7A-7P. Plots of AZA inducible genes for each group of GSEA pathways in each cell line. The most immunogenic cell lines selected for validation/further study are highlighted with colored boxes. ZR751 and HCC1569 breast cancer cell lines are denoted in red, A2780 and TykNu ovarian cancer cell lines in green, COLO201 and HT29 colon cancer cell lines in blue, and DKO in orange.

FIG. 8A-8C. FIG. 8A: Distribution of demethylated/re-expressed genes (162 genes) in cell lines across all three cancers. Bars indicate whether the genes are demethylated and re-expressed in breast (red), colorectal (blue), or ovarian (green) cancer cell lines after AZA treatment. Dark red bar indicates that the demethylated and re-expressed genes are also in our AIM panel. FIG. 8B: Number of cell lines in each tumor type that had at least one gene demethylated and re-expressed, and at least one immune gene demethylated and re-expressed. FIG. 8C: Gene expression categories and percentages of the demethylated/re-expressed genes.

FIG. 9A-9D. AIM genes are induced by TSA but not by chemotherapeutic agents. FIG. 9A: Six colon cancer cell lines were treated with 300 nM TSA for 18 hours; heat map shows levels of AIM genes after TSA compared to AZA treatment or the genetic mimic DKO (DNMT1+/− DNMT3−/−) cell line. FIG. 9B: Box plots of AIM genes after TSA treatment. FIG. 9C: Box plots of AIM genes in DKO cells compared to the parent HCT116 cell line. The orange lines indicate 2 fold change. FIG. 9D: A2780 ovarian cancer cells were treated with 500 nM AZA or carboplatin for 72 hours, then allowed to recover for 7 days without drug before RNA was isolated. qRT-PCR was performed for IFI27, IL-15, IRF7, and MAGEB2 genes. Blue bars indicate Mock treatment, purple indicate AZA, and orange indicate carboplatin. Fold change is plotted on the Y axis. Each bar represents the average and standard deviation of three biological replicates.

FIG. 10A: GSEA analysis of cancer testis antigens shows that the pathway is upregulated (NES>2.15, FDR<0.25) by AZA in breast, colorectal, and ovarian cancer cell lines. The colored rectangle corresponding to NES is graded from gray (weak) to orange (strong). FIG. 10B: Cell line number and total cell line number in breast, colorectal and ovarian cancer (see FIG. 10A).

FIG. 11A-11B. The AZA-induced immune genes separate lung and melanoma TCGA tumors into distinct clusters. Tumors from The Cancer Genome Atlas (FIG. 11A) non-small cell lung cancers, (FIG. 11B) melanomas cluster into "high" and "low" expressing immune signatures based on the AIM gene expression. The bars on the far left show the five sets of AIM genes driving the clustering. The shades of blue and orange bars at the top denote squamous versus adenocarcinoma for lung cancer, (LUAD=adenocarcinoma, LUSC=squamous) and primary tumor (light blue) versus metastasis (dark blue) for melanoma. The heat map shows transcript levels from green (low) to red (high).

DETAILED DESCRIPTION OF THE INVENTION

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

Figure 6:
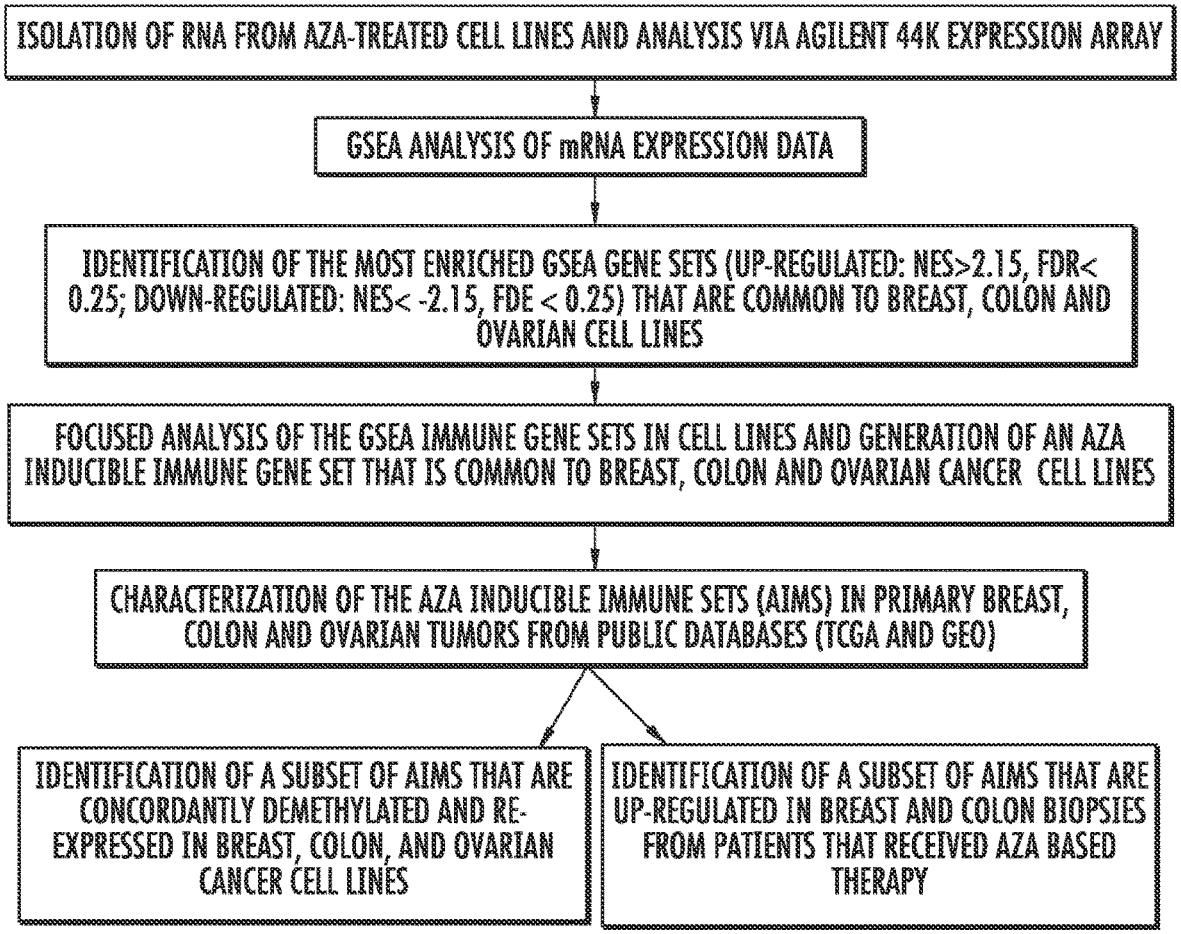
FIG. 6. Schematic of analysis of AZA-treated cell lines and generation of AIM gene panel. Agilent array data were normalized and analyzed by GSEA. The most enriched GSEA gene sets for each tumor type were intersected to produce 80 common upregulated gene sets, out of which we focused our analysis on the upregulated immune gene sets. This immune signature was applied to primary tumors from publicly available cohorts as well as biopsies from AZA and Entinostat trials in breast and colorectal cancer.
Figure 712:
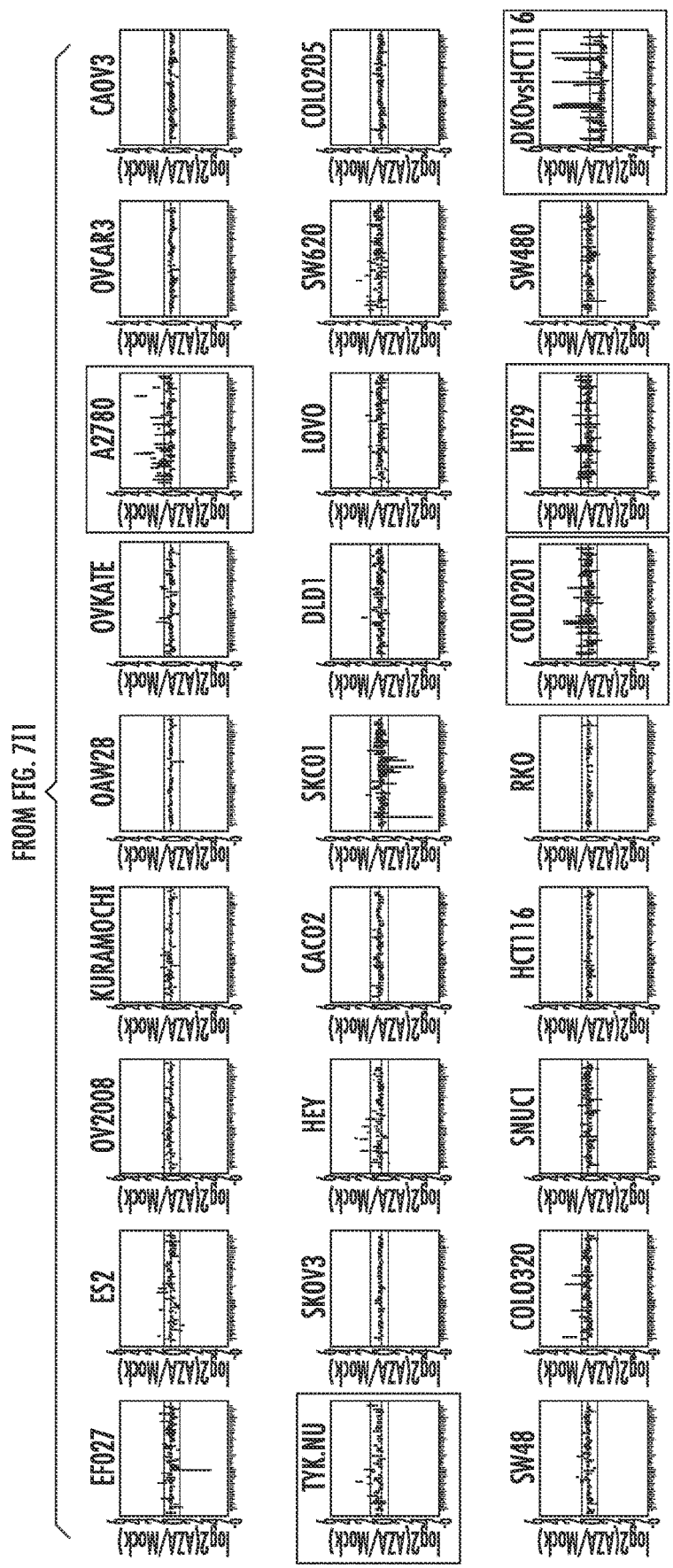
Figure 702:
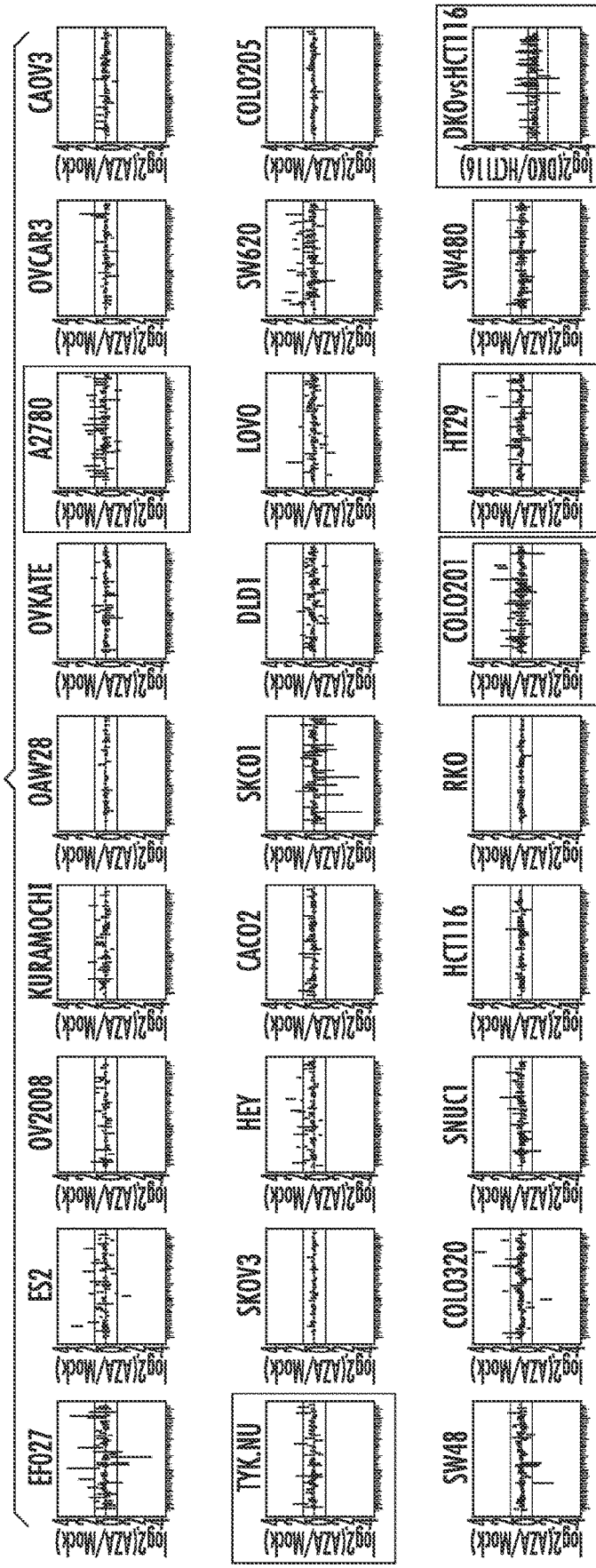

In the context of the above background, we explored further our understanding of the global pathway changes after treatment with low doses of the DNMTi AZA in cell lines from multiple common human cancers. A total of 63 cancer cell lines (26 breast, 14 colorectal, and 23 ovarian) were treated with low dose, 500 nM, AZA for three days. DNA and RNA were isolated at multiple time points following initial drug application and analyzed for genome-wide changes in DNA methylation and gene expression (Agilent 44K Expression Array). We used these genomics data to identify the most enriched pathway alterations as analyzed by GSEA (FIG. 1, FIG. 6) focusing upon the ~top 30% of all upregulated and downregulated gene sets. GSEA analyses of AZA inducible genes identified 80 upregulated gene sets and 52 downregulated gene sets that were common between the three cancer types (FIG. 1A,B; FIG. 6). These gene sets could be broadly divided into four categories including cell cycle control (cell cycle, mitosis, meiosis), DNA replication (DNA replication and packaging, transcription), mRNA splicing and translation, and immune response (FIG. 1C,D; Tables 2 and 3). In Table 2, the 80 GSEA gene sets up-regulated with NES>2.15, FDR<0.25 by AZA in breast, colorectal, and ovarian cell lines. See also FIG. 1A. In Table 3, the 52 GSEA gene sets down-regulated with NES<−2.15, FDR<0.25 by AZA in breast, colorectal, and ovarian cell lines. See also FIG. 1B. The majority of the immune genes showed upregulation by AZA (15/16 gene sets or 93.7%) except for the "systemic lupus erythematosus" gene set, which also showed downregulation (Tables 2 and 3). We thus focused the remainder of our analysis on those immune gene sets that only showed upregulation in response to AZA.

The above-mentioned 15 upregulated immune gene sets (FIG. 1C) were classified as interferon signaling, antigen presentation, chemokine and cytokine signaling, inflammation, and influenza (FIG. 1C). See also Table 1, AIM gene panel: Interferon, Antigen Presentation, Cytokine/Chemokine, Inflammation, and Influenza groups are categories of GSEA pathways. In Table 1, percentages indicate how many genes from the GSEA gene set are included in AIM gene lists. "Common Genes in 3 Types of Cancer" lists the genes in each pathway upregulated by AZA in all three tumor types. "Common Genes in Any 2 Types" lists the genes in each pathway upregulated by AZA in any two cancer types. "Unique Genes" lists the genes in each pathway upregulated by AZA in only one tumor type.

Figure 1E:
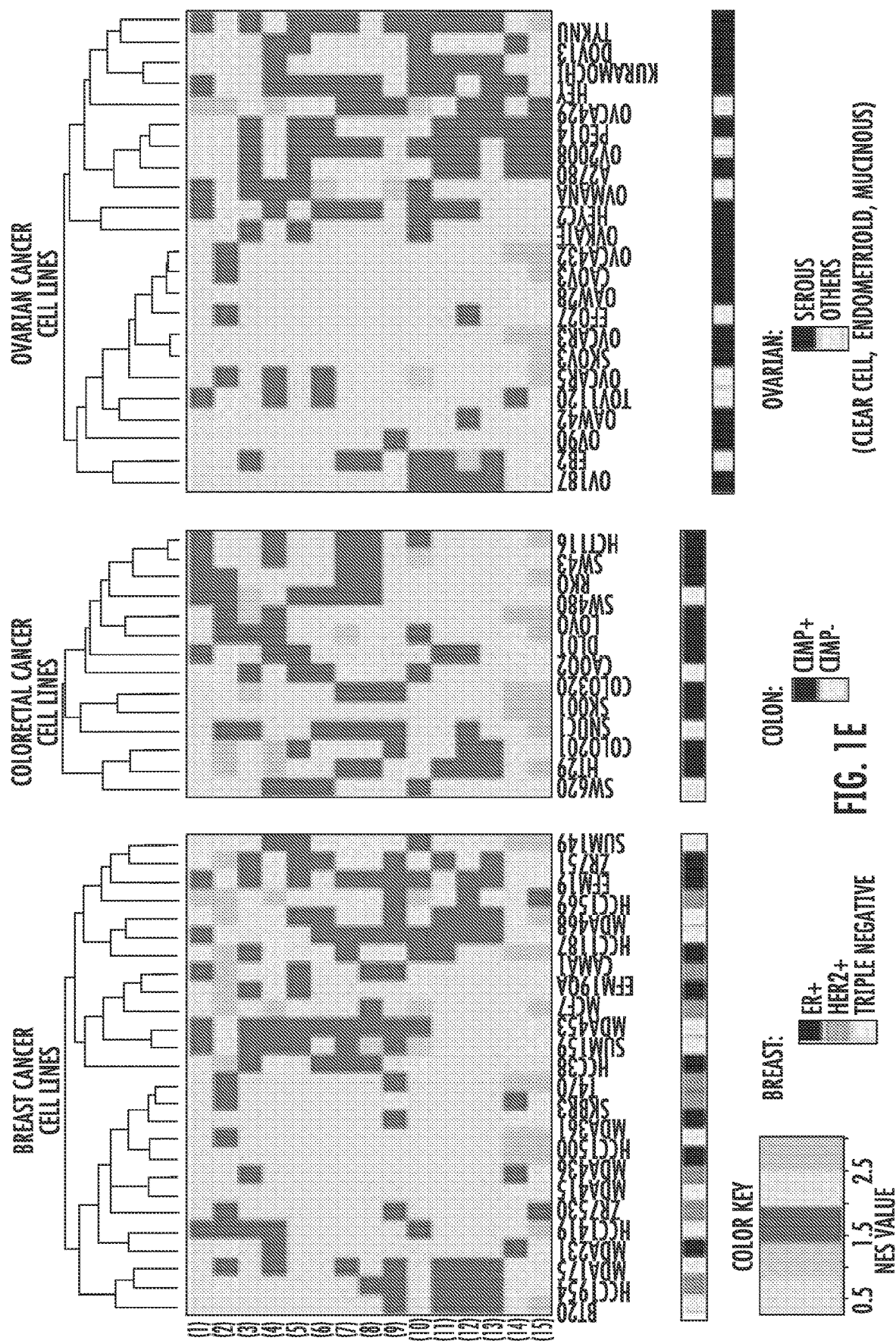

These immune pathways were activated in almost every cell line in response to AZA and did not cluster with a specific subtype of cancer (for example, receptor status in breast cancers, CpG Island Hypermethylator Phenotype (CIMP), or histologic subtypes) (FIG. 1E). Overall immune pathway upregulation is highest in ovarian cancers (31.3%) followed by breast (16.9%) and colorectal (14.4%) (FIG. 1F). We compared these 80 upregulated gene sets from our three cancer types to 14 lung cancer cell lines that had been treated with the same AZA dosing schedule. Interestingly, 76/80 (95%) of the gene sets common to breast, colon, and ovarian cell lines (FIG. 1A) were also upregulated in the lung cancer cell lines. In addition, 23.3% of significantly upregulated pathways in the lung cancer cell lines were also immune related. This suggested that AZA drives common signaling pathways in many solid tumor types and immunomodulatory pathways are a significant fraction of these AZA upregulated pathways.

Figure 7H2:
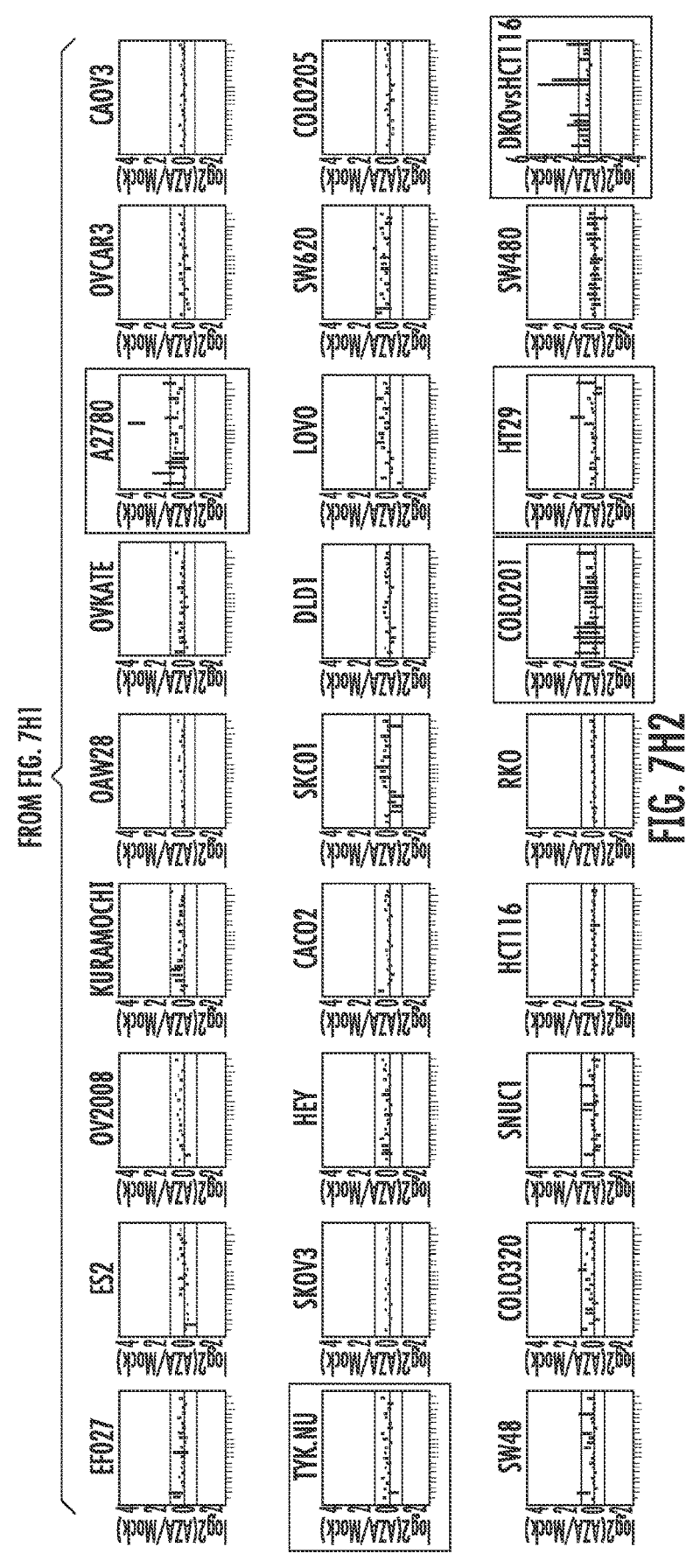
Figure 7M2:
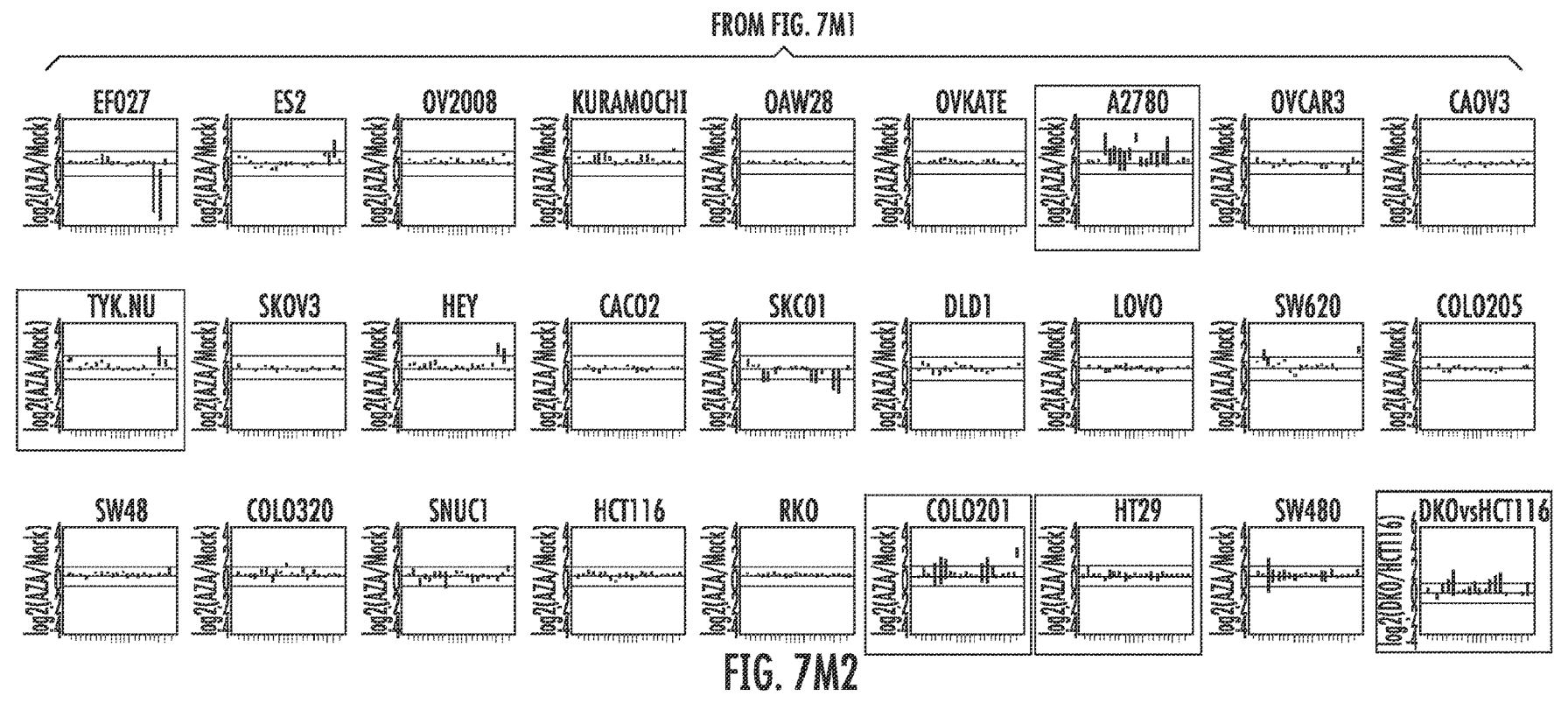

Further analysis of the immune genes from these 15 upregulated immune gene sets (Table 1) characterized by greater than twofold expression changes were then categorized as an AZA IMmune Gene set (AIM). The expression values for these AIM genes (Table 1), comprised of 317 genes from 63 cancer cell lines (breast, colorectal and ovarian) are shown arranged by the respective immune gene sets (FIG. 7). The plots detail the cell lines with the greatest gene expression changes in response to AZA and rectangles have been placed on these cell lines used for the subsequent validation studies (FIG. 7).

Figures 8B, 8C:
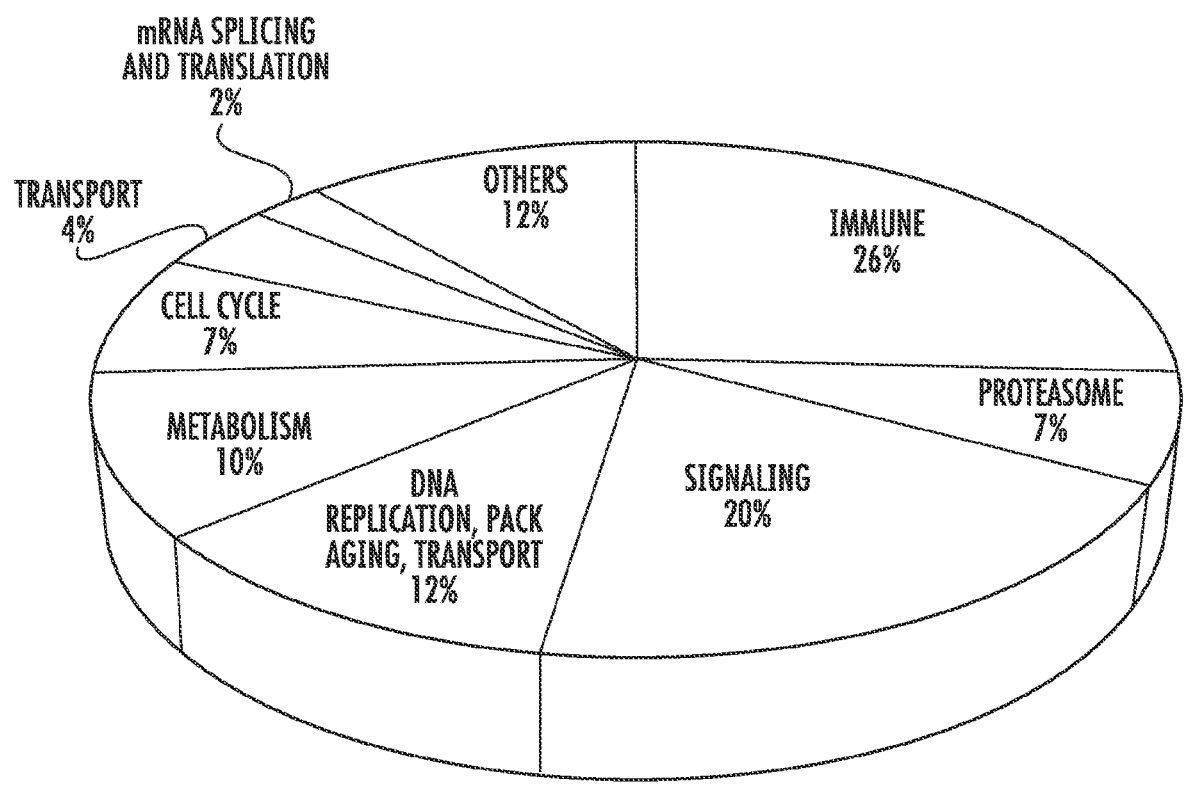

The canonical effects of AZA have traditionally been described as demethylation of promoter regions and subsequent expression of the silenced gene. Many of the pathway changes in response to AZA, such as increased expression of immune genes, may be the result of downstream events elicited by a small number of hubs related to promoter DNA demethylation and associated gene upregulation. We investigated hub networks in our current pan-cancer analyses by first searching, in a genome-wide analysis using the Infinium 450K methylation platform, for genes that have AZA-induced demethylation of cancer-specific, DNA hypermethylated, CpG islands associated with proximal promoter regions. The total number of such demethylated genes in the cell lines from breast, ovarian and colorectal cancers was 162 (FIG. 8A). A subset of these genes (4.9%) showed demethylation and re-expression in all three cancer types including PYCARD, B3GALT4, CARD9, EID3, TSPYL5, IFF01, FERMT3, and AC5. The highest percentages of these demethylation and re-expression events were again seen in immune genes; 26%, of the 162 genes were categorized as immune related (FIG. 8B,C). Overall, immune gene demethylation and re-expression was again highest in ovarian cancer cell lines (53.8%) followed by colorectal (42.8%) and breast (30.7%) cancer cell lines (FIG. 8B). Of note, amongst these 162 genes, 8 (4.9%) were also in our AIM gene set (BNIP3, HERC5, ICAM1, IRF7, MX1, MST1R, PSMB8, TCRIG1) with IRF7, a member of the interferon regulatory factor family of transcription factors in particular being notable for being a canonical demethylated and reexpressed gene.

Validation of AIM Genes.

In order to validate our findings for AIM genes from the expression microarrays, we investigated selected genes by quantitative reverse transcriptase PCR (qRT-PCR) in two cell lines from each cancer type which showed the highest upregulation of transcripts in response to AZA in the array (HCC1569 and ZR751 for breast cancer, COLO201 and HT29 for colorectal cancer, and A2780 and TYKNU for ovarian cancer) (FIG. 7). We concentrated on key genes for individual steps in the associated immune pathways and especially for the interferon response as selected by the array data (FIG. 2A, B). Many AIM genes are part of or downstream of the interferon response (including antigen presentation and cytokines/chemokines). Each chosen gene validated in the qRT-PCR assays for AZA-induced re-expression (FIG. 2C).

GSEA analysis identified antigen processing and presentation as key pathways upregulated by AZA (FIG. 1C, FIG. 3A); these are among the interferon regulated genes in the type I interferon response. Antigens and antigen presentation genes were upregulated in representative cell lines from each tumor type and in DKO cells (FIG. 3B). Upregulation of selected genes for the antigen presentation pathways was validated by qRT-PCR (FIG. 3C) and represent regulation by AZA at most every step of antigen presentation, in all three cancer types (FIG. 3A).

It is especially noteworthy that the DKO cell line (haploinsufficient for DNMT1 and null for DNMT3B), which is shown as a genetic mimic of AZA treatment (FIG. 2B, FIG. 7) induces significant upregulation for most AIM genes (FIG. 9A, C). To determine whether this was specific to DNMT inhibitors, we also treated cells with an HDAC inhibitor (TSA) that has been used extensively in our laboratory. We show that TSA also regulates subsets of AIM genes but not as uniformly or robustly as DKO cells or AZA treated cells (FIG. 9A, B, C). This activation appears to be in response to epigenetic agents and not the result of a general cell stress response that could be elicited by chemotherapeutics such as carboplatin. Our data demonstrate that treatment of an ovarian cancer cell line A2780, for 72 hours with 500 nM carboplatin does not lead to overexpression of AIM genes IFI27, IRF7, IL15, or MAGEB2, all of which are increased in AZA-treated cells (FIG. 9D).

Figures 10A, 10B:
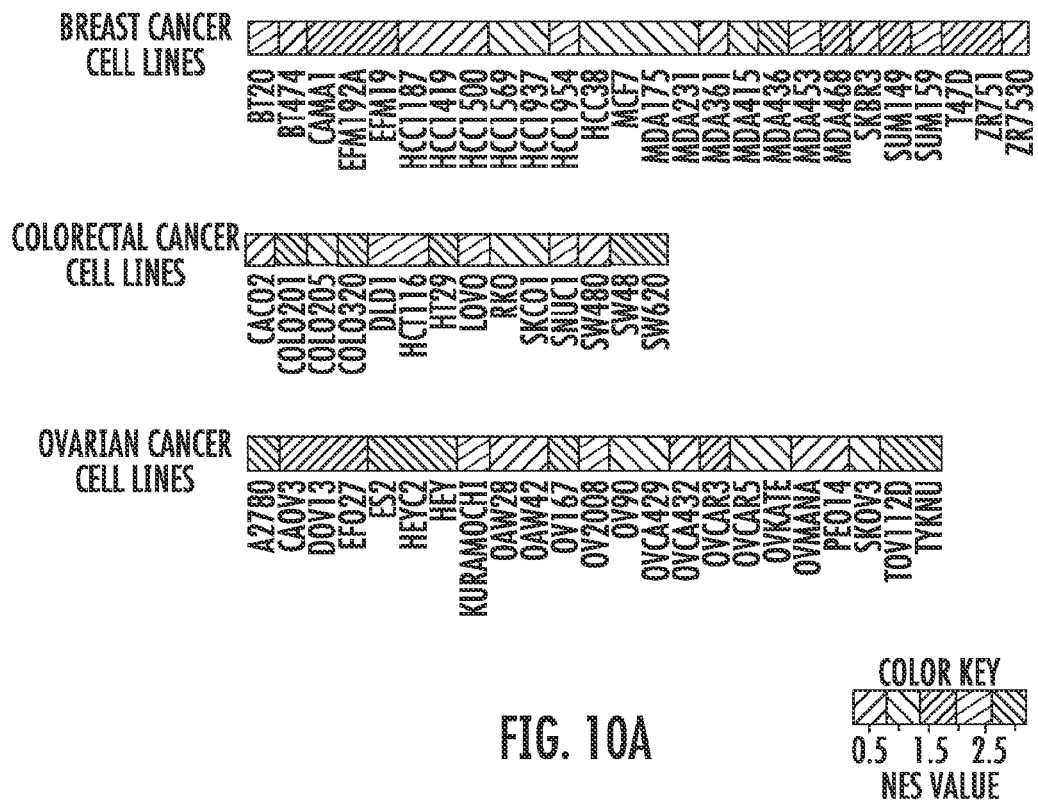
FIG. 10A-10B.
Figure 12:
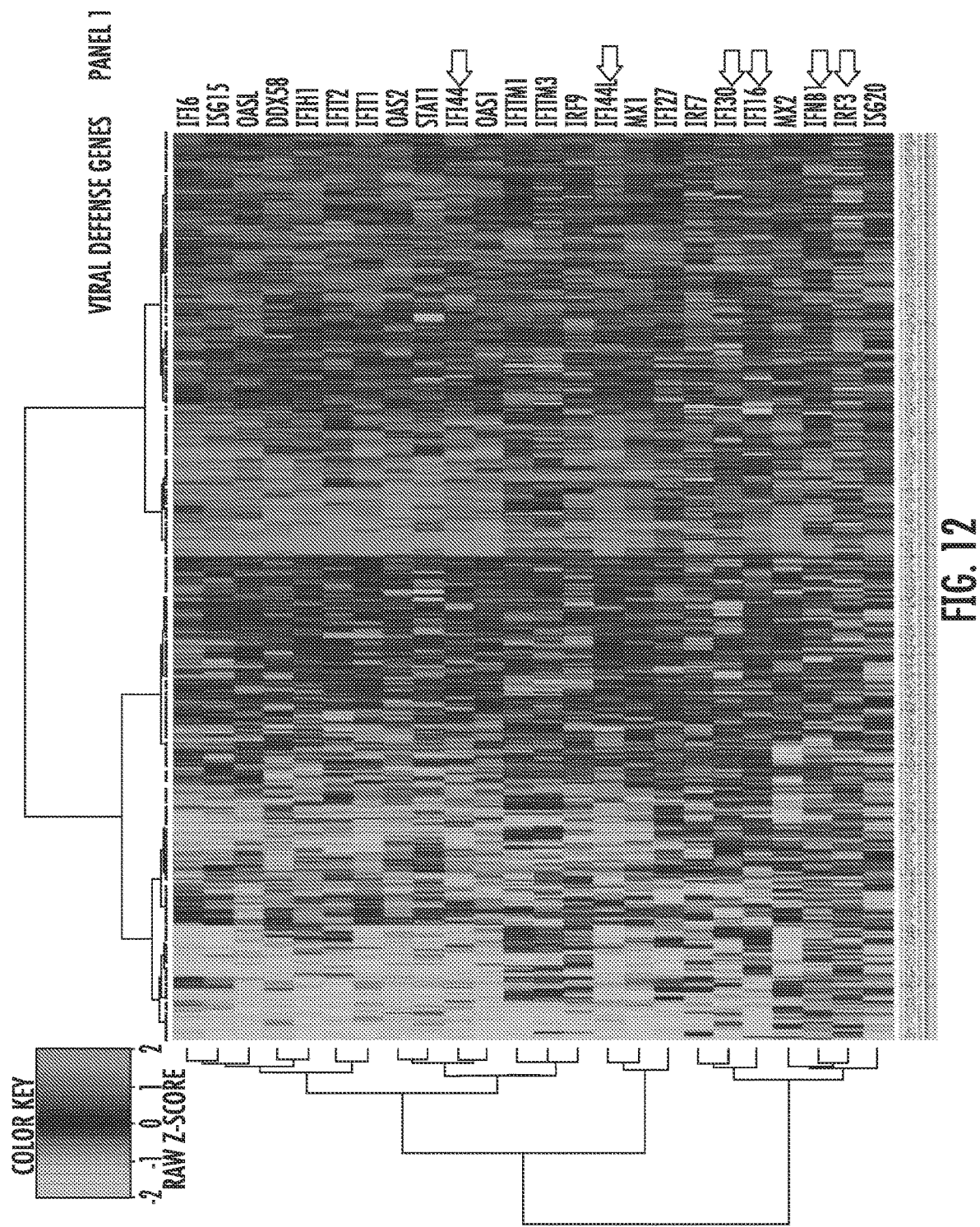
FIG. 12. Heatmap showing panel of viral defense genes.
Figure 13:
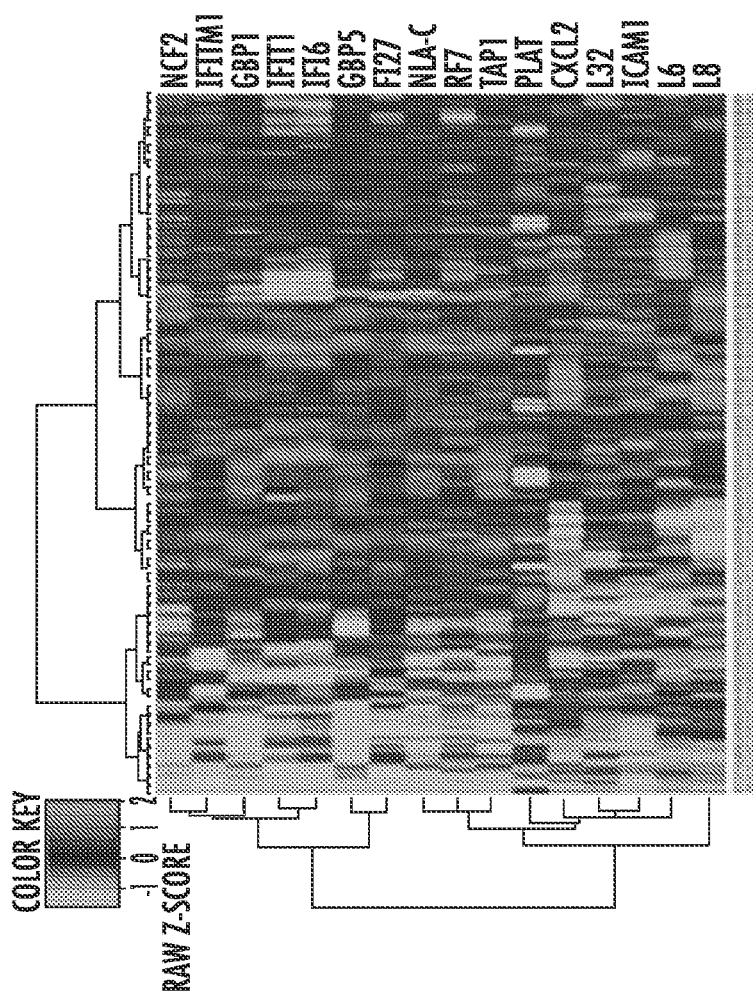
FIG. 13. Heatmap and panel of AIM genes.
Figure 14:
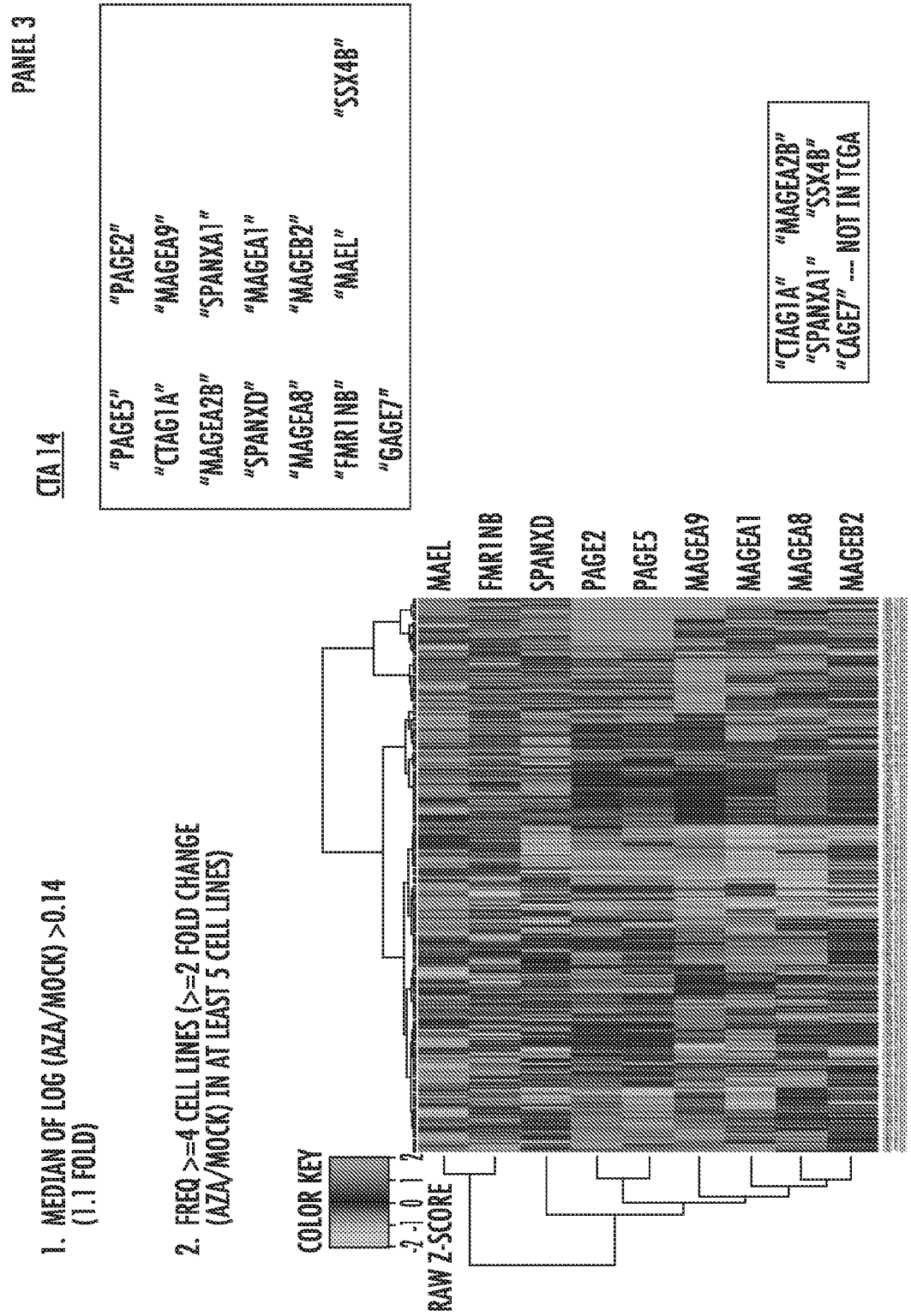
FIG. 14. Heatmap and panel of AIM genes including cancer testis antigens.

Demethylation and upregulation of cancer testis antigens by AZA has been previously described. Cancer testis antigens are critical to tumor immunology, but GSEA does not have a well-defined cancer testis antigen gene list. Thus, we created a gene set from the well-annotated CT database and ran GSEA on the 63 cell lines using the same cutoffs for significance as in FIG. 1. The cancer testis antigens were significantly enriched in many cell lines, and were only upregulated by AZA (FIG. 10). The upregulation of cancer testis antigens was again seen in all three cancer types although this was more pronounced for colorectal (64.3%) and ovarian (39.1%) and less so for breast (19.2%) cancers.

AIM Gene Signature in Primary Cancers.

Figure 4A:
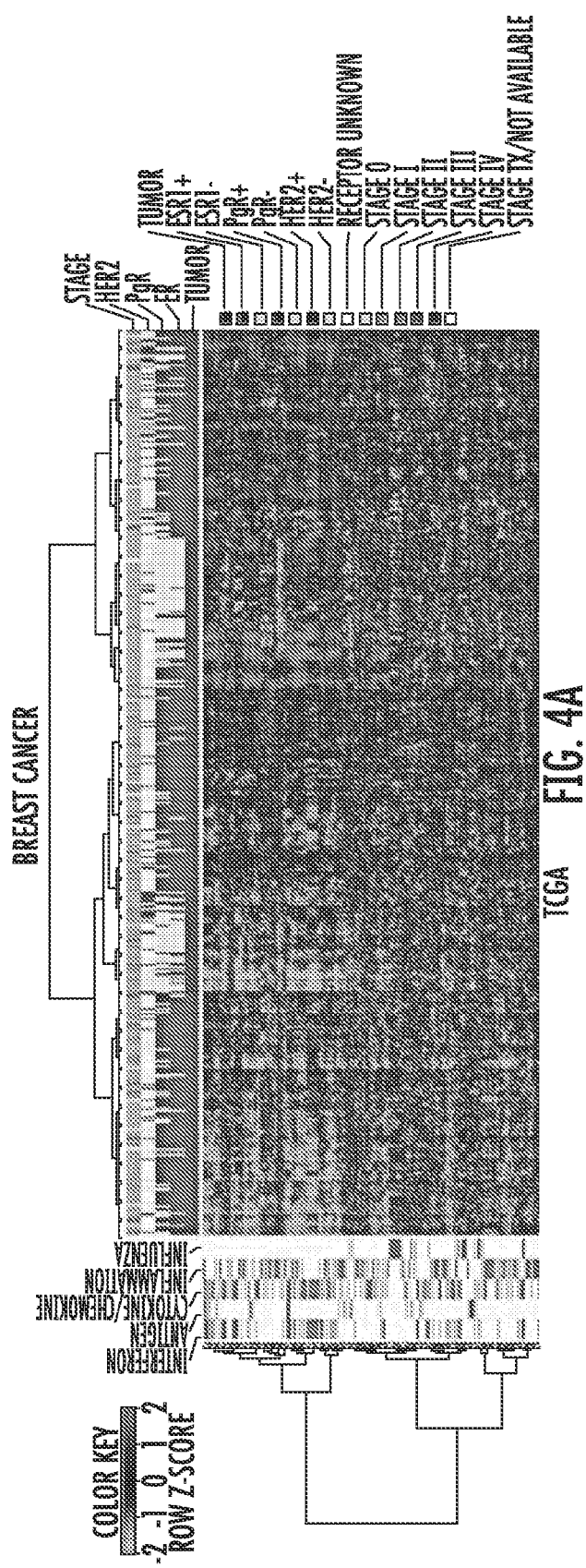
Figure 4B:
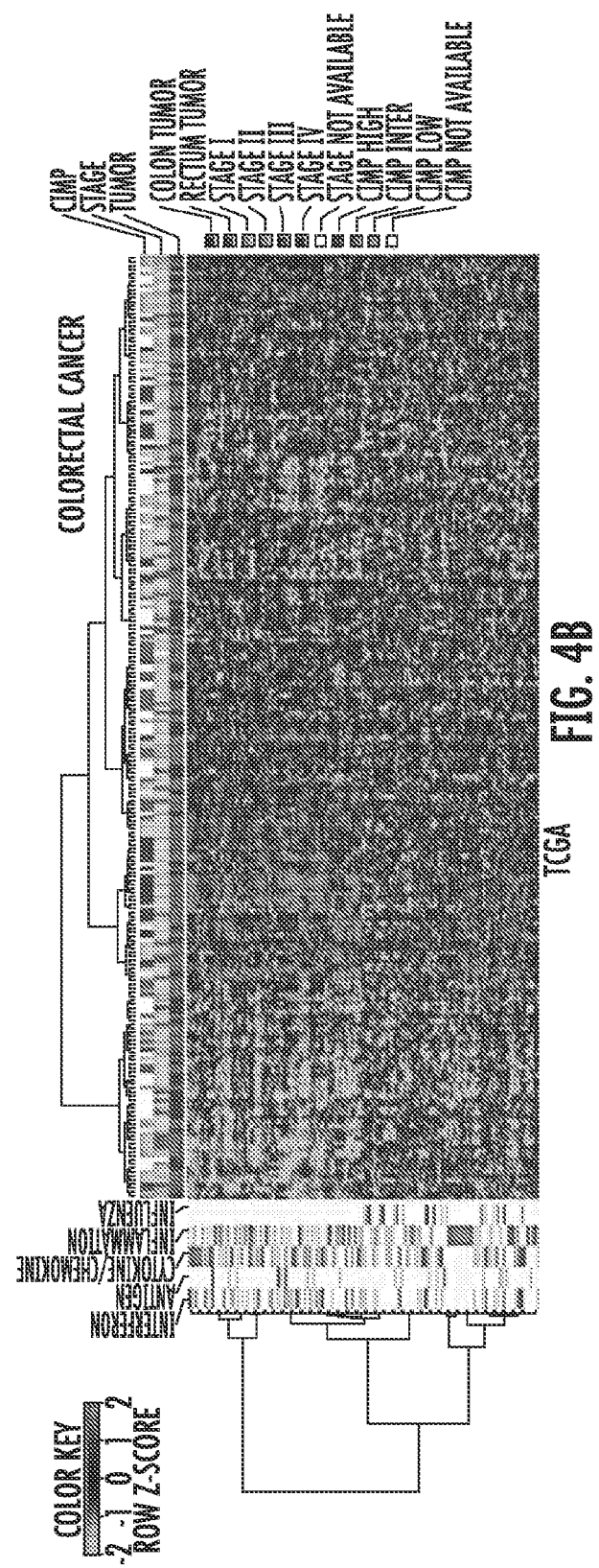
Figure 4C:
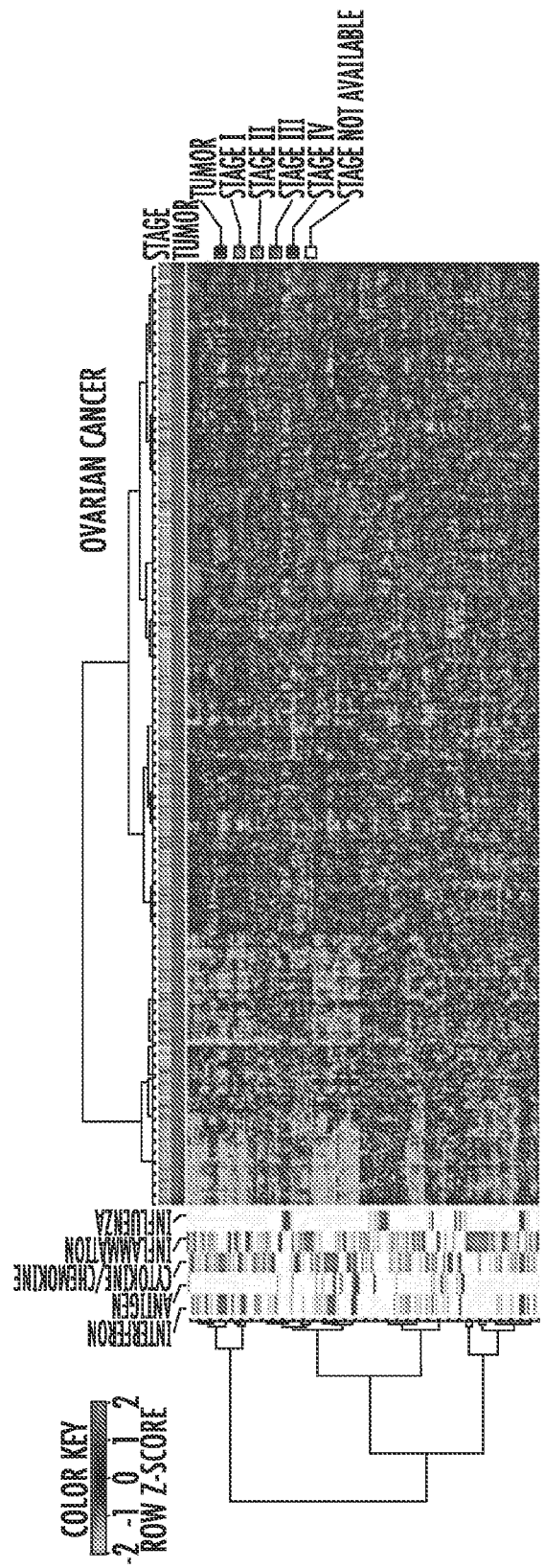
Figure 4F:
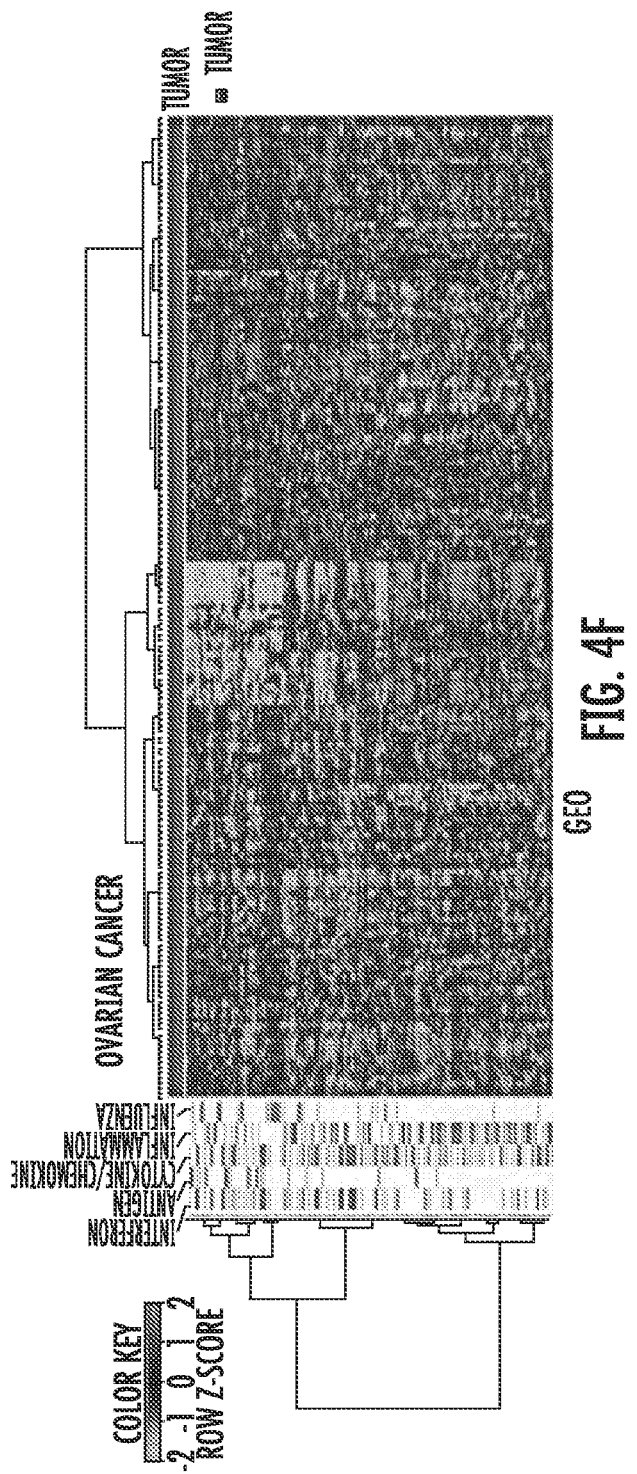

It is critical to know how all of the above work performed in cultured cancer cells may relate to primary cancers. We thus examined how basal levels of the AIM genes might reveal clustering of hundreds of primary samples in publicly available gene expression data sets from breast, colorectal, and ovarian cancers in The Cancer Genome Atlas (TCGA) and the Gene Expression Omnibus (GEO) (FIG. 4) (TCGA datasets included 536 breast, 155/69 colon/rectal and 590 ovarian cancers, and for GEO the breast, colorectal and ovarian datasets contained 177,188 and 185 cancers, respectively). Significantly, each cancer type, in each database, clustered into sub-groups that have very concordant "low" or "high" expression of the 317 AIM genes (FIG. 4). For the TCGA data, no correlation was observed with clinical stage or tumor subtype in either breast, colorectal or ovarian cancers (FIG. 4A, B, C). These clinical parameters were less well defined in GEO. We also did not see an association of AIM gene expression with breast cancer subtype (ER+, HER2+, triple negative) (FIG. 4A,D). Because of the smaller number of colon cancers in the TCGA, both colon and rectal cancer expression data were combined for the AIM analysis and we found that there was no distinct cluster associated with either tissue type (colon or rectal). However, higher AIM gene expression did appear to associate with a large percentage of colorectal tumors that had a high CIMP status (FIG. 4B).

Taken together, these data suggest that the low basal levels of the AIM genes in primary cancers of all three types suggests what has been termed a cancer immune evasion phenotype, which can be reversed by AZA treatment. Our previous data with NSCLC with a less comprehensively annotated gene set had also suggested this. We thus examined our AIM gene panel in the TCGA data set for NSCLC. Remarkably, TCGA expression data from lung cancers showed similar clustering of AIM gene sets into a "high" and "low" expression cluster (FIG. 11A). We also examined our AIM profile in the TCGA melanoma database since excitement over targeting immune tolerance for solid tumors has been particularly high for this disease. Again, an intriguing clustering of AIM gene sets into a "high" and "low" expression cluster is seen (FIG. 11B).

Figure 5C:
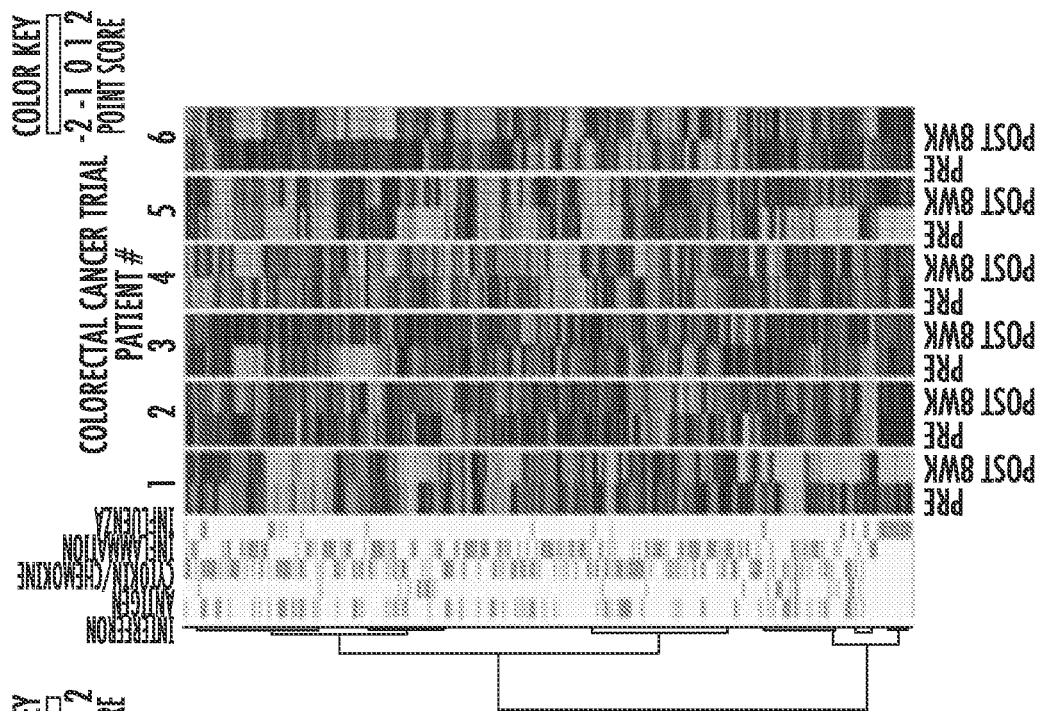
Figure 5B:
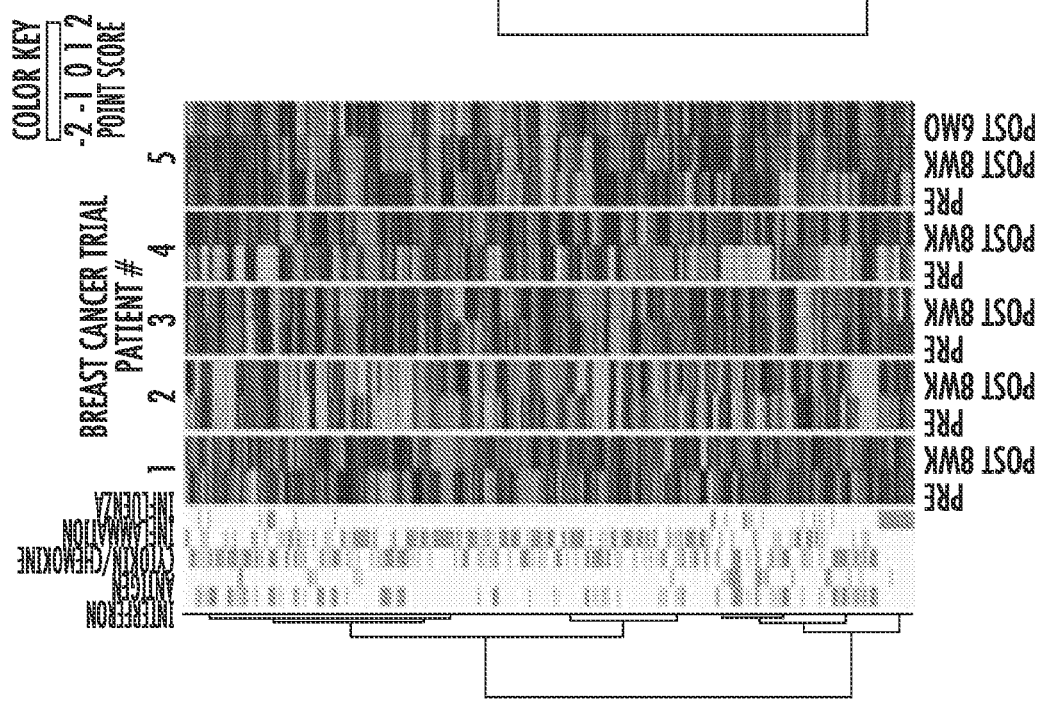
Figure 5D:
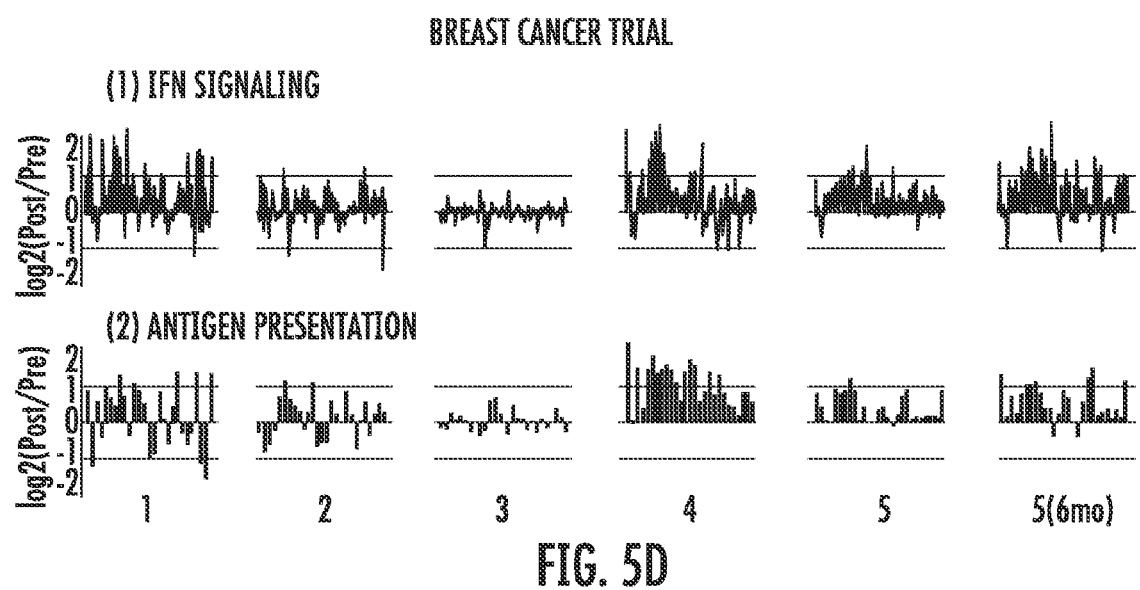
Figure 5E:
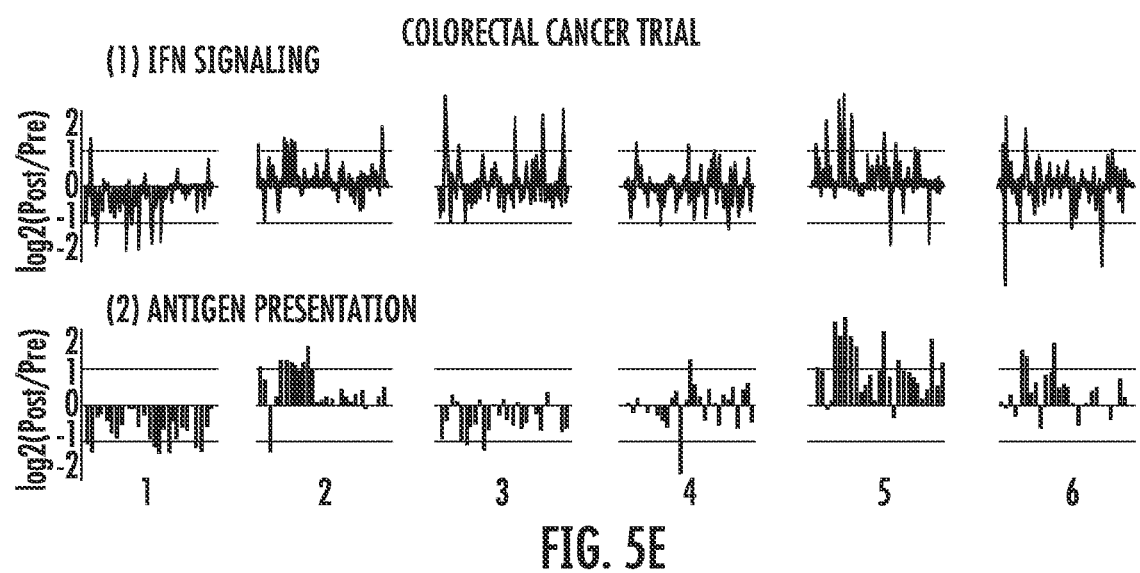

To address the question of whether AIM genes are re-expressed in vivo, we queried RNA from patients receiving combination epigenetic therapy with AZA and an HDAC inhibitor, entinostat, for patients with triple negative breast cancer and colorectal cancer with the AIM panel. We examined biopsies obtained from patients pre- and post-(8-weeks) epigenetic therapy. GSEA analysis of expression data from paired patient biopsies revealed that 32.7% (33/101) of the GSEA gene sets upregulated in breast cancers were immune related while colorectal cancers contained 11.9% (56/469) upregulated immune gene sets (FIG. 5a). Of the 15 common upregulated immune gene sets from the 63 AZA treated cancer cell lines (FIG. 1C), strikingly 11 immune gene sets were upregulated in biopsies from both breast and colorectal patients after 8 weeks of therapy. The 317 AIM genes derived from our cell line experiments were used to query the expression data from the paired biopsies, and AIM genes were upregulated by AZA in the post treatment tissue (FIG. 5B,C). For example, breast cancer patient #5 showed increased expression of AIM genes at 8 weeks of AZA/ Entinostat therapy and this increase was maintained, if not increased, in a 6 month biopsy (FIG. 5B). This patient showed significant fold change expression for the interferon signaling ($\alpha/\beta$ and $\gamma$) gene sets in the AIM panel (FIG. 5D). Similarly breast cancer patients 1 and 4 also showed strong increases in the AIM gene panel and again for interferon signaling expression in response to combination epigenetic therapy with AZA and entinostat (FIG. 5B,D). Similarly, colorectal cancer patients 2, 5 and 6 showed increases in AIM gene expression in the 8 week post biopsy (FIG. 5C) especially for individual AIM gene sets such as antigen presentation (FIG. 5E).

In this study, we investigated a response to an important epigenetic agent, the DNA demethylating drug, AZA, in three common solid tumors. This is an important issue because AZA is FDA approved for MDS, and given at low doses which preserve on-target effects and minimize off target ones, its promise for efficacy in solid tumors is emerging. In our pre-clinical studies of cell lines from breast, colorectal, and ovarian tumors, transient, low-dose AZA alters many pathways key for tumorigenesis including cell cycle and mitotic pathways, mRNA splicing and translation, transcription and DNA replication. However, the dominant effect was an upregulation of immunomodulatory pathways. The importance of these findings to the emerging possibility of a role for epigenetic therapy for sensitizing patients with cancer to immunotherapy has been stressed throughout our manuscript.

Importantly, we have highlighted two ways in which our cell culture data have key relationships to primary tumors for not only the three cancer types studied but also for NSCLC and melanoma. First, the AIM gene panel we have generated clusters basal expression levels for hundreds of primary samples across five tumor types and multiple expression databases into high and low immune gene expression groups. With the close relationship of the involved genes to key immune pathways such as interferon responses to inflammation, viral challenge, etc., low levels of the AIM genes represent cancers with what has been termed an immune evasion signature. In fact, previous studies have described immune enriched subtypes in several types of solid tumors including triple negative breast cancer, colon cancer, and an "immunoreactive subtype" of serous ovarian carcinoma.

Taken together, these data show that solid tumors can be described as immune low or immune enriched and suggests that patients with low expression of immune AIM genes might benefit most from receiving epigenetic therapy prior to immunotherapy. Our pan-cancer data would, then, provide a rich roadmap for a biomarker strategy that might track, and help personalize, such a scenario. Second, for the above biomarker implications, although the patient numbers are low and immunotherapy was not given, we have provided evidence that genes in our AIM panel are upregulated by epigenetic therapy in patient tumor biopsy samples for two of the cancer types studied, breast and colorectal cancer.

A question that remains to be answered in our study is the role that AZA is playing in regulating the observed changes in gene expression signatures. Classically, this drug blocks DNA methylation, and this could lead to re-expression of promoter methylated and silenced genes. While we believe this certainly is contributing to the immune response observed, most of the AIM genes do not have canonical CpG island promoters.

Many key pathway changes for anti-tumor responses, and perhaps most gene expression changes including AIM genes, may lie downstream of a hub triggered in a cancer cell by classic promoter demethylation. Furthermore, for the low AZA doses employed, we see significant overall DNA demethylation (FIG. 8) and specific events for key genes in our immune pathways (FIG. 8). A key example in this work with high correlation to AIM gene responses, and to events in the interferon pathway in our previous study of NSCLC is for the transcription factor gene, IRF7.

This will especially hold true for the low doses of AZA that are used in clinical trials with epigenetic therapy. Low doses of AZA which we have shown are effective in solid tumors may not effectively re-express all densely hypermethylated genes as high doses of demethylating agents can. Interestingly, most of the immune genes in our AIM panel do not have CpG island promoters and the epigenetic mechanism controlling their re-expression is not clear. However the increase in gene expression could be related to the scaffolding actions of DNMT1 and how AZA induced degradation of this methyltransferase could affect the binding of other chromatin regulators, thereby leading to chromatin remodeling and increased transcription. The targeted role of AZA on degrading DNMTs is highly reflected in the very similar responses of these AIM genes to genetic depletion of DNMT's in the DKO cells (FIG. 9).

Our pre-clinical studies using AZA initially derived the AIM gene panel from cultured epithelial cancer cells, and although it seems likely that the increased immune signature in patient biopsies treated with AZA/Entinostat is coming from the tumor cells, the immune signature may also be influenced by drug effects on stroma, and infiltrating immune cells. HDAC inhibitors have been shown to have effects on the host immune system. Our pre-clinical TSA data shows that in epithelial cells HDAC inhibitors also regulate a significant number of immune genes. A compelling question remains about the relative contributions of each drug type to regulation of gene expression in epithelial versus host/immune cells. These results suggest why a combination of AZA and an HDACi, as used in our ongoing NSCLC trials, may be an optimal approach in the clinic.

Our current findings showing a universal upregulation of immune genes by epigenetic drugs in multiple solid tumor types indicate a strong immunomodulatory role for these drugs in cancers. Our derived AIM gene panel identifies the subset of patients with a low basal immune gene expression signature that may derive the greatest benefit from a combination of epigenetic priming for immune therapy.

I. Definitions

As used herein, the term "antibody" is used in reference to any immunoglobulin molecule that reacts with a specific antigen. It is intended that the term encompass any immunoglobulin (e.g., IgG, IgM, IgA, IgE, IgD, etc.) obtained from any source (e.g., humans, rodents, non-human primates, caprines, bovines, equines, ovines, etc.). Specific types/examples of antibodies include polyclonal, monoclonal, humanized, chimeric, human, or otherwise-human-suitable antibodies. "Antibodies" also includes any fragment or derivative of any of the herein described antibodies.

As used herein, the term "antigen" is generally used in reference to any substance that is capable of reacting with an antibody. More specifically, as used herein, the term "antigen" refers to a biomarker described herein. An antigen can also refer to a synthetic peptide, polypeptide, protein or fragment of a polypeptide or protein, or other molecule which elicits an antibody response in a subject, or is recognized and bound by an antibody.

As used herein, the term "biomarker" refers to a molecule that is associated either quantitatively or qualitatively with a biological change. Examples of biomarkers include polynucleotides, such as a gene product, RNA or RNA fragment; proteins, polypeptides, and fragments of a polypeptide or protein. In certain embodiments, a "biomarker" means a molecule/compound that is differentially present (i.e., increased or decreased) in a biological sample as measured/compared against the same marker in another biological sample or control/reference. In other embodiments, a biomarker can be differentially present in a biological sample as measured/compared against the other markers in same or another biological sample or control/reference. In further embodiments, one or more biomarkers can be differentially present in a biological sample as measured/compared against other markers in the same or another biological sample or control/reference and against the same markers in another biological sample or control/reference. In yet another embodiment, a biomarker can be differentially present in a biological sample from a subject or a group of subjects having a first phenotype (e.g., having a disease or condition) as compared to a biological sample from a subject or group of subjects having a second phenotype (e.g., not having the disease or condition or having a less severe version of the disease or condition).

In general, the one or more biomarkers can be generally present at a level that is increased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more; or is generally present at a level that is decreased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent). A biomarker is preferably differentially present at a level that is statistically significant (e.g., a p-value less than 0.05 and/or a q-value of less than 0.10 as determined using, for example, either Welch's T-test or Wilcoxon's rank-sum Test). Biomarker levels can be used in conjunction with other parameters to assess a patient.

As used herein, the term "comparing" refers to making an assessment of how the proportion, level or cellular localization of one or more biomarkers in a sample from a patient relates to the proportion, level or cellular localization of the corresponding one or more biomarkers in a standard, reference or control sample. For example, "comparing" may refer to assessing whether the proportion, level, or cellular localization of one or more biomarkers in a sample from a patient is the same as, more or less than, or different from the proportion, level, or cellular localization of the corresponding one or more biomarkers in standard, reference or control sample. In particular embodiments, the term may refer to assessing whether the proportion, level, or cellular localization of one or more biomarkers in a sample from a patient is the same as, more or less than, different from or otherwise corresponds (or not) to the proportion, level, or cellular localization of predefined biomarker levels/ratios that correspond to, for example, high or low AIM level. In another specific embodiment, the term "comparing" refers to assessing whether the level of one or more biomarkers of the present invention in a sample from a patient is the same as, more or less than, different from other otherwise correspond (or not) to levels/ratios of the same biomarkers in a control sample (e.g., predefined levels/ratios that correlate to high or low AIM levels).

In another embodiment, the term "comparing" refers to making an assessment of how the proportion, level or cellular localization of one or more biomarkers in a sample from a patient relates to the proportion, level or cellular localization of one or more biomarkers in the same sample. For example, a ratio of one biomarker to another (or more) from the same patient sample can be compared. Percentages or ratios of expression or levels of the biomarkers can be compared to other percentages or ratios in the same sample and/or to predefined reference or control percentages or ratios. Such comparison can be made to assess whether the patient's immune signature is AIM-high or AIM-low, which assessment can be used to direct therapy.

In embodiments in which the relationship of the biomarkers are described in terms of a ratio, the ratio can include 1-fold, 2-, 3-, 4-, 5-, 6-, 7-, 8-, 9-, 10-, 11-, 12-, 13-, 14-, 15-, 16-, 17-, 18-, 19-, 20-, 21-, 22-, 23-, 24-, 25-, 26-, 27-, 28-, 29-, 30-, 31-, 32-, 33-, 34-, 35-, 36-, 37-, 38-, 39-, 40-, 41-, 42-, 43-, 44-, 45-, 46-, 47-, 48-, 49-, 50-, 51-, 52-, 53-, 54-, 55-, 56-, 57-, 58-, 59-, 60-, 61-, 62-, 63-, 64-, 65-, 66-, 67-, 68-, 69-, 70-, 71-, 72-, 73-, 74-, 75-, 76-, 77-, 78-, 79-, 80-, 81-, 82-, 83-, 84-, 85-, 86-, 87-, 88-, 89-, 90-, 91-, 92-, 93-, 94-, 95-, 96-, 97-, 98-, 99-, 100-fold or more difference (higher or lower). Alternatively, the difference can include 0.9-fold, 0.8-fold, 0.7-fold, 0.7-fold, 0.6-fold, 0.5-fold, 0.4-fold, 0.3-fold, 0.2-fold, and 0.1-fold (higher or lower) depending on context. The foregoing can also be expressed in terms of a range (e.g., 1-5 fold/times higher or lower) or a threshold (e.g., at least 2-fold/times higher or lower).

The evaluation of the relationship between one or more biomarkers in a sample (e.g., one or more biomarkers compared to one or more other biomarkers (perhaps in combination with internal standards expression or levels (e.g., actin)) can also be expressed in terms of a percentage including, but not limited to, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 150%, 200% or more (higher or lower) difference. The foregoing can also be expressed in terms of a range (e.g., 50-100% higher or lower) or a threshold (e.g., at least 50% higher or lower)

As used herein, the terms "identifies," "indicates" or "correlates" (or "identifying," "indicating" or "correlating," or "identification," "indication" or "correlation," depending on the context) in reference to a parameter, e.g., a modulated proportion, level, or cellular localization in a sample from a patient, may mean that the patient has a particular immune signature, e.g., AIM high or AIM low. In specific embodiments, the parameter may comprise the level (expression level or protein level) of one or more biomarkers of the present invention. A particular set or pattern of the amounts of one or more biomarkers may identify the patient as having a particular immune signature, e.g., AIM high or AIM low In certain embodiments, "identifying," "indicating," or "correlating," as used according to the present invention, may be by any linear or non-linear method of quantifying the relationship between levels/ratios of biomarkers to other biomarkers and/or standard, control or comparative value for the assessment of an immune signature.

The terms "patient," "individual," or "subject" are used interchangeably herein, and refer to a mammal, particularly, a human. The patient may have mild, intermediate or severe disease. The patient may be treatment naïve, responding to any form of treatment, or refractory. The patient may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates.

The terms "measuring" and "determining" are used interchangeably throughout, and refer to methods which include obtaining a patient sample and/or detecting the level of a biomarker(s) in a sample. In one embodiment, the terms refer to obtaining a patient sample and detecting the level of one or more biomarkers in the sample. In another embodiment, the terms "measuring" and "determining" mean detecting the level of one or more biomarkers in a patient sample. Measuring can be accomplished by methods known in the art and those further described herein. The terms are also used interchangeably throughout with the term "detecting."

The terms "sample," "patient sample," "biological sample," and the like, encompass a variety of sample types obtained from a patient, individual, or subject and can be used in a diagnostic or monitoring assay. The patient sample may be obtained from a healthy subject, a diseased patient or a patient having associated symptoms of cancer. Moreover, a sample obtained from a patient can be divided and only a portion may be used for diagnosis. Further, the sample, or a portion thereof, can be stored under conditions to maintain sample for later analysis. The definition specifically encompasses solid tissue samples such as a biopsy specimen or tissue cultures or cells derived therefrom and the progeny thereof. In other embodiments, the term sample includes blood and other liquid samples of biological origin (including, but not limited to, peripheral blood, serum, plasma, cerebrospinal fluid, urine, saliva, stool and synovial fluid). In a specific embodiment, a sample comprises a tumor sample.

The definition of "sample" also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry. In certain embodiments, a sample comprises an optimal cutting temperature (OCT)-embedded frozen tissue sample.

As used herein, the term "predetermined threshold value" of a biomarker refers to the level of the same biomarker in a corresponding control/normal sample or group of control/normal samples. Further, the term "altered level" of a biomarker in a sample refers to a level that is either below or above the predetermined threshold value for the same biomarker and thus encompasses either high (increased) or low (decreased) levels.

As used herein, the terms "binding agent specific for" or "binding agent that specifically binds" refers to an agent that binds to a biomarker and does not significantly bind to unrelated compounds. Examples of binding agents that can be effectively employed in the disclosed methods include, but are not limited to, lectins, proteins and antibodies, such as monoclonal or polyclonal antibodies, or antigen-binding fragments thereof, aptamers, etc. In certain embodiments, a binding agent binds a biomarker with an affinity constant of, for example, greater than or equal to about $1 \times 10^{-6}$ M. A binding agent can also comprise a probe or primer that specifically hybridizes a biomarker nucleic acid.

The terms "specifically binds to," "specific for," and related grammatical variants refer to that binding which occurs between such paired species as enzyme/substrate, receptor/agonist, antibody/antigen, nucleic acid/complement and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody typically binds to a single epitope and to no other epitope within the family of proteins. In some embodiments, specific binding between an antigen and an antibody will have a binding affinity of at least $10^{-6}$ M. In other embodiments, the antigen and antibody will bind with affinities of at least $10^{-7}$ M, $10^{-8}$ M to $10^{-9}$ M, $10^{-10}$ M, $10^{-11}$ M, or $10^{-12}$ M.

Various methodologies of the instant invention include a step that involves comparing a value, level, feature, characteristic, property, etc. to a "suitable control," referred to interchangeably herein as an "appropriate control," a "control sample" or a "reference." A "suitable control," "appropriate control," "control sample" or a "reference" is any control or standard familiar to one of ordinary skill in the art useful for comparison purposes. In one embodiment, a "suitable control" or "appropriate control" is a value, level, feature, characteristic, property, etc., determined in a cell, organ, or patient, e.g., a control cell, organ, or patient, exhibiting, for example, a particular immune signature. In another embodiment, a "suitable control" or "appropriate control" is a value, level, feature, characteristic, property, ratio, etc. (e.g., biomarker levels that correlate to a particular immune signature) determined prior to performing a therapy (e.g., cancer treatment) on a patient. In yet another embodiment, a transcription rate, mRNA level, translation rate, protein level/ratio, biological activity, cellular characteristic or property, genotype, phenotype, etc., can be determined prior to, during, or after administering a therapy into a cell, organ, or patient. In a further embodiment, a "suitable control," "appropriate control" or a "reference" is a predefined value, level, feature, characteristic, property, ratio, etc. A "suitable control" can be a profile or pattern of levels/ratios of one or more biomarkers of the present invention that correlates to a particular immune signature, to which a patient sample can be compared. The patient sample can also be compared to a negative control. Such reference levels may also be tailored to specific techniques that are used to measure levels of biomarkers in biological samples (e.g., LC-MS, GC-MS, ELISA, PCR, etc.), where the levels of biomarkers may differ based on the specific technique that is used. In particular embodiments, a control or reference can be a profile or pattern of levels of one or more biomarkers that correlates to a particular immune signature, e.g., AIM high or AIM low.

II. Methods to Measure the Level of Target Biomarker Nucleic Acids

Many methods of measuring the levels or amounts of biomarker nucleic acid expression are contemplated. Any reliable, sensitive, and specific method can be used. In particular embodiments, biomarker nucleic acid is amplified prior to measurement. In other embodiments, the level of biomarker nucleic acid is measured during the amplification process. In still other methods, the target nucleic acid is not amplified prior to measurement.

A. Amplification Reactions

Many methods exist for amplifying nucleic acid sequences. Suitable nucleic acid polymerization and amplification techniques include reverse transcription (RT), polymerase chain reaction (PCR), real-time PCR (quantitative PCR (q-PCR)), nucleic acid sequence-base amplification (NASBA), ligase chain reaction, multiplex ligatable probe amplification, invader technology (Third Wave), rolling circle amplification, in vitro transcription (IVT), strand displacement amplification, transcription-mediated amplification (TMA), RNA (Eberwine) amplification, and other methods that are known to persons skilled in the art. In certain embodiments, more than one amplification method is used, such as reverse transcription followed by real time quantitative PCR (qRT-PCR). See, e.g., Chen et al., 33(20) NUCL. ACIDS RES. e179 (2005).

A typical PCR reaction comprises multiple amplification steps or cycles that selectively amplify target nucleic acid species including a denaturing step in which a target nucleic acid is denatured; an annealing step in which a set of PCR primers (forward and reverse primers) anneal to complementary DNA strands; and an extension step in which a thermostable DNA polymerase extends the primers. By repeating these steps multiple times, a DNA fragment is amplified to produce an amplicon, corresponding to the target DNA sequence. Typical PCR reactions include about 20 or more cycles of denaturation, annealing, and extension. In many cases, the annealing and extension steps can be performed concurrently, in which case the cycle contains only two steps. Because mature mRNA are single-stranded, a reverse transcription reaction (which produces a complementary cDNA sequence) may be performed prior to PCR reactions. Reverse transcription reactions include the use of, e.g., a RNA-based DNA polymerase (reverse transcriptase) and a primer.

In PCR and q-PCR methods, for example, a set of primers is used for each target sequence. In certain embodiments, the lengths of the primers depends on many factors, including, but not limited to, the desired hybridization temperature between the primers, the target nucleic acid sequence, and the complexity of the different target nucleic acid sequences to be amplified. In certain embodiments, a primer is about 15 to about 35 nucleotides in length. In other embodiments, a primer is equal to or fewer than about 15, fewer than about 20, fewer than about 25, fewer than about 30, or fewer than about 35 nucleotides in length. In additional embodiments, a primer is at least about 35 nucleotides in length.

In a further embodiment, a forward primer can comprise at least one sequence that anneals to biomarker nucleic acid sequence and alternatively can comprise an additional 5' non-complementary region. In another embodiment, a reverse primer can be designed to anneal to the complement of a reverse transcribed mRNA. The reverse primer may be independent of the biomarker nucleic acid sequence, and multiple biomarker nucleic acid sequences may be amplified using the same reverse primer. Alternatively, a reverse primer may be specific for a biomarker nucleic acid.

In some embodiments, two or more biomarker nucleic acid sequences are amplified in a single reaction volume. One aspect includes multiplex q-PCR, such as qRT-PCR, which enables simultaneous amplification and quantification of at least two biomarker nucleic acid sequences of interest in one reaction volume by using more than one pair of primers and/or more than one probe. The primer pairs comprise at least one amplification primer that uniquely binds each mRNA, and the probes are labeled such that they are distinguishable from one another, thus allowing simultaneous quantification of multiple biomarker nucleic acid sequences. Multiplex qRT-PCR has research and diagnostic uses including, but not limited, to detection of biomarker nucleic acid sequences for diagnostic, prognostic, and therapeutic applications.

The qRT-PCR reaction may further be combined with the reverse transcription reaction by including both a reverse transcriptase and a DNA-based thermostable DNA polymerase. When two polymerases are used, a "hot start" approach may be used to maximize assay performance. See U.S. Pat. Nos. 5,985,619 and 5,411,876. For example, the components for a reverse transcriptase reaction and a PCR reaction may be sequestered using one or more thermoactivation methods or chemical alteration to improve polymerization efficiency. See U.S. Pat. Nos. 6,403,341; 5,550,044; and 5,413,924.

B. Detection of Target Biomarker Nucleic Acids

In certain embodiments, labels, dyes, or labeled probes and/or primers are used to detect amplified or unamplified biomarker nucleic acid sequence (mRNA/cDNA). One of ordinary skill in the art will recognize which detection methods are appropriate based on the sensitivity of the detection method and the abundance of the target. Depending on the sensitivity of the detection method and the abundance of the target, amplification may or may not be required prior to detection. One skilled in the art will recognize the detection methods where biomarker nucleic acid sequence amplification is preferred.

A probe or primer may include Watson-Crick bases or modified bases. Modified bases include, but are not limited to, the AEGIS bases (from EraGen Biosciences, Inc. (Madison, Wis.)), which have been described, e.g., in U.S. Pat. Nos. 6,001,983; 5,965,364; and 5,432,272. In certain aspects, bases are joined by a natural phosphodiester bond or a different chemical linkage. Different chemical linkages include, but are not limited to, a peptide bond or a Locked Nucleic Acid (LNA) linkage, which is described, e.g., in U.S. Pat. No. 7,060,809.

In a further aspect, oligonucleotide probes or primers present in an amplification reaction are suitable for monitoring the amount of amplification product produced as a function of time. In certain aspects, probes having different single stranded versus double stranded character are used to detect the nucleic acid. Probes include, but are not limited to, the 5'-exonuclease assay (e.g., TaqMan®) probes (see U.S. Pat. No. 5,538,848), stem-loop molecular beacons (see, e.g., U.S. Pat. Nos. 6,103,476 and 5,925,517), stemless or linear beacons (see, e.g., WO 9921881, U.S. Pat. Nos. 6,649,349 and 6,485,901), peptide nucleic acid (PNA) Molecular Beacons (see, e.g., U.S. Pat. Nos. 6,593,091 and 6,355,421), linear PNA beacons (see, e.g., U.S. Pat. No. 6,329,144), non-FRET probes (see, e.g., U.S. Pat. No. 6,150,097), Sunrise®/Amplifluor® probes (see, e.g., U.S. Pat. No. 6,548,250), stem-loop and duplex Scorpion™ probes (see, e.g., U.S. Pat. No. 6,589,743), bulge loop probes (see, e.g., U.S. Pat. No. 6,590,091), pseudo knot probes (see, e.g., U.S. Pat. No. 6,548,250), cyclicons (see, e.g., U.S. Pat. No. 6,383,752), MGB Eclipse® probe (Sigma-Aldrich Corp. (St. Louis, Mo.)), hairpin probes (see, e.g., U.S. Pat. No. 6,596,490), PNA light-up probes, antiprimer quench probes (Li et al., 53 CLIN. CHEM. 624-33 (2006)), self-assembled nanoparticle probes, and ferrocene-modified probes described, for example, in U.S. Pat. No. 6,485,901.

In certain embodiments, one or more of the primers in an amplification reaction can include a label. In yet further embodiments, different probes or primers comprise detectable labels that are distinguishable from one another. In some embodiments a nucleic acid, such as the probe or primer, may be labeled with two or more distinguishable labels.

In some aspects, a label is attached to one or more probes and has one or more of the following properties: (i) provides a detectable signal; (ii) interacts with a second label to modify the detectable signal provided by the second label, e.g., FRET (Fluorescent Resonance Energy Transfer); (iii) stabilizes hybridization, e.g., duplex formation; and (iv) provides a member of a binding complex or affinity set, e.g., affinity, antibody-antigen, ionic complexes, hapten-ligand (e.g., biotin-avidin). In still other aspects, use of labels can be accomplished using any one of a large number of known techniques employing known labels, linkages, linking groups, reagents, reaction conditions, and analysis and purification methods.

Biomarker nucleic acid sequences can be detected by direct or indirect methods. In a direct detection method, one or more biomarker nucleic acid sequences are detected by a detectable label that is linked to a nucleic acid molecule. In such methods, the biomarker nucleic acid sequences may be labeled prior to binding to the probe. Therefore, binding is detected by screening for the labeled biomarker nucleic acid sequence that is bound to the probe. The probe is optionally linked to a bead in the reaction volume.

In certain embodiments, nucleic acids are detected by direct binding with a labeled probe, and the probe is subsequently detected. In one embodiment of the invention, the nucleic acids, such as amplified mRNA/cDNA, are detected using xMAP Microspheres (Luminex Corp. (Austin, Tex.)) conjugated with probes to capture the desired nucleic acids. Some methods may involve detection with polynucleotide probes modified, for example, with fluorescent labels or branched DNA (bDNA) detection.

In other embodiments, nucleic acids are detected by indirect detection methods. For example, a biotinylated probe may be combined with a stretavidin-conjugated dye to detect the bound nucleic acid. The streptavidin molecule binds a biotin label on amplified nucleic acid, and the bound nucleic acid is detected by detecting the dye molecule attached to the streptavidin molecule. In one embodiment, the streptavidin-conjugated dye molecule comprises Phycolink® Streptavidin R-Phycoerythrin (ProZyme, Inc. (Heward, Calif.)). Other conjugated dye molecules are known to persons skilled in the art.

Labels include, but are not limited to, light-emitting, light-scattering, and light-absorbing compounds which generate or quench a detectable fluorescent, chemiluminescent, or bioluminescent signal. See, e.g., Garman A., Non-Radioactive Labeling, Academic Press (1997) and Kricka, L., Nonisotopic DNA Probe Techniques, Academic Press, San Diego (1992). Fluorescent reporter dyes useful as labels include, but are not limited to, fluoresceins (see, e.g., U.S. Pat. Nos. 6,020,481; 6,008,379; and 5,188,934), rhodamines (see, e.g., U.S. Pat. Nos. 6,191,278; 6,051,719; 5,936,087; 5,847,162; and 5,366,860), benzophenoxazines (see, e.g., U.S. Pat. No. 6,140,500), energy-transfer fluorescent dyes, comprising pairs of donors and acceptors (see, e.g., U.S. Pat. Nos. 5,945,526; 5,863,727; and 5,800,996; and), and cyanines (see, e.g., WO 9745539), lissamine, phycoerythrin, Cy2, Cy3, Cy3.5, Cy5, Cy5.5, Cy7, FluorX (Amersham Biosciences, Inc. (Piscataway, N.J.)), Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, Tetramethylrhodamine, and/or Texas Red, as well as any other fluorescent moiety capable of generating a detectable signal. Examples of fluorescein dyes include, but are not limited to, 6-carboxyfluorescein; 2',4',1,4-tetrachlorofluorescein, and 2',4',5',7',1,4-hexachlorofluorescein. In certain aspects, the fluorescent label is selected from SYBR-Green, 6-carboxyfluorescein ("FAM"), TET, ROX, VICTM, and JOE. For example, in certain embodiments, labels are different fluorophores capable of emitting light at different, spectrally-resolvable wavelengths (e.g., 4-differently colored fluorophores); certain such labeled probes are known in the art and described above, and in U.S. Pat. No. 6,140,054. A dual labeled fluorescent probe that includes a reporter fluorophore and a quencher fluorophore is used in some embodiments. It will be appreciated that pairs of fluorophores are chosen that have distinct emission spectra so that they can be easily distinguished.

In further embodiments, labels are hybridization-stabilizing moieties which serve to enhance, stabilize, or influence hybridization of duplexes, e.g., intercalators and intercalating dyes (including, but not limited to, ethidium bromide and SYBR-Green), minor-groove binders, and cross-linking functional groups (see, e.g., Blackburn et al., eds. "DNA and RNA Structure" in Nucleic Acids in Chemistry and Biology (1996)).

In further aspects, methods relying on hybridization and/or ligation to quantify biomarker nucleic acid may be used including, but not limited to, oligonucleotide ligation (OLA) methods and methods that allow a distinguishable probe that hybridizes to the target nucleic acid sequence to be separated from an unbound probe. For example, HARP-like probes, as disclosed in U.S. Patent Application Publication No. 2006/0078894 may be used to measure the quantity of target nucleic acid. In such methods, after hybridization between a probe and the targeted nucleic acid, the probe is modified to distinguish the hybridized probe from the unhybridized probe. Thereafter, the probe may be amplified and/or detected. In general, a probe inactivation region comprises a subset of nucleotides within the target hybridization region of the probe. To reduce or prevent amplification or detection of a HARP probe that is not hybridized to its target nucleic acid, and thus allow detection of the target nucleic acid, a post-hybridization probe inactivation step is carried out using an agent which is able to distinguish between a HARP probe that is hybridized to its targeted nucleic acid sequence and the corresponding unhybridized HARP probe. The agent is able to inactivate or modify the unhybridized HARP probe such that it cannot be amplified.

In an additional embodiment of the method, a probe ligation reaction may be used to quantify target biomarker nucleic acid. In a Multiplex Ligation-dependent Probe Amplification (MLPA) technique, pairs of probes which hybridize immediately adjacent to each other on the target nucleic acid are ligated to each other only in the presence of the target nucleic acid. See Schouten et al., 30 NUCL. ACIDS RES. e57 (2002). In some aspects, MLPA probes have flanking PCR primer binding sites. MLPA probes can only be amplified if they have been ligated, thus allowing for detection and quantification of biomarkers.

Furthermore, a sample may also be analyzed by means of a microarray. Microarrays generally comprise solid substrates and have a generally planar surface, to which a capture reagent (also called an adsorbent or affinity reagent) is attached. Frequently, the surface of a microarray comprises a plurality of addressable locations, each of which has the capture reagent (e.g., miRNA probes specific for particular biomarkers) bound there. Many microarrays are described in the art. These include, for example, biochips produced by Asuragen, Inc. (Austin, Tex.); Affymetrix, Inc. (Santa Clara, Calif.); GenoSensor Corp. (Tempe, Ariz.); Invitrogen, Corp. (Carlsbad, Calif.); and Illumina, Inc. (San Diego, Calif.).

In particular embodiments, a method comprises the steps of (a) assaying gene expression levels of one or more AIM genes described herein (e.g., including a panel described herein) in a biological sample obtained from a patient; (b) calculating an immune signature value based on the assayed expression levels. In a specific embodiment, the assay step can comprise PCR amplification. In other embodiments, the method can further comprise generating a report summarizing the gene expression data and/or the immune signature values. In other embodiments, the method may further comprise recommending a particular treatment. For example, an immune signature that is determined to be low in comparison to other biomarkers/control levels indicates that the subject should be treated with epigenetic therapy followed immunotherapy, chemotherapy or some combination of therapy for the particular cancer. Alternatively, an immune signature that is determined to be high in comparison to other biomarkers/control levels indicates that the subject can be treated with immunotherapy (and optionally chemotherapy or some combination of therapy for the particular cancer). The methods listed above include all embodiments of the AIM panels described herein.

III. Methods to Measure the Level of Target Biomarker Polypeptides

A. Detection by Immunoassay

In another aspect, the biomarkers of the present invention may be detected and/or measured by immunoassay. Immunoassay requires biospecific capture reagents, such as antibodies, to capture the biomarkers. Many antibodies are available commercially. Antibodies also can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well-known in the art. Biospecific capture reagents useful in an immunoassay can also include lectins.

The present invention contemplates traditional immunoassays including, for example, sandwich immunoassays including ELISA or fluorescence-based immunoassays, immunoblots, Western Blots (WB), as well as other enzyme immunoassays. Nephelometry is an assay performed in liquid phase, in which antibodies are in solution. Binding of the antigen to the antibody results in changes in absorbance, which is measured. In a SELDI-based immunoassay, a biospecific capture reagent for the biomarker is attached to the surface of an MS probe, such as a pre-activated protein chip array. The biomarker is then specifically captured on the biochip through this reagent, and the captured biomarker is detected by mass spectrometry.

Although antibodies are useful because of their extensive characterization, any other suitable agent (e.g., a lectin, peptide, aptamer or a small organic molecule) that specifically binds a biomarker of the present invention is optionally used in place of the antibody in the above described immunoassays. Aptamers are nucleic acid-based molecules that bind specific ligands. Methods for making aptamers with a particular binding specificity are known as detailed in U.S. Pat. Nos. 5,475,096; 5,670,637; 5,696,249; 5,270,163; 5,707,796; 5,595,877; 5,660,985; 5,567,588; 5,683,867; 5,637,459; and 6,011,020.

In certain embodiments, the levels of the biomarkers employed herein are quantified by immunoassay, such as enzyme-linked immunoassay (ELISA) technology. In specific embodiments, the levels of expression of the biomarkers are determined by contacting the biological sample with antibodies, or antigen binding fragments thereof, that selectively bind to the biomarkers; and detecting binding of the antibodies, or antigen binding fragments thereof, to the biomarkers. In certain embodiments, the binding agents employed in the disclosed methods and compositions are labeled with a detectable moiety. For ease of reference, the term antibody is used in describing binding agents or capture molecules. However, it is understood that reference to an antibody in the context of describing an exemplary binding agent in the methods of the present invention also includes reference to other binding agents including, but not limited to lectins, peptides, aptamers and small organic molecules.

Furthermore, the level of a biomarker in a sample can be assayed by contacting the biological sample with an antibody, or antigen binding fragment thereof, that selectively binds to the target biomarker (referred to as a capture molecule or antibody or a binding agent), and detecting the binding of the antibody, or antigen-binding fragment thereof, to the biomarker. The detection can be performed using a second antibody to bind to the capture antibody complexed with its target biomarker. Kits for the detection of biomarkers as described herein can include pre-coated strip plates, biotinylated secondary antibody, standards, controls, buffers, streptavidin-horse radish peroxidise (HRP), tetramethyl benzidine (TMB), stop reagents, and detailed instructions for carrying out the tests including performing standards.

The present disclosure also provides methods in which the levels of the biomarkers in a biological sample are determined simultaneously. For example, in one embodiment, methods are provided that comprise: (a) contacting a biological sample obtained from the subject with a plurality of binding agents that selectively bind to a plurality of biomarkers disclosed herein for a period of time sufficient to form binding agent-biomarker complexes; (b) detecting binding of the binding agents to the plurality of biomarkers, thereby determining the levels of the biomarkers in the biological sample; and (c) calculating an immune signature value based on the levels of the biomarkers. In other embodiments, the method can further comprise generating a report summarizing the immune signature values. In other embodiments, the method may further comprise recommending a particular treatment. For example, an immune signature that is determined to be low in comparison to other biomarkers/control levels indicates that the subject should be treated with epigenetic therapy followed immunotherapy, chemotherapy or some combination of therapy for the particular cancer. Alternatively, an immune signature that is determined to be high in comparison to other biomarkers/control levels indicates that the subject can be treated with immunotherapy (and optionally chemotherapy or some combination of therapy for the particular cancer).

In a further aspect, the present disclosure provides compositions that can be employed in the disclosed methods. In certain embodiments, such compositions comprise a solid substrate and a plurality of binding agents immobilized on the substrate, wherein each of the binding agents is immobilized at a different, indexable, location on the substrate and the binding agents selectively bind to a plurality of biomarkers disclosed herein. In a specific embodiment, the locations are pre-determined. In other embodiments, kits are provided that comprise such compositions. In certain embodiments, the plurality of biomarkers includes one or more of the biomarkers described herein.

In a related aspect, methods for treating cancer in a patient/subject can comprise the steps of (a) contacting a biological sample obtained from the subject with a composition disclosed herein comprising binding agents for a period of time sufficient to form binding agent-biomarker complexes; (b) detecting binding of the binding agents to a plurality of biomarkers, thereby determining the levels of biomarkers in the biological sample; and (c) determining or calculating an immune signature based on the biomarker levels. In another embodiment, the method can further comprise the step of (d) treating the patient with epigenetic therapy followed by immunotherapy if the immune signature corresponds to an immune low signature or AIM low (Aza-IMmune Low) as described herein or treating the patient with immunotherapy if the immune signature correspond to an immune rich/high signature or AIM high as described herein.

Epigenetic therapy includes treatment with a DNA methyltransferase inhibitor and/or histone deacytelase (HDAC) inhibitors. DNMT inhibitors include, but are not limited to, 5-azacytidine (azacytidine/Vidaza), 5-aza-2'-deoxycytidine (decitabine/Dacogen), and zebularine. Several HDAD inhibitors are known in the art and include, but are not limited to, vorinostat, romidepsin, panobinostat (LBH589), valproic acid, belinostat (PXD101), mocetinostat (MGCD0103), abexinostat (PCI-24781), SB989, entinostat (MS0275), resminostat (4SC-201), givinostat (IF2357), quisinostat (JNJ-26481585), CUDC-101, AR-42, CHR-2845, CHR-3996, 4SC-202, CG200745, ACY-1215, ME-344, sulforaphane, and kevetrin. Cancer immunotherapies include anti-PD-1 antibodies (e.g., Nivolumab) and anti-PD-L1 antibodies. Therapies can also include, but are not limited to, anti EGFR antibodies (e.g., Matuzumab), alemtuzumab (Campeth-1H), bevacizumab (Avastin), brentuximab vedotin, cetuximab (Erbitux), gemtuzumab ozogamicin, ibritumomab tiuxetan (Zevalin), ipilimumab (Yervoy), nimotuzumab, ofatumumab, panitumumab (Vectibix), rituximab, tositumomab, and trastuzumab.

In specific embodiments, the assay performed on the biological sample can comprise contacting the biological sample with one or more capture agents (e.g., antibodies, lectins, peptides, aptamers, etc., combinations thereof) to form a biomarker:capture agent complex. The complexes can then be detected and/or quantified.

In one method, a first capture molecule or binding agent, such as an antibody that specifically binds the biomarker of interest, is immobilized on a suitable solid phase substrate or carrier. The test biological sample is then contacted with the capture antibody and incubated for a desired period of time. After washing to remove unbound material, a second, detection, antibody that binds to a different, non-overlapping, epitope on the biomarker is then used to detect binding of the biomarker to the capture antibody. The detection antibody is preferably conjugated, either directly or indirectly, to a detectable moiety. Examples of detectable moieties that can be employed in such methods include, but are not limited to, cheminescent and luminescent agents; fluorophores such as fluorescein, rhodamine and eosin; radioisotopes; colorimetric agents; and enzyme-substrate labels, such as biotin.

In another embodiment, the assay is a competitive binding assay, wherein labeled biomarker is used in place of the labeled detection antibody, and the labeled biomarker and any unlabeled biomarker present in the test sample compete for binding to the capture antibody. The amount of biomarker bound to the capture antibody can be determined based on the proportion of labeled biomarker detected.

Solid phase substrates, or carriers, that can be effectively employed in such assays are well known to those of skill in the art and include, for example, 96 well microtiter plates, glass, paper, chips and microporous membranes constructed, for example, of nitrocellulose, nylon, polyvinylidene difluoride, polyester, cellulose acetate, mixed cellulose esters and polycarbonate. Suitable microporous membranes include, for example, those described in US Patent Application Publication no. US 2010/0093557 A1. Methods for the automation of immunoassays are well known in the art and include, for example, those described in U.S. Pat. Nos. 5,885,530, 4,981,785, 6,159,750 and 5,358,691.

The presence of several different biomarkers in a test sample can be detected simultaneously using a multiplex assay, such as a multiplex ELISA. Multiplex assays offer the advantages of high throughput, a small volume of sample being required, and the ability to detect different proteins across a board dynamic range of concentrations.

In certain embodiments, such methods employ an array, wherein multiple binding agents (for example capture antibodies) specific for multiple biomarkers are immobilized on a substrate, such as a membrane, with each capture agent being positioned at a specific, pre-determined, location on the substrate. Methods for performing assays employing such arrays include those described, for example, in US Patent Application Publication nos. US2010/0093557A1 and US2010/0190656A1, the disclosures of which are hereby specifically incorporated by reference.

Multiplex arrays in several different formats based on the utilization of, for example, flow cytometry, chemiluminescence or electron-chemiluminesence technology, are well known in the art. Flow cytometric multiplex arrays, also known as bead-based multiplex arrays, include the Cytometric Bead Array (CBA) system from BD Biosciences (Bedford, Mass.) and multi-analyte profiling (xMAP®) technology from Luminex Corp. (Austin, Tex.), both of which employ bead sets which are distinguishable by flow cytometry. Each bead set is coated with a specific capture antibody. Fluorescence or streptavidin-labeled detection antibodies bind to specific capture antibody-biomarker complexes formed on the bead set. Multiple biomarkers can be recognized and measured by differences in the bead sets, with chromogenic or fluorogenic emissions being detected using flow cytometric analysis. In an alternative format, a multiplex ELISA from Quansys Biosciences (Logan, Utah) coats multiple specific capture antibodies at multiple spots (one antibody at one spot) in the same well on a 96-well microtiter plate. Chemiluminescence technology is then used to detect multiple biomarkers at the corresponding spots on the plate.

IV. Determination of a Patient's Immune Signature Status

A. Biomarker Panels

The biomarkers of the present invention can be used in diagnostic tests to assess, determine, and/or qualify (used interchangeably herein) immune signature status in a patient and therefore, direct treatment of the patient. The phrase "immune signature status" includes a high immune signature (AIM high) and a low immune signature (AIM low). Based on this status, further procedures may be indicated, including additional diagnostic tests or therapeutic procedures or regimens.

These and other biomarkers are disclosed herein, and it is understood that when combinations, subsets, interactions, groups, etc., of these biomarkers are disclosed that while specific reference of each various individual and collective combinations and permutation of these compounds may not be explicitly disclosed, each is specifically contemplated and described herein. Thus, if a panel of biomarkers A, B, and C are disclosed as well as a class of biomarkers D, E, and F and an example of a combination panel A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of using the disclosed biomarkers. Thus, if there are a variety of additional steps that can be performed, it is understood that each of these additional steps can be performed with any specific embodiment or combination of embodiments of the disclosed methods.

Accordingly, in one embodiment, the AIM panel comprises one or more of B2M; CD44; GBP1; HLA-B; HLA-C; ICAM1; IRF7; IRF9; MT2A; OAS1; OAS2; OAS3; OASL; STAT1; EGR1; IFI27; IFI6; IFIT1; IFIT2; IFIT3; IFITM1; ISG15; ISG20; MX1; PSMB8; USP18; XAF1; DDX58; HERC5; UBA7; IFIH1; TNFAIP3; CCL2; CCL20; CCL5; CXCL1; CXCL11; CXCL2; CXCL3; CXCL6; CXCR4; IL8; B2M; CD44; CSF2; DDX58; EGR1; GBP1; HERC5; HLA-B; HLA-C; ICAM1; IFI27; IFI6; IFIT1; IFIT2; IFIT3; IFITM1; IL1R2; IRF7; IRF9; ISG15; ISG20; LCK; MT2A; MX1; OAS1; OAS2; OAS3; OASL; PSMB8; STAT1; UBA7; USP18; XAF1; B2M; HLA-B; HLA-C; PSMB8; PSMB9; TAP1; CTSS; NCF2; ALOX5AP; ANKRD1; AOX1; CCL20; CCL26; CCL5; CXCL1; CXCL11; CXCL2; CXCL6; CXCR4; EREG; FOS; HCP5; HLA-B; IL32; IL8; KCNN4; KLRC2; LSP1; LY96; LYST; MX1; NCF2; PAGE1; RSAD2; S100A8; ADM; C4BPB; CTGF; KLK8; MDK; PLAT; SERPINE1; SPRR3; TFPI; THBD; HSP90AA1; RPL26; ATAD2; CABYR; CSAG1; CT45A1; CT45A5; CT47A11; CTAG1A; CTAG2; CTCFL; DDX43; DSCR8; FAM133A; FMR1NB; GAGE7; HORMAD1; IL13RA2; MAEL; MAGEA10; MAGEA12; MAGEA2B; MAGEA4; MAGEA8; MAGEA9; MAGEB2; MAGEB6; MAGEC1; MAGEC2; PAGE1; PAGE2; PAGE5; PLAC1; PRAME; SPANXA1; SPANXB2; SPANXD; SSX1; SSX3; SSX4B; and SSX7. The foregoing includes, for example, combinations of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, and 161 biomarkers. In particular embodiments, the foregoing combinations are common in any of breast, colorectal and ovarian cancer.

In another embodiment, the AIM panel comprises one or more of HLA-DRB1; EIF4E; EIF4G1; NUP35; UBE2L6; GBP2; HLA-A; HLA-DPB1; HLA-F; IFITM2; IFITM3; MX2; UBE2E1; FAS; FASLG; HLA-DMA; HLA-E; GBP5; IFNGR1; IRF6; VCAM1; IL1A; IL1B; IL6; CCL4; PPBP; EIF4E; EIF4G1; HLA-DRB1; LYN; NUP35; UBE2L6; CASP1; GBP2; HLA-A; HLA-DPB1; HLA-F; IFITM2; IFITM3; IL18; IL6R; IL7R; MX2; NFKB2; UBE2E1; CCL28; CCL3; CCL3L3; CXCR7; GBP5; IFNGR1; IL1A; IL1B; IL6; IRF6; NOD2; STAT5A; VCAM1; PSMA3; CALR; HLA-A; HLA-F; PSME2; ITGAV; ADORA2B; ANXA1; AOC3; CAMP; CCL4; NLRP3; WAS; APOBEC3G; BNIP3; CD19; CEBPB; CEBPG; DEFB1; HP; INHBB; KLRC4; LY75; MX2; NMI; SCG2; TCIRG1; TLR3; TPST1; VWF; CCL3; CCL3L3; FOSL1; IL1A; INHBA; NOD2; PLA2G7; PTX3; S100A7; S100A9; TYROBP; DCBLD2; GP9; PROS1; NUP35; RPL38; XPO1; CALR; RPS27; RPS8; ACTL8; CEP55; OIP5; PASD1; PBK; TMEFF2; TTK; CSAG2; CXorf48; GAGE3; GPAT2; LEMD1; LY6K; MAGEA1; MAGEA11; MAGEA6; MAGEB1; PAGE2B; POTEB; POTEG; SSX2; and ZNF165. The foregoing includes, for example, combinations of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, and 130 biomarkers. In particular embodiments, the foregoing combinations are common any two of breast, colorectal and ovarian cancer.

In a further embodiment, the AIM panel comprises one or more of B2M; CD44; GBP1; HLA-B; HLA-C; ICAM1; IRF7; IRF9; MT2A; OAS1; OAS2; OAS3; OASL; STAT1; EGR1; IFI27; IFI6; IFIT1; IFIT2; IFIT3; IFITM1; ISG15; ISG20; MX1; PSMB8; USP18; XAF1; DDX58; HERC5; UBA7; IFIH1; TNFAIP3; CCL2; CCL20; CCL5; CXCL1; CXCL11; CXCL2; CXCL3; CXCL6; CXCR4; IL8; B2M; CD44; CSF2; DDX58; EGR1; GBP1; HERC5; HLA-B; HLA-C; ICAM1; IFI27; IFI6; IFIT1; IFIT2; IFIT3; IFITM1; IL1R2; IRF7; IRF9; ISG15; ISG20; LCK; MT2A; MX1;

OAS1; OAS2; OAS3; OASL; PSMB8; STAT1; UBA7; USP18; XAF1; B2M; HLA-B; HLA-C; PSMB8; PSMB9; TAP1; CTSS; NCF2; ALOX5AP; ANKRD1; AOX1; CCL20; CCL26; CCL5; CXCL1; CXCL11; CXCL2; CXCL6; CXCR4; EREG; FOS; HCP5; HLA-B; IL32; IL8; KCNN4; KLRC2; LSP1; LY96; LYST; MX1; NCF2; PAGE1; RSAD2; S100A8; ADM; C4BPB; CTGF; KLK8; MDK; PLAT; SERPINE1; SPRR3; TFPI; THBD; HSP90AA1; RPL26; ATAD2; CABYR; CSAG1; CT45A1; CT45A5; CT47A11; CTAG1A; CTAG2; CTCFL; DDX43; DSCR8; FAM133A; FMR1NB; GAGE7; HORMAD1; IL13RA2; MAEL; MAGEA10; MAGEA12; MAGEA2B; MAGEA4; MAGEA8; MAGEA9; MAGEB2; MAGEB6; MAGEC1; MAGEC2; PAGE1; PAGE2; PAGE5; PLAC1; PRAME; SPANXA1; SPANXB2; SPANXD; SSX1; SSX3; SSX4B; SSX7; HLA-DRB1; EIF4E; EIF4G1; NUP35; UBE2L6; GBP2; HLA-A; HLA-DPB1; HLA-F; IFITM2; IFITM3; MX2; UBE2E1; FAS; FASLG; HLA-DMA; HLA-E; GBP5; IFNGR1; IRF6; VCAM1; IL1A; IL1B; IL6; CCL4; PPBP; EIF4E; EIF4G1; HLA-DRB1; LYN; NUP35; UBE2L6; CASP1; GBP2; HLA-A; HLA-DPB1; HLA-F; IFITM2; IFITM3; IL18; IL6R; IL7R; MX2; NFKB2; UBE2E1; CCL28; CCL3; CCL3L3; CXCR7; GBP5; IFNGR1; IL1A; IL1B; IL6; IRF6; NOD2; STAT5A; VCAM1; PSMA3; CALR; HLA-A; HLA-F; PSME2; ITGAV; ADORA2B; ANXA1; AOC3; CAMP; CCL4; NLRP3; WAS; APOBEC3G; BNIP3; CD19; CEBPB; CEBPG; DEFB1; HP; INHBB; KLRC4; LY75; MX2; NMI; SCG2; TCIRG1; TLR3; TPST1; VWF; CCL3; CCL3L3; FOSL1; IL1A; INHBA; NOD2; PLA2G7; PTX3; S100A7; S100A9; TYROBP; DCBLD2; GP9; PROS1; NUP35; RPL38; XPO1; CALR; RPS27; RPS8; ACTL8; CEP55; OIP5; PASD1; PBK; TMEFF2; TTK; CSAG2; CXorf48; GAGE3; GPAT2; LEMD1; LY6K; MAGEA1; MAGEA11; MAGEA6; MAGEB1; PAGE2B; POTEB; POTEG; SSX2; and ZNF165. The foregoing includes, for example, combinations of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, and 291 biomarkers.

In another embodiment, the cancer is breast cancer and the AIM panel comprises one or more of IRF8; JAK2; EIF2AK2; TPR; NLRX1; HLA-DMB; CCR9; CXCL12; CXCL9; EIF2AK2; IL6ST; IRF8; JAK2; PIK3R2; TPR; PSMC6; MRC2; ADORA2A; BCL2; CCR9; CD81; CRP; CXCL9; DEFB103A; LBP; NCF1; ORM1; ORM2; TGFB2; and TPR. The foregoing includes, for example, combinations of 2, 3, 4, 5, 6, 7, 8, 9, 10, 11, 12, 13, 14, 15, 16, 17, 18, 19, 20, 21, 22, 23, 24, 25, 26, 27, 28, 29, and 30 biomarkers. In more specific embodiments, the cancer is a breast cancer and the AIM panel comprises one or more of IFI27, IFI6, IFIT1, IFITM1, IRF9, ISG15, MX1, and OASL. The foregoing includes, for example, combinations of 2, 3, 4, 5, 6, 7, 8 of IFI27, IFI6, IFIT1, IFITM1, IRF9, ISG15, MX1, and OASL.

In a further embodiment, the cancer is colon cancer and the AIM panel comprises one or more of CAMK2B; HLA-DRB3; PTAFR; PTPN1; EIF4A2; KPNA2; KPNA3; NUP107; NUP155; NUP205; NUP37; NUP43; NUP85; NUP93; SEH1L; UBE2N; GZMB; PRF1; CCR7; CXCL10; CXCL16; CXCR3; PF4; CAMK2B; CDK1; CSF2RB; EIF4A2; HLA-DRB3; HRAS; IL1R1; IL1RN; IL2RA; IL2RG; IRAK1; KPNA2; KPNA3; MAP2K4; NRAS; NUP107; NUP155; NUP205; NUP37; NUP43; NUP85; NUP93; PELI3; PRL; PTAFR; PTPN1; RBX1; SEH1L; SH2B1; SHC1; UBE2N; PSMA6; PSMB10; PSMB3; PSMB6; PSMD1; PSMD10; SEC61B; SEC61G; ITGB5; AFAP1L2; AIF1; APOBEC3F; CADM1; CCR7; CD83; CXCL10; CYSLTR1; GAGE1; IL17RB; KLRC3; LGALS3BP; LYZ; MGLL; MICB; NFATC4; NOS2; OR2H2; PRF1; PSG8; PTAFR; PYDC1; S100A12; TFF3; UMOD; F2; F2R; F5; F7; MIA3; PF4; SOD1; GTF2F2; NUP107; NUP155; NUP205; NUP37; NUP43; NUP85; NUP93; POLR2K; POLR2L; RPL11; RPL12; RPL14; RPL15; RPL37A; RPL4; RPL41; RPLP1; RPS11; RPS14; RPS18; RPS23; RPS28; RPS4Y1; RPS6; SEH1L; CASC5; CT47B1; DKKL1; GAGE1; LUZP4; NXF2; PAGE4; POTEC; POTED; POTEE; RGS22; RQCD1; SPA17; XAGE2B; XAGE3; and XAGE5. The foregoing includes, for example, combinations of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, and 137 biomarkers. In more specific embodiments, the cancer is a colon cancer and the AIM panel comprises one or more of CTGF, HSP90AA1, IFI27, IFI6, IFITM1, KLK8, MDK, MT2A, OAS3, PAGE1, PLAT, DEFB1, POLR2L, and TCIRG1. The foregoing includes, for example, combinations of 2, 3, 4, 5, 6, 7, 8, 9, 10, 11, 12, 13, and 14 biomarkers.

In yet another embodiment, the cancer is ovarian cancer and the AIM panel comprises one or more of GBP4; HLA-DPA1; HLA-G; IFNG; PTPN6; IFI35; RNASEL; STAT2; CCRL1; CXCL5; CXCR6; XCL1; XCL2; CSF2RA; CSH1; GBP4; GH1; HLA-DPA1; HLA-G; IFI35; IFNG; IL2RB; MAP3K8; PELI1; PELI2; PTPN6; RNA-SEL; STAT2; VAV1; HLA-G; CD36; APOL3; BNIP3L; C2; CD1D; CD40; CFP; CHST2; COLEC12; DCDC2; DMBT1; ELF3; GPR68; HLA-G; IL29; KRT1; MST1R; NOX4; SP140; STAB1; TNFAIP6; TNIP1; CD36; F12; HOXB13; LYVE1; PROC; RPS12; ACRBP; DPPA2; HSPB9; PIWIL2; SAGE1; SYCE1; TMEFF1; TSGA10; and XAGE-4. The foregoing includes, for example, combinations of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, and 67 biomarkers. In more specific embodiments, the cancer is ovarian cancer and the AIM panel comprises one or more of IFI27, IFITM1, IL6, GBP5, IL32, IL8, NCF2, PLAT, CXCL2, GBP1, HLA-C, ICAM1, IFI6, IFIT1, IRF7, and TAP1. The foregoing includes, for example, combinations of 2, 3, 4, 5, 6, 7, 8, 9, 10, 11, 12, 13, 14, 15, and 16 biomarkers.

In a further embodiment, the cancer is lung cancer and the AIM panel comprises one or more of CCL26, CCL5, DDX58, ICAM1, IFI27, IFI6, IFIT1, IFITM1, IL32, IL6, ISG15, MX1, NCF2, OASL, and TAP1. The foregoing includes, for example, combinations of 2, 3, 4, 5, 6, 7, 8, 9, 10, 11, 12, 13, 14, and 15 biomarkers.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

In particular embodiments, the biomarker panels of the present invention may show a statistical difference in different immune signature statuses of at least $p<0.05$, $p<10^{-2}$, $p<10^{-3}$, $p<10^{-4}$ or $p<10^{-5}$. Diagnostic tests that use these biomarkers may show an ROC of at least 0.6, at least about 0.7, at least about 0.8, or at least about 0.9.

In certain embodiments, the biomarkers are measured in a patient sample using the methods described herein and an immune signature status is calculated. In particular embodiments, the measurement(s) may then be compared with a relevant diagnostic amount(s), cut-off(s), or multivariate model scores that distinguish a high immune signature (AIM high) status from a low immune signature (AIM low) status. The diagnostic amount(s) represents a measured amount of a biomarker(s) above which or below which a patient is classified as having a particular immune signature status. As is well understood in the art, by adjusting the particular diagnostic cut-off(s) used in an assay, one can increase sensitivity or specificity of the diagnostic assay depending on the preference of the diagnostician. In particular embodiments, the particular diagnostic cut-off can be determined, for example, by measuring the amount of biomarkers in a statistically significant number of samples from patients with different immune signature statuses, and drawing the cut-off to suit the desired levels of specificity and sensitivity.

Furthermore, in certain embodiments, the values measured for markers of a biomarker panel are mathematically combined and the combined value is correlated to the underlying diagnostic question of high or low AIM immune signature. Biomarker values may be combined by any appropriate state of the art mathematical method. Well-known mathematical methods for correlating a marker combination to a disease status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate a biomarker combination of the present invention. In one embodiment, the method used in a correlating a biomarker combination of the present invention is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al., 12 J. OF COMPUTATIONAL AND GRAPHICAL STATISTICS 475-511 (2003); Friedman, J. H., 84 J. OF THE AMERICAN STATISTICAL ASSOCIATION 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45 MACHINE LEARNING 5-32 (2001); Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

B. Generation of Classification Algorithms for Qualifying Immune Signature Status In some embodiments, data that are generated using samples such as "known samples" can then be used to "train" a classification model. A "known sample" is a sample that has been pre-classified. The data that are used to form the classification model can be referred to as a "training data set." The training data set that is used to form the classification model may comprise raw data or pre-processed data. Once trained, the classification model can recognize patterns in data generated using unknown samples. The classification model can then be used to classify the unknown samples into classes. This can be useful, for example, in predicting whether or not a particular biological sample is associated with a certain biological condition.

Classification models can be formed using any suitable statistical classification or learning method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART), artificial neural networks such as back propagation networks, discriminant analyses (e.g., Bayesian classifier or Fischer analysis), logistic classifiers, and support vector classifiers (support vector machines).

Another supervised classification method is a recursive partitioning process. Recursive partitioning processes use recursive partitioning trees to classify data derived from unknown samples. Further details about recursive partitioning processes are provided in U.S. Patent Application No. 2002 0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application Publication No. 2002/0193950 (Gavin et al. "Method or analyzing mass spectra"), U.S. Patent Application Publication No. 2003/0004402 (Hitt et al., "Process for discriminating between biological states based on hidden patterns from biological data"), and U.S. Patent Application Publication No. 2003/0055615 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows® or Linux™ based operating system. In embodiments utilizing a mass spectrometer, the digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including R, C, C++, visual basic, etc.

The learning algorithms described above are useful both for developing classification algorithms for the biomarkers already discovered, and for finding new biomarker biomarkers. The classification algorithms, in turn, form the base for diagnostic tests by providing diagnostic values (e.g., cut-off points) for biomarkers used singly or in combination.

IV. Kits for the Detection of Immune Signature Biomarkers

In another aspect, the present invention provides kits for qualifying immune signature status, which kits are used to detect the biomarkers described herein. In a specific embodiment, the kit is provided as a PCR kit comprising primers that specifically bind to one or more of the biomarkers described herein. One of ordinary skill in the art can design primers the specifically bind and amplify the target biomarkers. The kit can further comprise substrates and other reagents necessary for conducting PCR (e.g., quantitative real-time PCR). The kit can be configured to conduct singleplex or multiplex PCR. The kit can further comprise instructions for carrying out the PCR reaction(s). In specific embodiments, the biological sample obtained from a subject may be manipulated to extract nucleic acid. In a further embodiment, the nucleic acids are contacted with primers that specifically bind the target biomarkers to form a primer:biomarker complex. The complexes can then be amplified and detected/quantified/measured to determine the levels of one or more biomarkers. The subject can then be identified as having a particular immune signature (e.g., AIM high or AIM low) based on a comparison of the measured levels of one or more biomarkers to one or more reference controls and/or a comparison of one set of biomarkers to another set of biomarkers.

In other specific embodiments, the kit is provided as an ELISA kit comprising binding agents to the biomarkers of the present invention including, but not limited to, B2M; CD44; GBP1; HLA-B; HLA-C; ICAM1; IRF7; IRF9; MT2A; OAS1; OAS2; OAS3; OASL; STAT1; EGR1; IFI27; IFI6; IFIT1; IFIT2; IFIT3; IFITM1; ISG15; ISG20; MX1; PSMB8; USP18; XAF1; DDX58; HERC5; UBA7; IFIH1; TNFAIP3; CCL2; CCL20; CCL5; CXCL1; CXCL11; CXCL2; CXCL3; CXCL6; CXCR4; IL8; B2M; CD44; CSF2; DDX58; EGR1; GBP1; HERC5; HLA-B; HLA-C; ICAM1; IFI27; IFI6; IFIT1; IFIT2; IFIT3; IFITM1; IL1R2; IRF7; IRF9; ISG15; ISG20; LCK; MT2A; MX1; OAS1; OAS2; OAS3; OASL; PSMB8; STAT1; UBA7; USP18; XAF1; B2M; HLA-B; HLA-C; PSMB8; PSMB9; TAP1; CTSS; NCF2; ALOX5AP; ANKRD1; AOX1; CCL20; CCL26; CCL5; CXCL1; CXCL11; CXCL2; CXCL6; CXCR4; EREG; FOS; HCP5; HLA-B; IL32; IL8; KCNN4; KLRC2; LSP1; LY96; LYST; MX1; NCF2; PAGE1; RSAD2; S100A8; ADM; C4BPB; CTGF; KLK8; MDK; PLAT; SERPINE1; SPRR3; TFPI; THBD; HSP90AA1; RPL26; ATAD2; CABYR; CSAG1; CT45A1; CT45A5; CT47A11; CTAG1A; CTAG2; CTCFL; DDX43; DSCR8; FAM133A; FMR1NB; GAGE7; HORMAD1; IL13RA2; MAEL; MAGEA10; MAGEA12; MAGEA2B; MAGEA4; MAGEA8; MAGEA9; MAGEB2; MAGEB6; MAGEC1; MAGEC2; PAGE1; PAGE2; PAGE5; PLAC1; PRAME; SPANXA1; SPANXB2; SPANXD; SSX1; SSX3; SSX4B; SSX7; HLA-DRB1; EIF4E; EIF4G1; NUP35; UBE2L6; GBP2; HLA-A; HLA-DPB1; HLA-F; IFITM2; IFITM3; MX2; UBE2E1; FAS; FASLG; HLA-DMA; HLA-E; GBP5; IFNGR1; IRF6; VCAM1; IL1A; IL1B; IL6; CCL4; PPBP; EIF4E; EIF4G1; HLA-DRB1; LYN; NUP35; UBE2L6; CASP1; GBP2; HLA-A; HLA-DPB1; HLA-F; IFITM2; IFITM3; IL18; IL6R; IL7R; MX2; NFKB2; UBE2E1; CCL28; CCL3; CCL3L3; CXCR7; GBP5; IFNGR1; IL1A; IL1B; IL6; IRF6; NOD2; STAT5A; VCAM1; PSMA3; CALR; HLA-A; HLA-F; PSME2; ITGAV; ADORA2B; ANXA1; AOC3; CAMP; CCL4; NLRP3; WAS; APOBEC3G; BNIP3; CD19; CEBPB; CEBPG; DEFB1; HP; INHBB; KLRC4; LY75; MX2; NMI; SCG2; TCIRG1; TLR3; TPST1; VWF; CCL3; CCL3L3; FOSL1; IL1A; INHBA; NOD2; PLA2G7; PTX3; S100A7; S100A9; TYROBP; DCBLD2; GP9; PROS1; NUP35; RPL38; XPO1; CALR; RPS27; RPS8; ACTL8; CEP55; OIP5; PASD1; PBK; TMEFF2; TTK; CSAG2; CXorf48; GAGE3; GPAT2; LEMD1; LY6K; MAGEA1; MAGEA11; MAGEA6; MAGEB1; PAGE2B; POTEB; POTEG; SSX2; and ZNF165 and combinations of all of the foregoing.

The ELISA kit may comprise a solid support, such as a chip, microtiter plate (e.g., a 96-well plate), bead, or resin having biomarker capture reagents attached thereon. The kit may further comprise a means for detecting the biomarkers, such as antibodies, and a secondary antibody-signal complex such as horseradish peroxidase (HRP)-conjugated goat anti-rabbit IgG antibody and tetramethyl benzidine (TMB) as a substrate for HRP. In other embodiments, the kit can comprise magnetic beads conjugated to the antibodies (or separate containers thereof for later conjugation). The kit can further comprise detection antibodies, for example, biotinylated antibodies that can be detected using, for example, streptavidin labeled fluorescent markers such as phycoerythrin. The kit can be configured to perform the assay in a singleplex or multiplex format.

In certain embodiments, a patient can be diagnosed by adding blood or blood serum from the patient to the kit and detecting the relevant biomarkers conjugated with antibodies, specifically, by a method which comprises the steps of: (i) collecting blood or blood serum from the patient; (ii) separating blood serum from the patient's blood; (iii) adding the blood serum from patient to a diagnostic kit; and, (iv) detecting the biomarkers conjugated with antibodies. In this method, the antibodies are brought into contact with the patient's blood. If the biomarkers are present in the sample, the antibodies will bind to the sample, or a portion thereof. In other kit and diagnostic embodiments, blood or blood serum need not be collected from the patient (i.e., it is already collected). Moreover, in other embodiments, the sample may comprise a tissue sample or a clinical sample.

The kit can also comprise a washing solution or instructions for making a washing solution, in which the combination of the capture reagents and the washing solution allows capture of the biomarkers on the solid support for subsequent detection by, e.g., antibodies/lectins or mass spectrometry. In a further embodiment, a kit can comprise instructions for suitable operational parameters in the form of a label or separate insert. For example, the instructions may inform a consumer about how to collect the sample, how to wash the probe or the particular biomarkers to be detected, etc. In yet another embodiment, the kit can comprise one or more containers with biomarker samples, to be used as standard(s) for calibration.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Cell Line Treatments.

63 cell lines (26 breast cancer, 14 colorectal cancer, 23 ovarian cancer) were used in these experiments. Breast cell lines included BT20, BT474, CAMA1, EFM19, MDA453, MDA468, MDA361, MCF7, MDA231, T47D, HCC1500, and HCC1187 obtained from the American Type Tissue Collection; HCC1419, HCC38, EFM192A, HCC1569, HCC1937, HCC1954, MDA175, MDA415, MDA436, SUM149, SUM159, SKBR3, ZR751, and ZR7530 from Dr. Dennis Slamon. All cells were maintained under recommended conditions. Colorectal cell lines were all obtained from the American Type Tissue Collection and were maintained under recommended conditions. These included CACO-2, Colo201, Colo205, Colo320, DLD1, HCT116, HT29, Lovo, RKO, SK-CO1, SNUC-1, SW48, SW480, and SW620. Ovarian cell lines were obtained from the laboratory of Dr. Dennis Slamon and included A2780, CAOV3, DOV13, EFO27, ES2, Hey, HEYC2, Kuramochi, OAW28, OAW42, OV167, OV2008, OV90, OVCA429, OVCA432, OVMANA, OVCAR3, OVCAR5, OVKATE, PEO14, SKOV3, TOV112D, and TykNu; these were maintained under the ATCC recommended conditions.

Cell lines were treated with 500 nM of AZA or carboplatin (Sigma; St. Louis, Mo.) for 72 hours while in log-growth phase, changing the media and drug every 24 hours for AZA treatment. To select an appropriate chemotherapy control, the carboplatin dose that had the similar growth inhibitory effect to 500 nM AZA after 10 days was selected. Cells were harvested at 1, 3, 7, 10, 14, 21, or 28 days following initial application of drug. DNA and RNA were obtained using standard protocols. RNA from 63 cell lines was sent for the Agilent 44K Expression Array and DNA from 53 cell lines was sent for the Illumina 450K Methylation Array.

Clinical Trials.

Patients were recruited to clinical trials NCT01349959 (breast cancer) and NCT01105377 (colon cancer). Patients received 40 mg/m$^{-2}$ 5-azacitidine subcutaneously on days 1-5 and 8-10 and 7 mg oral Entinostat on days 3 and 10. Courses were repeated every 28 days in the absence of disease progression or unacceptable toxicity. RNA was isolated from pre-(baseline) and post-treatment (8 weeks) biopsies and analyzed with the Agilent 44K Expression Array.

Bioinformatics.

All data were analyzed using R: A Language and Environment for Statistical Computing. Expression normalization of cell line data was performed using the package Limma as previously described. Data was normalized within each tumor type (breast, colorectal, and ovarian). These normalized values were then analyzed utilizing the Gene Set Enrichment Analysis by the Broad Institute and data packages (C5BP, Reactome, KEGG). Pathways enriched with a false discovery rate less than 0.25 and normalized enrichment score >2.15 (upregulated gene sets), or <-2.15 (downregulated gene sets) were chosen. These criteria represented the ~top 30% of all upregulated gene sets as determined by the NES score. Pathways common among breast, colorectal, and ovarian tumors were identified. Pathways were manually curated into specific categories. AIMs were defined by intersection of all genes from the enriched GSEA gene sets with over 2 fold upregulated genes after AZA treatment for any cell line, any time point. Genes were defined as demethylated if they met the following criteria: had a high basal β value ≥0.5 and a $\Delta\beta_{(AZA-Mock)}$≤−0.25, were expressed at low basal levels in the untreated cells (lower than 50% of the expression quantile) and expressed at higher levels in the AZA treated cells (>2-fold). For β values, the only gene probes included in the analysis were those that recognized the CpG island within the promoter. Demethylated/re-expressed genes had to meet both demethylation and re-expression criteria in at least one cell line. TCGA HumanMethylation27K level 3 data was downloaded, standard deviation of Infinium β-values across all primary cancer samples were calculated, and the top one thousand most variable probes were chosen for hierarchical cluster analysis. Based on the dendrogram and overall methylation status, primary cancer samples were classified as CIMP high, CIMP intermediate and CIMP low.

Validations (qRT-PCR).

After total cellular RNA was extracted using the Trizol method (Life Technologies, Carlsbad, Calif.), RNA concentration was determined using the Nanodrop machine and software (Thermo Fisher Scientific, Rockville, Md.). 1 μg total RNA was used to generate cDNA with the QuantiTect Reverse Transcription Kit (Qiagen, Venlo, Netherlands). Quantitative reverse transcription PCR (q-RT-PCR) of CD274, DDX58, HLA-C, IFI6, IFI27, IL-15, IRF7, IRF9, MAEL, and MAGEB2 mRNA was performed using Taq-Man assays (Life Technologies, Carlsbad, Calif.) and the Applied Biosystems 7500 Fast real-time PCR system and software. Human β-actin mRNA was used as the endogenous control. The ΔΔCT method was used to calculate relative expression levels. All qRT-PCR assays were carried out in triplicate and then repeated with new cDNA synthesis. Minus RT controls (reverse transcriptase negative cDNA synthesis reactions) were performed for at least one sample per plate.

TABLE 1

| Gene Set Categories | Common Genes in 3 Types of Cancer | Common Genes in Any 2 Types | Unique Genes Breast |
|---|---|---|---|
| Interferon (42.3%) | B2M; CD44; GBP1; HLA-B; HLA-C; ICAM1; IRF7; IRF9; MT2A; OAS1; OAS2; OAS3; OASL: STAT1; EGR1; IFI27; IFI6; IFIT1; IFIT2; IFIT3; IFITM1; ISG15; ISG20; MX1; PSMB8; USP18; XAF1; DDX58; HERC5; UBA7; IFIH1; TNFAIP3 | HLA-DRB1; EIF4E; EIF4G1; NUP35; UBE2L6; GBP2; HLA-A; HLA-DPB1; HLA-F; IFITM2; IFITM3; MX2; UBE2E1; FAS; FASLG; HLA-DMA; HLA-E; GBP5; IFNGR1; IRF6; VCAM1; IL1A; IL1B; IL6 | IRF8; JAK2; EIF2AK2; TPR; NLRX1; HLA-DMB |
| Cytokine/ Chemokine (43.7%) | CCL2; CCL20; CCL5; CXCL1; CXCL11; CXCL2; CXCL3; CXCL6; CXCR4; IL8; B2M; CD44; CSF2; DDX58; EGR1; GBP1; HERC5; HLA-B; HLA-C; ICAM1; IFI27; IFI6; IFIT1; IFIT2; IFIT3; IFITM1; IL1R2; IRF7; IRF9; ISG15; ISG20; LCK; MT2A; MX1; OAS1; OAS2; OAS3; OASL; PSMB8; STAT1; UBA7; USP18; XAF1 | CCL4; PPBP; EIF4E; EIF4G1; HLA-DRB1; LYN; NUP35; UBE2L6; CASP1; GBP2; HLA-A; HLA-DPB1; HLA-F; IFITM2; IFITM3; IL18; IL6R; IL7R; MX2; NFKB2; UBE2E1; CCL28; CCL3; CCL3L3; CXCR7; GBP5; IFNGR1; IL1A; IL1B; IL6; IRF6; NOD2; STAT5A; VCAM1 | CCR9; CXCL12; CXCL9; EIF2AK2; IL6ST; IRF8; JAK2; PIK3R2; TPR |
| Ag Presentation (35.5%) | B2M; HLA-B; HLA-C; PSMB8; PSMB9; TAP1; CTSS; NCF2 | PSMA3; CALR; HLA-A; HLA-F; PSME2; ITGAV | PSMC6; MRC2 |
| Inflammation (44.2%) | ALOX5AP; ANKRD1; AOX1; CCL20; CCL26; CCL5; CXCL1; CXCL11; CXCL2; CXCL6; CXCR4; EREG; FOS; HCPS; HLA-B; IL32; IL8; KCNN4; KLRC2; LSP1; LY96; LYST; MX1; NCF2; PAGE1; RSAD2; S100A8; ADM; C4BPB; CTGF; KLK8; MDK; PLAT; SERPINE1; SPRR3; TFPI; THBD | ADORA2B; ANXA1; AOC3; CAMP; CCL4; NLRP3; WAS; APOBEC3G; BNIP3; CD19; CEBPB; CEBPG; DEFB1; HP; INHBB; KLRC4; LY75; MX2; NMI; SCG2; TCIRG1; TLR3; TPST1; VWF; CCL3; CCL3L3; FOSL1; IL1A; INHBA; NOD2; PLA2G7; PTX3; S100A7; S100A9; TYROBP; DCBLD2; GP9; PROS1 | ADORA2A; BCL2; CCR9; CD81; CRP; CXCL9; DEFB103A; LBP; NCF1; ORM1; ORM2; TGFB2 |
| Influenza (17.7) | HSP90AA1; RPL26 | NUP35; RPL38; XPO1; CALR; RPS27; RPS8 | TPR |
| Cancer Testis Antigens (31.4%) | ATAD2; CABYR; CSAG1; CT45A1; CT45A5; CT47A11; CTAG1A; CTAG2; CTCFL; DDX43; DSCR8; FAM133A; FMR1NB; GAGE7; HORMAD1; IL13RA2; MAEL; MAGEA10; MAGEA12; MAGEA2B; MAGEA4; MAGEA8; MAGEA9; MAGEB2; MAGEB6; MAGEC1; MAGEC2; PAGE1; PAGE2; PAGE5; PLAC1; PRAME; SPANXA1; SPANXB2; SPANXD: SSX1; SSX3; SSX4B: SSX7 | ACTL8; CEP55; OIP5; PASD1; PBK; TMEFF2; TTK; CSAG2; CXorf48; GAGE3; GPAT; LEMD1; LY6K; MAGEA1; MAGEA11; MAGEA6; MAGEB1; PAGE2B; POTEB; POTEG; SSX2; ZNF165 | |

| Gene Set Categories | Unique Genes | |
|---|---|---|
| | Colon | Ovarian |
| Interferon (42.3%) | CAMK2B; HLA-DRB3; PTAFR; PTPN1; EIF4A2; KPNA2; KPNA3; NUP107; NUP155; NUP205; NUP37; NUP43; NUP85; NUP93; SEH1L; UBE2N; GZMB; PRF1 | GBP4; HLA-DPA1; HLA-G; IFNG; PTPNG; IFI35; RNASEL; STAT2 |
| Cytokine/ Chemokine (43.7%) | CCR7; CXCL10; CXCL16; CXCR3; PF4; CAMK2B; CDK1; CSF2RB; EIF4A2; HLA-DRB3; HRAS; IL1R1; IL1RN; IL2RA; IL2RG; IRAK1; KPNA2; KPNA3; MAP2K4; NRAS; NUP107; NUP155; NUP205; NUP37; NUP43; | CCRL1; CXCL5; CXCR6; XCL1; XCL2; CSF2RA; CSH1; GBP4; GH1; HLA-DPA1; HLA-G; IFI35; IFNG; IL2RB; MAP3K8; PELI1; PELI2; PTPN6; RNASEL; STAT2; VAV1 |

TABLE 1-continued

| | | |
|---|---|---|
| | | NUP85; NUP93; PELI3; PRL; PTAFR; PTPN1; RBX1; SEH1L; SH2B1; SHC1; UBE2N | |
| Ag Presentation (35.5%) | PSMA6; PSMB10; PSMB3; PSMB6; PSMD1; PSMD10; SEC61B; SEC61G; ITGB5 | HLA-G; CD36 |
| Inflammation (44.2%) | AFAP1L2; AIF1; APOBEC3F; CADM1; CCR7; CD83; CXCL10; CYSLTR1; GAGE1; IL17RB; KLRC3; LGALS3BP; LYZ; MGLL; MICB; NFATC4; NOS2; OR2H2; PRF1; PSG8; PTAFR; PYDC1; S100A12; TFF3; UMOD; F2; F2R; F5; F7; MIA3; PF4; SOD1 | APOL3; BNIP3L; C2; CD1D; CD40; CFP; CHST2; COLEC12; DCDC2; DMBT1; ELF3; GPR68; HLA-G; IL29; KRT1; MST1R; NOX4; SP140; STAB1; TNFAIP6; TNIP1; CD36; F12; HOXB13; LYVE1; PROD |
| Influenza (17.7) | GTF2F2; NUP107; NUP155; NUP205; NUP37; NUP43; NUP85; NUP93; POLR2K; POLR2L; RPL11; RPL12; RPL14; RPL15; RPL37A; RPL4; RPL41; RPLP1; RPS11; RPS14; RPS18; RPS23; RPS28; RPS4Y1; RPS6; SEH1L | RPS12 |
| Cancer Testis Antigens (31.4%) | CASC5; CT47B1; DKKL1; GAGE1; LUZP4; NXF2; PAGE4; POTEC; POTED; POTEE; RGS22; RQCD1; SPA17; XAGE2B; XAGE3; XAGE5 | ACRBP; DPPA2; HSPB9; PIWIL2; SAGE1; SYCE1; TMEFF1; TSGA10; XAGE-4 |

TABLE 2

| | Immune | Cell Cycle, Mitosis, Meiosis | Mrna splicing and translation |
|---|---|---|---|
| Upregulated Common Gene sets (80) | DEFENSE_RESPONSE | CELL_CYCLE_CHECKPOINT_ G0_0000075 | KEGG_RIBOSOME |
| | RESPONSE_TO_WOUNDING | CELL_CYCLE_G0_0007049 | REACTOME_SRP_DEPENDENT_ COTRANSLATIONAL_PROTEIN_ TARGETING_TO_MEMBRANE |
| | INFLAMMATORY_ RESPONSE | M_PHASE_OF_MITOTIC_ CELL_CYCLE | REACTOME_PEPTIDE_CHAIN_ ELONGATION |
| | KEGG_SYSTEMIC_LUPUS_ ERYTHEMATOSUS | MITOSIS | REACTOME_TRANSLATION |
| | KEGG_GRAFT_VERSUS_ HOST_DISEASE | MITOTIC_CELL_CYCLE | REACTOME_3_UTR_MEDIATED_ TRANSLATIONAL_REGULATION |
| | REACTOME_CHEMOKINE_ RECEPTORS_BIND_ CHEMOKINES | CELL_CYCLE_PHASE | REACTOME_METABOLISM_OF_RNA |
| | REACTOME_INFLUENZA_ LIFE_CYCLE | CELL_CYCLE_PROCESS | REACTOME_METABOLISM_OF_MRNA |
| | REACTOME_INFLUENZA_ VIRAL_RNA_ TRANSCRIPTION_AND_ REPLICATION | M_PHASE | REACTOME_FORMATION_OF_THE_ TERNARY_COMPLEX_AND_SUBSEQUENTLY_ THE_43S_COMPLEX |
| | REACTOME_ER_ PHAGOSOME_PATHWAY | KEGG_CELL_CYCLE | REACTOME_ACTIVATION_OF_THE_ MRNA_UPON_BINDING_OF_THE_CAP_ BINDING_COMPLEX_AND_EIFS_AND_ SUBSEQUENT_BINDING_TO_43S |
| | REACTOME_CYTOKINE_ SIGNALING_IN_ IMMUNE_SYSTEM | REACTOME_G2_M_ CHECKPOINTS | REACTOME_MRNA_SPLICING |
| | REACTOME_ANTIGEN_ PROCESSING_CROSS_ PRESENTATION | REACTOME_APC_C_CDH1_ MEDIATED_DEGRADATION_ OF_CDC20_AND_OTHER_ APC_C_CDH1_TARGETED_ PROTEINS_IN_LATE_ MITOSIS_EARLY_G1 | REACTOME_DESTABILIZATION_OF_ MRNA_BY_AUF1_HNRNP_D0 |
| | REACTOME_INTERFERON_ GAMMA_SIGNALING | REACTOME_MEIOTIC_ RECOMBINATION | REACTOME_PROCESSING_OF_ CAPPED_INTRON_CONTAINING_ PRE_MRNA |
| | REACTOME_INTERFERON_ ALPHA_BETA_SIGNALING | REACTOME_M_G1_ TRANSITION | |
| | REATOME_ANTIVIRAL_ MECHANISM_BY_IFN_ STIMULATED_GENES | REACTOME_MEIOSIS | |
| | REACTOME_INTERFERON_ SIGNALING | REACTOME_CELL_ CYCLE_CHECKPOINTS | |

TABLE 2-continued

| | | | |
|---|---|---|---|
| REACTOME_NEGATIVE_REGULATORS_OF_RIG_I_MDA5_SIGNALING | REACTOME_DEPOSITION_OF_NEW_CENPA_CONTAINING_NUCLEOSOMES_AT_THE_CENTROMERE<br>REACTOME_MEIOTIC_SYNAPSIS<br>REACTOME_MITOTIC_G1_G1_S_PHASES<br>REACTOME_G1_S_SPECIFIC_TRANSCRIPTION<br>REACTOME_APC_C_CDC20_MEDIATED_DEGRADATION_OF_MITOTIC_PROTEINS<br>REACTOME_REGULATION_OF_MITOTIC_CELL_CYCLE<br>REACTOME_CELL_CYCLE_MITOTIC<br>REACTOME_CELL_CYCLE<br>REACTOME_MITOTIC_G2_G2_M_PHASES<br>REACTOME_MITOTIC_M_M_G1_PHASES<br>REACTOME_S_PHASE<br>REACTOME_MITOTIC_PROMETAPHASE<br>REACTOME_G1_S_TRANSITION<br>REACTOME_CYCLIN_E_ASSOCIATED_EVENTS_DURING_G1_S_TRANSITION_ | | |
| | DNA Replication, and Packaging, Transcription | | Others |
| | Upregulated Common Gene sets (80) | DNA_REPLICATION<br><br>DNA_DEPENDENT_DNA_REPLICATION<br>KEGG_DNA_REPLICATION<br><br>REACTOME_NONSENSE_MEDIATED_DECAY_ENHANCED_BY_THE_EXON_JUNCTION_COMPLEX<br>REACTOME_RNA_POL_I_PROMOTER_OPENING<br><br>REACTOME_PACKAGING_OF_TELOMERE_ENDS<br>REACTOME_DNA_REPLICATION<br>REACTOME_RNA_POL_I_TRANSCRIPTION<br>REACTOME_TELOMERE_MAINTENANCE<br>REACTOME_RNA_POL_I_RNA_POL_III_AND_MITOCHONDRIAL_TRANSCRIPTION<br>REACTOME_DNA_STRAND_ELONGATION<br>REACTOME_ACTIVATION_OF_THE_PRE_REPLICATIVE_COMPLEX<br>REACTOME_CHROMOSOME_MAINTENANCE<br>REACTOME_ASSEMBLY_OF_THE_PRE_REPLICATIVE_COMPLEX<br>REACTOME_ACTIVATION_OF_ATR_IN_RESPONSE_TO_REPLICATION_STRESS<br>REACTOME_ORC1_REMOVAL_FROM_CHROMATIN<br>REACTOME_E2F_MEDIATED_REGULATION_OF_DNA_REPLICATION<br>REACTOME_SYNTHESIS_OF_DNA | REACTOME_MUSCLE_CONTRACTION<br>REACTOME_AMYLOIDS<br><br>REACTOME_POST_CHAPERONIN_TUBULIN_FOLDING_PATHWAY<br>REACTOME_PREFOLDIN_MEDIATED_TRANSFER_OF_SUBSTRATE_TO_CCT_TRIC<br>REACTOME_FORMATION_OF_TUBULIN_FOLDING_INTERMEDIATES_BY_CCT_TRIC |

TABLE 3

| | Immune | Cell Cycle, Mitosis, Meiosis | Mrna splicing and translation |
|---|---|---|---|
| Downregulated Common Gene Sets (52) | KEGG_SYSTEMIC_LUPUS_ ERYTHEMATOSIS | MITOSIS | RNA_PROCESSING |
| | | MITOTIC_CELL_CYCLE | REACTOME_MRNA_ SPLICING |
| | | M_PHASE_OF_MITOTIC_ CELL_CYCLE | REACTOME_RNA_POL_I_ PROMOTER_OPENING |
| | | M_PHASE | REACTOME_PROCESSING_OF_ CAPPED_INTRON_CONTAINING_ PRE_MRNA |
| | | CELL_CYCLE_PHASE | REACTOME_RNA_POL_I_ TRANSCRIPTION |
| | | CELL_CYCLE_PROCESS | REACTOME_MRNA_PROCESSING |
| | | REACTOME_CELL_CYCLE | REACTOME_RNA_POL_I_RNA_ POL_III_AND_MITOCHONDRIAL_ TRANSCRIPTION |
| | | REACTOME_CELL_CYCLE_ MITOTIC | REACTOME_CYTOSOLIC_TRNA_ AMINOACYLATION |
| | | REACTOME_MEIOTIC_ SYNAPSIS | REACTOME_TRNA_ AMINOACYLATION |
| | | REACTOME_MITOTIC_ PROMETAPHASE | |
| | | REACTOME_MITOTIC_ M_M_G1_PHASES | |
| | | REACTOME_MEIOTIC_ RECOMBINATION | |
| | | REACTOME_G2_M_ CHECKPOINTS | |
| | | REACTOME_MEIOSIS | |
| | | REACTOME_REGULATION_OF_ MITOTIC_CELL_CYCLE | |
| | | REACTOME_S_PHASE | |
| | | REACTOME_G1_S_TRANSITION | |
| | | REACTOME_M_G1_TRANSITION | |
| | | REACTOME_G1_S_SPECIFIC_ TRANSCRIPTION | |

| | | DNA Replication, and Packaging, Transcription | Others |
|---|---|---|---|
| | Downregulated Common Gene Sets (52) | REACTOME_CLEAVAGE_OF_ GROWING_TRANSCRIPT_IN_ THE_TERMINATION_REGION_ | KEGG_STEROID_ BIOSYNTHESIS |
| | | REACTOME_DEPOSITION_OF_ NEW_CENPA_CONTAINING_ NUCLEOSOMES_AT_THE_ CENTROMERE | KEGG_VALINE_LEUCINE_ AND_ISOLEUCINE_ DEGRADATION |
| | | REACTOME_PACKAGING_OF_ TELOMERE_ENDS | REACTOME_AMYLOIDS |
| | | REACTOME_DNA_REPLICATION | REACTOME_ACTIVATION_ OF_CHAPERONE_GENES_ BY_XBP1S |
| | | REACTOME_CHROMOSOME_ MAINTENANCE | REACTOME_CHOLESTEROL_ BIOSYNTHESIS |
| | | REACTOME_DNA_STRAND_ ELONGATION | REACTOME_TCA_CYCLE_ AND_RESPIRATORY_ ELECTRON_TRANSPORT |
| | | REACTOME_TRANSCRIPTION | REACTOME_PERK_REGUATED_ GENE_EXPRESSION |
| | | REACTOME_TELOMERE_ MAINTENANCE | REACTOME_RESPIRATORY_ ELECTRON_TRANSPORT |
| | | REACTOME_SYNTHESIS_OF_ DNA | |
| | | REACTOME_ACTIVATION_OF_ THE_PRE_REPLICATIVE_ COMPLEX | |
| | | REACTOME_ACTIVATION_OF_ ATR_IN_RESPONSE_TO_ REPLICATION_STRESS | |
| | | REACTOME_LAGGING_STRAND_ SYNTHESIS | |
| | | REACTOME_EXTENSION_OF_ TELOMERES | |

TABLE 3-continued

REACTOME_E2F_MEDIATED_REGULATION_OF_DNA_REPLICATION
REACTOME_GENERIC_TRANSCRIPTION_PATHWAY

We claim:

1. A method comprising the step of measuring the expression of ISG20, IFI27, ISG15, IRF9, IFITM3, IRF7, IFI44L, IFITM1, OASL, IFI6, OAS2, STAT1, OAS1, MX1, IFIT1, IFI44, IFIH1, MX2 and DDX58 in a biological sample obtained from a human patient having ovarian cancer, wherein the measuring step is accomplished using an array or polymerase chain reaction.

2. The method of claim 1, wherein the biological sample is a tissue sample.

3. The method of claim 1, wherein the biological sample is formalin-fixed, paraffin embedded tissue.

4. The method of claim 1, wherein the PCR is qRT-PCR.

5. A method comprising the steps of:
   (a) measuring the expression of ISG20, IFI27, ISG15, IRF9, IFITM3, IRF7, IFI44L, IFITM1, OASL, IFI6, OAS2, STAT1, OAS1, MX1, IFIT1, IFI44, IFIH1, MX2 and DDX58 in a biological sample obtained from a human patient having or suspected of having ovarian cancer, wherein the measuring step is accomplished using an array or polymerase chain reaction;
   (b) comparing the expression to a reference of expression levels; and
   (c) treating the patient with immunotherapy if the measured expression levels are higher than the reference levels or treating the patient with epigenetic therapy followed by immunotherapy if the measured expression levels are lower than the reference levels.

6. The method of claim 5, wherein the biological sample is a tissue sample.

7. The method of claim 5, wherein the biological sample is formalin-fixed, paraffin embedded tissue.

8. The method of claim 5, wherein the PCR is qRT-PCR.

9. The method of claim 5, wherein the epigenetic therapy comprises treatment with a DNA methyltransferase inhibitor and/or a histone deactytelase inhibitor.

10. The method of claim 5, wherein the immunotherapy comprises a checkpoint inhibitor.

11. The method of claim 10, wherein the checkpoint inhibitor comprises anti PD1 or anti PDL1 antibodies.

* * * * *

UNITED STATES PATENT AND TRADEMARK OFFICE
CERTIFICATE OF CORRECTION

| | |
|---|---|
| PATENT NO. | : 10,619,210 B2 |
| APPLICATION NO. | : 15/115702 |
| DATED | : April 14, 2020 |
| INVENTOR(S) | : Nita Ahuja et al. |

It is certified that error appears in the above-identified patent and that said Letters Patent is hereby corrected as shown below:

In the Specification

Column 1 Lines 18-21, please replace the second paragraph as follows:
STATEMENT OF GOVERNMENTAL INTEREST
This invention was made with government support under grants CA058184 and CA127141 awarded by the National Institutes of Health, and under grant W81XWH-14-1-0385 awarded by the U.S. Army Medical Research and Development Command. The government has certain rights in the invention.

Signed and Sealed this
Twentieth Day of December, 2022

Katherine Kelly Vidal
Director of the United States Patent and Trademark Office